United States Patent
Castillo et al.

(10) Patent No.: US 7,314,724 B2
(45) Date of Patent: Jan. 1, 2008

(54) THERAPEUTIC APPLICATIONS OF LAMININ AND LAMININ-DERIVED PROTEIN FRAGMENTS

(75) Inventors: Gerardo Castillo, Seattle, WA (US); Alan D. Snow, Lynnwood, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/938,275

(22) Filed: Aug. 22, 2001

(65) Prior Publication Data

US 2002/0111309 A1    Aug. 15, 2002

Related U.S. Application Data

(63) Continuation of application No. 08/947,057, filed on Oct. 8, 1997, now abandoned.

(60) Provisional application No. 60/027,981, filed on Oct. 8, 1996.

(51) Int. Cl.
- G01N 33/567 (2006.01)
- G01N 33/566 (2006.01)
- C12N 5/00 (2006.01)
- C12N 5/02 (2006.01)
- C12N 5/08 (2006.01)
- A61K 38/00 (2006.01)
- C07K 1/00 (2006.01)
- C07K 14/00 (2006.01)
- C07K 17/00 (2006.01)

(52) U.S. Cl. ............... 435/7.21; 435/325; 435/368; 435/375; 424/9.2; 436/501; 436/503; 514/12; 530/350

(58) Field of Classification Search ............... 514/55, 514/1, 2, 12, 44; 530/350, 300; 435/7.1, 435/6; 436/501
See application file for complete search history.

(56) References Cited

OTHER PUBLICATIONS

Bronfman et al., 1996, neurosci. Lett., 218, pp. 201-203.*
Aksenova et al., 1996, Neurosci. Lett.,211, pp. 45-48.*
Cummings.J., 2004, New England J. Medicine, vol. 351, pp. 56-67.*
Koo et al. "Amyloid β-Protein as a Substrate Interacts with Extracellular Matrix to Promote Neurite Outgrowth," Proc. Natl. Acad. Science, vol. 90, pp. 4748-4752, May 1993.
Narindrasorsak et al. "Characterization of High Affinity Binding between Laminin and Alzheimer's Disease Amyloid Precursors Proteins," Laboratory Investigation, vol. 67, No. 5, pp. 643-652, 1992.
Narindrasorsak et al. "An Interaction between Basement Membrane and Alzheimer Amyloid Precursor Proteins Suggests a Role in the Pathogenesis of Alzheimer's Disease," Laboratory Investigation, vol. 72, No. 3, pp. 272-282, 1995.

(Continued)

Primary Examiner—Olga N. Chernyshev
(74) Attorney, Agent, or Firm—Patrick M. Dwyer

(57) ABSTRACT

Laminin and specific laminin-derived protein fragments are disclosed as potent inhibitors of Alzheimer's disease type amyloidoses. A specific region is identified within laminin which interacts with the Alzheimer's disease beta-amyloid protein and contributes to the observed inhibitory and therapeutic effects.

A prominent ~130 kilodalton band in laminin was found in human serum and cerebrospinal fluid which primarily interacted with Aβ as determined by ligand blotting methodology. This ~130 kilodalton laminin fragment is known as the E8 fragment and is also believed to consist of the globular domains of the laminin A chain. The interaction of specific laminin fragments such as the newly discovered ~130 kDa protein is believed to bind Aβ in biological fluids and keep it in a soluble state.

4 Claims, 14 Drawing Sheets

OTHER PUBLICATIONS

Mann. "Cerebral Amyloidosis, Ageing and Alzheimer's Disease; A Contribution From Studies on Down'Syndrome," Neurobiology of Aging, vol. 10, pp. 397-399, 1989.

Gajdusek. "Unconventional viruses and the Origen and Disappearance of Kuru," Science, vol. 197, No. 4307, Sep. 2, 1977.

Prusiner et al. "Purification and Structural Studies of a Major Scrapie Prion Protein," Cell vol. 38, 127-134, Aug. 1984.

Prusiner. "Prions," [publication data unknown].

Tateishi et al. "Gerstmann-Straussler-Scheinker Disease: Immunohistological and Experimental Studies," Annals of Nuerology, vol. 24, No. 1, Jul. 1988.

Foidart et al. "Distribution and Immunoelectron Microscopic Localization of Laminin, A Non collagenous Basement Membrane Glycoprotein," Laboratory Investigation, vol. 42, No. 3, p. 336, 1980.

Burgeson et al. "A New Nomenclature for the Laminins," Matrix Biology, vol. 14, pp. 209-211, 1994.

Yurchenco et al. "Laminin Polymerization in Vitro: Evidence for a two step assembly with Domain Specificity," The Journal of Biological Chemistry, vol. 260, No. 12, pp. 7636-7644, Jun. 25, 1985.

Yurchenco et al. "Laminin Forms an Independent Network in Basement Membranes," The journal of Cell Biology, vol. 117, No. 5, pp. 1119-1133, Jun. 1993.

Newgreen et al. "Fibronectin in Early Avian Embryos: Synthesis and Distribution Along the Migration Pathways of Neural Crest Cells," Cell tissue res. vol. 211, pp. 211-269, 1980.

Rovasio et al. "Neural Crest Cell Migration: Requirements for Exogenous Fibronectin and High Cell Density," The Journal of Cell Biology, vol. 96, pp. 462-473, Feb. 1983.

Lander et al. "Laminin is associated with the 'nuerite outgrowth-promotion factors' found in conditioned media," Proc. Natl. Acad. Sci. USA, vol. 82, pp. 2183-2187, Apr. 1985.

Fraser et al. "A monoclonal antibody against a laminin-heparan sulfae proteoglycan complex perturbs cranial neural crest migration in vivo," The Journal of Cell Biology, vol. 106, pp. 1321-1329, Apr. 1988.

Kleinman et al. "Formation of a Supramolecular Complex Is Involved the Reconstitution of Basement Membrane Composets," Biochemistry, vol. 22, p. 4969-4974, 1983.

Engvall et al. "Mapping of Domains in Human Laminin Using Monoclonal Antibodies: Localiztion of the Neurite-promotion Site," The Journal of Cell Biology, vol. 103, No. 6, Pt. 1, pp. 2457-2465, 1986.

Liesi et al. "Laminin is induced in astrocytes of adult brain by injury," The EMBO Journal, vol. 3, No. 3, pp. 683-686, 1984.

Terranova et al. "Role of laminin in the attachment of PAM 212 (epithelial) Cells to Basement Membrane Collagen," Cell, vol. 22, pp. 719-726, Dec. 1980.

Rao et al. "Binding domain for laminin of type IV collagen," Biochemical and biophysical research communications, vol. 128, No. 1, Apr. 16, 1985.

Charonis et al. "Binding of laminin to type IV collagen: A morphological study," The Journal of Cell Biology, vol. 100, pp. 1848-1853, 1985.

Laurie et al. "Localization of Binding Sites for Laminin, Heparan Sulfate Proteoglycan and Fibronectin on Basement Membrane (Tyoe IV) Collagen," J. Mol. Biol., vol. 189, pp. 205-216, 1986.

Riopelle et al. Functional interactions of neuronal heparan sulphate preoteoglycans with laminin, Brain Research, vol. 525, pp. 92-100, 1990.

Battaglia et al. "Basement-membrane heparan sulfate proteoglycan binds to laminin by its heparan sulfate chains and to nidogen by sites in the protein core," Eur. J. Biochem., vol. 208, pp. 359-366, 1992.

Sakashita et al. "Basement membrane glycoprotein laminin binds to heparin," FEBS letters, vol. 116, No. 2, Jul. 1980.

Del Rosso et al. "Binding of the basement-membrane glycoprotein laminin to glycosaminoglycans," Biochem. J., vol. 199, pp. 699-704, 1981.

Skubitz et al. "Localization of three distinct heparin-hinding Domains of Laminin by Monoclonal antibodies," The Journal of biological chemistry, vol. 263, No. 10, pp. 4861-4868, Apr. 5, 1988.

Hall et al. "The $\alpha_1/\beta_1$ and $\alpha_6/\beta_1$ integrin heterodimers mediate cell attachment to distinct sites on laminin," The Journal of Cell Biology, vol. 110, pp. 2175-2184, Jun. 1990.

Goodman et al. "Multiple cell surface receptors for the short arms of laminin: $\alpha1/\beta1$ integrin and RGD-dependent proteins mediate cell attachment only to domains III in Murine Tumor Laminin," The Journal of Cell Biology, vol. 113, No. 4, pp. 931-941, May 1991.

Yurchenco et al. "Heparin modulation of laminin polymerization," The Journal of Biological chemistry, vol. 265, No. 7, pp. 3981-3991, Mar. 5, 1990.

Fox et al. "Recombinant nidogen consists of three globular domains and mediates binding of laminin to collagen type IV," The EMBO Journal, vol. 10, No. 11, pp. 3137-3146, 1991.

Sung et al. "Cell and Heparin Binding in the Distal Long Arm of Laminin: Identification of Active and Cryptic Sites with Recombinant and Hybrid Glycoprotein," The Journal of Cell Biology, vol. 123, No. 5, pp. 1255-1268, Dec. 1993.

Shimomura et al. "Studies on Macromolecular Components of human glomerular basement membrane and alterations in diabetes," Diabetes. vol. 36, Mar. 1987.

Lyon et al. "Co-deposition of basement membrane components during the induction of murine splenic AA amyloid," Laboratory investigation, vol. 64, No. 6, p. 785, 1991.

Perlmutter et al. "Microangiopathy, the Vascular Basement Membrane and Alzheimer's Disease: A Review," Brian Research Bulletin, vol. 24, pp. 677-686, 1990.

Murtomaki et al. "Laminin and its neurite outgrowth-promotin domain in the brain in alzheimer's disease and down's syndrome patients," Journal of Neuroscience Research, vol. 32, pp. 261-273, 1992.

Perlmutter et al. "Vascular basement membrane component and the lesions of Alzheimer's Disease: light and electron microscopic analyses," Microscopy research technique, vol. 28, pp. 204-215, 1994.

Narindrasorasak et al. "Characterization of high affinity binding between lanimim and Alzheimer's Disease amyloid precursor proteins," Laboratory investigation, vol. 67, No. 5, p. 643, 1992.

Naiki et al. "Kinetic analysis of amyloid fibril polymerization in vitro," Laboratory investigation, vol. 65, No. 1, p. 104, 1991.

Levine et al. "Thioflavine T interaction with synthetic Alzheimer's Disease β-amyloid peptides: detection of amyloid aggregation in solution," Protein Science, vol. 2, pp. 404-410, 1993.

Maiki et al. "First-order kinetic model of Alzheimer's β-amyloid fibril extension in vitro," Laboratory investigation, vol. 74, No. 2, p. 374, 1996.

Westermark et al. "Islet amyloid in type 2 human diabetes mellitus and adult diabitic ats cantains a novel putative polypeptide hormone," American Journal of Pathology, vol. 127, No. 3, Jun. 1987.

Cooper et al. "Purification and characterization of a peptide from amyloid-rich pancreases of type 2 diabetic patients," Proc. Natl. Acad. Sci. USA, vol. 84, pp. 8628-8632, Dec. 1987.

Levine. "Thioflavine T interaction with amyloid β-sheet structures," int. j. exp. clin. invest. vol. 2, pp. 1-6, 1995.

Laemmli. "Cleavage of structural proteins during the assembly of the head of bacteriophage T4," Nature, vol. 227, Aug. 15, 1970.

Schagger et al. "Tricine-sodium dodecyl sulfate-polyacrylamide gel electrophoresis for the separation of proteins i8ng the range from 1 to 100kDa," analytical biochemistry, vol. 166, pp. 368-379, 1987.

Sasaki et al. "The laminin B2 chain has a multidomain structure homologous to the B1 chain," The journal of biological chemistry, vol. 262, No. 35, pp. 17111-17117, Dec. 15, 1987.

Sasaki et al. "Sequence of the cDNA encoding the laminin B1 chain reveals a multidomain protein containing cysteine-rich repeats," Proc. natl. Acad. Sci. USA, vol. 84, pp. 935-939, Feb. 1987.

Durkin et al. "Primary structure of the mouse laminin B2 chain and Comparison with Laminin B1," Biochemistry, vol. 27, pp. 5198-5204, 1988.

Sasaki et al. "Laminin, a multidomain protein," The journal of Biological Chemistry, vol. 263, No. 32, pp. 16536-16544, Nov. 15, 1988.

Colognato et al. "Mapping of Network-forming, heparin-hinding, and α1β1 integrin-recognition sites within the α-chain short arm of Laminin-1," The journal of biological chemistry, vol. 270, No. 16, pp. 9398-9406, Apr. 21, 1995.

Mandybur et al. "Cerebral amyloid angiopathy: the vascular pathology and complications," Journal of Neuropathology and Experimental neurology, vol. 45, No. 1, pp. 79-90, Jan. 1986.

Pardridge et al. "Amyloid angiopathy of Alzheimer's Disease: amino acid composition and partial sequence of a 4,200-dalton peptid isolated from cortical microvessels," Journal of Neurochemistry, vol. 49, No. 5, 1987.

Pike et al. "In vitro aging of β-amyloid protein causes peptide aggregation and neurotoxicity," Brain research, vol. 563, pp. 311-314, 1991.

Pike et al. "Structure-activity analyses of β-amyloid peptides: contributions of the β25-35 region to aggregation and neurotoxicity," Journal of neurochemistry, vol. 64, No. 1, 1995.

Harrigan et al. "Beta amyloid is neurotixic in hippocampal slice cultures," Neurobiology of aging, vol. 16, No. 5, pp. 779-789, 1995.

Games et al. "Alzheimer-type neuropatholofy in transgenic mice overexpressing V717F β-amyloid precursor protein," Nature, vol. 373, Feb. 9, 1995.

Hsiao et al. "Age related CNS disorder and early death in transgenc FVB/N mice overexpressing Alzheimer amyloid precursor proteins," Neuron, vol. 15, pp. 1203-1218, Nov. 1995.

Flood et al. "An amyloid β-protein fragment, Aβ[12-28], equipotently impairs post-training memory processing when inficted into different limbic system structures," Brain research, vol. 663, pp. 271-276, 1994.

Flood et al. "Amnestic effects in mice of four synthetic peptides homologous to amyloid β-protein from patients with Alzheimer's Disease," proc. natl. acad. sci. USA, vol. 88, pp. 3363-3366, Apr. 1991.

Puchtler et al. "On the Binding of Congo Red by Amyloid," [publication data unknown].

Harada et al. "Human amyloid protein: chemical variability and homogeneity," The Journal of histochemistry and cytochemistry, vol. 19, No. 1, 1971.

Metaxas. "Familial mediterranean fever and amyloidosis," Kidney International, vol. 20, pp. 676-685, 1981.

Skinner et al. "The prealbumin nature of the amloid protein in familial amyloid polyneuropathy (Fap) swedish variety," Biochimical and Biophysical Research Communications, vol. 99, No. 4, pp. 1326-1332, 1981.

Saraiva et al. "Amyloid Fibril Protein in Familial Amyloidotic Polyneuropathy Portuguese Type," J. Clin. Invest., vol. 74, pp. 104-119, Jul. 1984.

Saraiva et al. "Studies on plasma trasthyretin (prealbumin) in familial amyloidotic polyneuropathy, portuguese type," J. Lab. Clin. Med., vol. 102, No. 4, Oct. 1983.

Tawara et al. "Amyloid fibril protein in type 1 familial amyloiditic polyneuropathy in Japanese," J. Lab. Clin. Med., vol. 96, No. 6, Dec. 1981.

Jensson et al. "The saga of cystatin C gene mutation cousing amyloid angiopathy and brain hemorrhage-clenical genetics in iceland," Clinical Genetics, vol. 36, pp. 368-377, 1989.

Wright et al. "Relationship of amyloid deposits int eh human aorta to aortic atherosclerosis," Laboratory Investigation, vol. 30, No. 6, p. 767, 1974.

Pitkanen et al. "Senile systemic amyloidosis," AJP, vol. 117, No. 3, Dec. 1984.

Johnson et al. "Biology of disease," Laboratory Investigation, vol. 66, No. 5, p. 522, 1992.

Butler et al. "Immunoreactive calcitonin in amyloid fibrils of medullary carcinoma of the thyroid gland," Arch Pathol Lab Med, vol. 110, Jul. 1986.

Berger et al. "Calcitonin-like immunoireactivity of amyloid fibrils in medullarry thyroid carcinomas," Virchows archiv a pathol anat histopathol, vol. 412, pp. 543-551, 1988.

Gejyo et al. "A new form of amyloid protein associated with chronic hemodialysis was identified as $\beta_2$- microglobulin," Biochmical and Biophysical Research Communications, vol. 129, No. 3, pp. 701-706, Jun. 28, 1985.

Gejyo et al. "$\beta_2$-microglobulin: a mew form of amyloid protein associated with chronic hemodialysis," Kidney International, vol. 30, pp. 385-390, 1986.

Glenner et al. "Alzheimer's Disease: initial report of the purification and characterization of a novel cerebrovascular amyloid protein," Biochemical and Biophysical Research Communications, vol. 120, No. 3, pp. 885-890, May 16, 1984.

Masters et al. "Amyloid plaque core protein in Alzheimer's Disease and Down Syndrome," Proc. Natl. Acad. Sci. USA vol. 82, pp. 4245-4249, Jun 1985.

Rumble et al. "Amyloid A4 protein and its precursor in down's syndrome and Alzheimer's Disease," The New England Journal of Medicine, vol. 320, No. 22, Jun. 1, 1989.

* cited by examiner

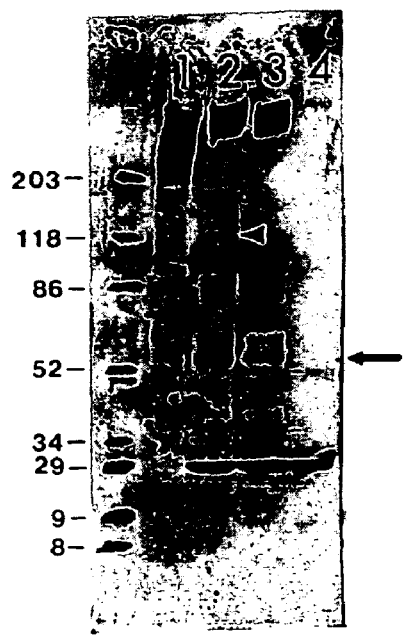
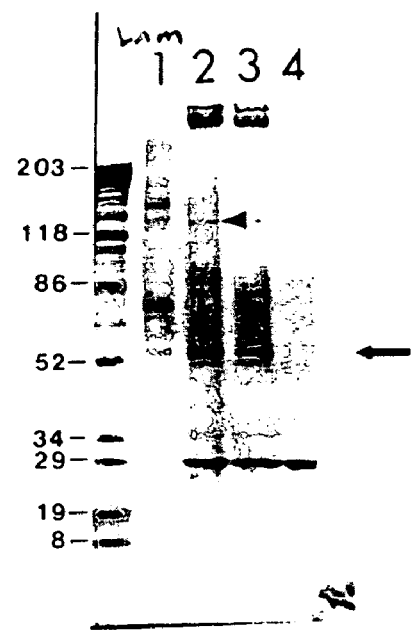
FIGURE 9A
FIGURE 9B

SEQUENCE

```
MRGSGTGAAL LVLLASVLWV TVRSQQRGLF PAILNLATNA HISANATCGE KGPEMFCKLV
EHVPGRPVRH AQCRVCDGNS TNPRERHPIS HAIDGTNNWW QSPSIQNGRE YHWVTVTLDL
RQVFQVAYII IKAANAPRPG NWILERSVDG VKFKPWQYYA VSDTECLTRY KITPRRGPPT
YRADNEVICT SYYSKLVPLE HGEIHTSLIN GRPSADDPSP QLLEFTSARY IRLRLQRIRT
LNADLMTLSH RDLRDLDPIV TRRYYYSIKD ISVGGMCICY GHASSCPWDE EAKQLQCQCE
HNTCGESCDR CCPGYHQQPW RPGTISSGNE CEECNCHNKA KDCYYDSSVA KERRSLNTAG
QYSGGGVCVN CSQNTTGINC ETCIDQYYRP HKVSPYDDHP CRPCNCDPVG SLSSVCIKDD
RHADLANGKW PGQCPCRKGY AGDKCDRCQF GYRGFPNCIP CDCRTVGSLN EDPCIEPCLC
KKNVEGKNCD RCKPGFYNLK ERNPEGCSEC FCFGVSGVCD SLTWSISQVT NMSGWLVTDL
MSTNKIRSQQ DVLGGHRQIS INNTAVMQRL TSTYYWAAPE AYLGNKLTAF GGFLKYTVSY
DIPVETVDSD LMSHADIIIK GNGLTISTRA EGLSLQPYEE YFNVVRLVPE NFRDFNTRRE
IDRDQLMTVL ANVTHLLIRA NYNSAKMALY RLDSVSLDIA SPNAIDLAVA ADVEHCECPQ
GYTGTSCEAC LPGYYRVDGI LFGGICQPCE CHGHASECDI HGICSVCTHN TTGDHCEQCL
PGFYGTPSRG TPGDCQPCAC PLSIDSNNFS PTCHLTDGEE VVCDQCAPGY SGSWCERCAD
GYYGNPTVPG GTCVPCNCSG NVDPLEAGHC DSVTGECLKC LWNTDGAHCE RCADGFYGDA
VTAKNCRACD CHENGSLSGV CHLETGLCDC KPHVTGQQCD QCLSGYYGLD TGLGCVPCNC
SVEGSVSDNC TEEGQCHCGP GVSGKQCDRC SHGFYAFQDG GCTPCDCAHT QNNCDPASGE
CLCPPHTQGL KCEECEEAYW GLDPEQGCQA CNCSAVGSTS AQCDVLSGHC PCKKGFGGQS
CHQCSLGYRS FPDCVPCGCD LRGTLPDTCD LEQGLCSCSE DSGTCSCKEN VVGPQCSKCQ
AGTFALRGDN PQGCSPCFCF GLSQLCSELE GYVRTLITLA SDQPLLHVVS QSNLKGTIEG
VHFQPPDTLL DAEAVRQHIY AEPFYWRLPK QFQGDQLLAY GGKLQYSVAF YSTLGTGTSN
YEPQVLIKGG RARKHVIYMD APAPENGVRQ DYEVQMKEEF WKYFNSVSEK HVTHSDFMSV
LSNIDYILIK ASYGQGLQQS RIANISMEVG RKAVELPAEG EAALLLELCV CPPGTAGHSC
QDCAPGYYRE KLPESGGRGP RPLLAPCVPC NCNNHSDVCD PETGKCLSCR DHTSGDHCEL
CASGYYGKVT GLPGDCTPCT CPHHPPFSFS PTCVVEGDSD FRCNACLPGY EGQYCERCSA
GYHGNPRAAG GSCQTCDCNP QGSVHSDCDR ASGQCVCKPG ATGLHCEKCL PRHILMESDC
VSCDDDCVGP LLNDLDSVGD AVLSLNLTGV SPAPYGILEN LENTTKYFQR YLIKENAKKI
RAEIQLEGIA EQTENLQKEL TRVLARHQKV NAEMERTSNG TQALATFIEQ LHANIKEITE
KVATLNQTAR KDFQPPVSAL QSMHQNISSL LGLIKERNFT EMQQNATLEL KAAKDLLSRI
QKRFQKPQEK LKALKEANSL LSNHSEKLQA AEELLKEAGS KTQESNLLLL LVKANLKEEF
QEKKLRVQEE QNVTSELIAK GREWVDAAGT HTAAAQDTLT QLEHHRDELL LWARKIRSHV
DDLVMQMSKR RARDLVHRAE QHASELQSRA GALDRDLENV RNVSLNATSA AHVHSNIQTL
TEEAEMLAAD AHKTANKTDL ISESLASRGK AVLQRSSRFL KESVGTRRKQ QGITMKLDEL
KNLTSQFQES VDNITKQAND SLAMLRESPG GMREKGRKAR ELAAAANESA VKTLEDVLAL
SLRVFNTSED LSRVNATVQE TNDLLHNSTM TTLLAGRKMK DMEMQANLLL DRLKPLKTLE
ENLSRNLSEI KLLISRARKQ AASIKVAVSA DRDCIRAYQP QTSSTNYNTL ILNVKTQEPD
NLLFYLGSSS SSDFLAVEMR RGKVAFLWDL GSGSTRLEFP EVSINNNRWH SIYITRFGNM
GSLSVKEASA AENPPVRTSK SPGPSKVLDI NNSTLMFVGG LGGQIKKSPA VKVTHFKGCM
GEAFLNGKSI GLWNYIEREG KCNGCFGSSQ NEDSSFHFDG SGYAMVEKTL RPTVTQIVIL
FSTFSPNGLL FYLASNGTKD FLSIELVRGR PLTLMTDRRY NNGTWYKIAF
QRNRKQGLLA VFDAYDTSDK ETKQGETPGA ASDLNRLEKD LIYVGGLPHS KAVRKGVSSR
SYVGCIKNLE ISRSTFDLLR NSYGVRKGCA LEPIQSVSFL RGGYVEMPPK SLSPESSLLA
TFATKNSSGI LLVALGKDAE EAGGAQAHVP FFSIMLLEGR IEVHVNSGDG TSLRKALLHA
PTGSYSDGQE HSISLVRNRR VITIQVDENS PVEMKLGPLT EGKTIDISNL YIGGLPEDKA
TPMLKMRTSF HGCIKNVVLD AQLLDFTHAT GSEQVELDTC LLAAEEPMQSL HREHGELPPE ◄
PPTLPQPELC AVDTAPGYVA GAHQPGLSQN SHLVLPLNQS DVRKRLQVQL SIRTFASSGL
IYYVAHQNQM DYATLQLQEG RLHFMFDLGK GRTKVSHPAL LSDGKWHTVK TEYIKRKAFM
TVDGQESPSV TVVGNATTLD VERKLYLGGL PSHYRARNIG TITHSIPACI GEIMVNGQQL
DKDRPLSASA VDRCYVVAQE GTFFEGSGYA ALVKEGYKVR LDLNITLEFR TTSKNGVLLG
ISSAKVDAIG LEIVDGKVLF HVNNGAGRIT ATYQPRAARA LCDGKWHTLQ AHKSKHRIVL
TVDGNSVRAE SPHTHSTSAD TNDPIYVGGY PAHIKQNCLS SRASFRGCVR NLRLSRGSQV
QSLDLSRAFD LQGVFPHSCP GPEP
```

FIGURE 10

THERAPEUTIC APPLICATIONS OF LAMININ AND LAMININ-DERIVED PROTEIN FRAGMENTS

This is a continuation of U.S. Application Ser. No. 08/947,057 filed Oct. 8, 1997 now abandoned, which claims priority to U.S. Provisional Application No. 60/027,981 filed Oct. 8, 1996.

TECHNICAL FIELD

The invention relates to the discovery, identification and use of laminin, laminin-derived protein fragments, and laminin-derived polypeptides, as well as related peptides and antibodies, for the therapeutic intervention and diagnosis of Alzheimer's disease and other amyloidoses. In addition, the discovery and identification of an Alzheimer's beta-amyloid protein (Aβ) specific binding region within the globular domain repeats of the laminin A chain, has led to new diagnostic and therapeutic applications for Alzheimer's disease and other amyloidoses which are disclosed.

BACKGROUND OF THE INVENTION

Alzheimer's disease is characterized by the accumulation of a 39-43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence now implicates amyloid as a major causative factor of Alzheimer's disease pathogenesis. Discovery and identification of new compounds, agents, proteins, polypeptides or protein-derivatives as potential therapeutic agents to arrest Alzheimer's disease Aβ amyloid formation, deposition, accumulation and/or persistence is desperately sought.

It is known that Aβ is normally present in human blood and cerebrospinal fluid. However, it is not known why this potential fibrillar protein remains soluble in circulating biological fluids. Can the agent(s) responsible for this extraordinary solubility of fibrillar Aβ be applied to diagnostic and therapeutic regimens against the fibrillar Aβ amyloid present in Alzheimer's brain?

SUMMARY OF THE INVENTION

The present invention provides answers to these questions and relates to the novel and surprising discovery that laminin and specific laminin-derived protein fragments are indeed potent inhibitors of Alzheimer's disease amyloidosis, and therefore have potential use for the therapeutic intervention and diagnosis of the amyloidoses. In addition, we have identified a specific region within laminin which interacts with the Alzheimer's disease beta-amyloid protein and contributes to the observed inhibitory and therapeutic effects. In addition, specific laminin-derived protein fragments which also interact with the Aβ of Alzheimer's disease have been discovered to be present in human serum and cerebrospinal fluid, and implicate diagnostic applications which are described.

Laminin is a specific basement membrane component that is involved in several fundamental biological processes, and may play important roles in the pathogenesis of a number of different human diseases. Using a solid phase binding immunoassay, the present invention determined that laminin binds the Aβ of Alzheimer's disease with a single binding constant of $K_d = 2.7 \times 10^{-9}$ M. In addition, using a Thioflavin T fluorometry assay (which quantitatively determines the amount of fibrillar amyloid formed), the present invention has determined that laminin is surprisingly an extremely potent inhibitor of Aβ fibril formation. In this latter study, 25 μM of Aβ (residues 1-40) was incubated at 37° C. for 1 week in the presence or absence of 100 nM laminin. Laminin was found to significantly (p<0.001) inhibit Aβ (1-40) amyloid fibril formation by 2.9-fold at 1 hour, 4.6-fold at 1 day, 30.6-fold at 3 days and 27.1-fold at 1 week. Other basement membrane components including perlecan, fibronectin and type IV collagen were not effective inhibitors of Aβ (1-40) fibrillogenesis in comparison to laminin, demonstrating the specificity of the inhibitory effect exhibited by laminin. The inhibitory effects of laminin on Aβ fibrillogenesis was also found to occur in a dose-dependent manner. In addition, laminin was found to cause dissolution of pre-formed Alzheimer's disease amyloid fibrils in a dose-dependent manner following 4 days of incubation. Laminin was digested with V8, trypsin or elastase to determine small protease-resistant fragments of laminin which still interacted with Aβ. A ~55 kilodalton (kDa) laminin fragment derived from V8 or elastase digested laminin was found to interact with biotinylated Aβ (1-40). Amino acid sequencing of the ~55 kDa fragment identified an Aβ-binding domain within laminin situated within the globular repeats of the laminin A chain.

Intact laminin was found to be present in human serum but not human cerebrospinal fluid, whereas laminin protein fragments ranging from ~120 kDa to ~200 kDa were found to be present in both human serum and cerebrospinal fluid. Of all the laminin protein fragments present in human biological fluids described above, a prominent ~130 kilodalton band was found in human serum and cerebrospinal fluid which primarily interacted with Aβ as determined by ligand blotting methodology. This ~130 kilodalton laminin fragment is known as the E8 fragment (i.e. generated following elastase digestion of laminin)(Yurchenco and Cheng, *J. Biol. Chem.* 268:17286-17299, 1993) and is also believed to consist of the globular domains of the laminin A chain. The interaction of specific laminin fragments such as the newly discovered ~130 kDa protein is believed to bind Aβ in biological fluids and keep it in a soluble state. The present invention describes the use of laminin, laminin-derived protein fragments, and laminin-derived polypeptides for the therapeutic intervention and diagnosis of Alzheimer's disease and other amyloidoses. In addition, the discovery and identification of a specific Alzheimer's Aβ-binding region within the globular domain repeats of the laminin A chain, and the discovery of the presence of laminin fragments containing this region in human serum and cerebrospinal fluid, has led to new diagnostic and therapeutic applications for Alzheimer's disease and other amyloidoses.

FEATURES OF THE INVENTION

A primary object of the present invention is to establish new therapeutic methods and diagnostic applications for the amyloid diseases. The amyloid diseases include, but are not limited to, the amyloid associated with Alzheimer's disease and Down's syndrome (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

A primary object of the present invention is to use laminin, laminin-derived protein fragments and/or laminin-derived polypeptides as potent inhibitors of amyloid formation, deposition, accumulation and/or persistence in Alzheimer's disease and other amyloidoses. "Laminin fragments, laminin-derived fragments, laminin-derived protein fragments and/or laminin-derived polypeptides", may include, but are not limited to, laminin A (or A1) chain, laminin B1 chain, laminin B2 chain, laminin A2 chain (merosin), laminin G1 chain, the globular domain repeats within the laminin A1 chain, SEQ ID NO: 1 (11 amino acid sequence within the mouse laminin A chain), SEQ ID NO: 2 (fourth globular repeat with the mouse laminin A chain), SEQ ID NO: 3 (fourth globular repeat within the human laminin A chain), SEQ ID NO: 4 (mouse laminin A chain), SEQ ID NO: 5 (human laminin A chain), SEQ ID NO: 6 (human laminin B1 chain), SEQ ID NO: 7 (mouse laminin B1 chain), SEQ ID NO: 8 (rat laminin B2 chain), SEQ ID NO: 9 (human laminin B2 chain), SEQ ID NO: 10 (mouse laminin G1 chain), SEQ ID NO: 11 (human laminin G1 chain), and all fragments or combinations thereof.

Yet another object of the present invention is to use conformational dependent proteins, polypeptides, or fragments thereof for the treatment of Alzheimer's disease and other amyloidoses. Such conformational dependent proteins include, but are not limited to, laminin, laminin-derived fragments including laminin A1 chain (SEQ ID NO 4; SEQ ID NO: 5), the globular repeat domains within the laminin A1 chain (SEQ ID NO: 2, SEQ ID NO:3), an 11- amino acid peptide sequence within the globular domain of the laminin A chain (SEQ ID NO:1), laminin B1 chain (SEQ ID NO:6, SEQ ID NO: 7), laminin B2 chain (SEQ ID NO: 8, SEQ ID NO:9), laminin G1 chain (SEQ ID NO: 10, SEQ ID NO: 11) and/or portions thereof.

Yet another aspect of the present invention is to use peptidomimetic compounds modelled from laminin, laminin-derived protein fragments and/or laminin-derived polypeptides, including but not limited to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as potent inhibitors of amyloid formation, deposition, accumulation and/or persistence in Alzheimer's disease and other amyloidoses.

Yet another object of the present invention is to mimic the 3-dimensional Aβ-binding site(s) on laminin, laminin-derived protein fragments and/or laminin-derived polypeptides and use these mimics as potent inhibitors of amyloid formation, deposition, accumulation and/or persistence in Alzheimer's disease and other amyloidoses.

Yet a further aspect of the present invention is to use anti-idiotypic antibodies to laminin, laminin-derived protein fragments and/or laminin-derived polypeptides as potent inhibitors of amyloid formation, deposition, accumulation and/or persistence in Alzheimer's disease and other amyloidoses.

Another aspect of the invention is to provide new and novel polyclonal and/or monoclonal peptide antibodies which can be utilized in a number of in vitro assays to specifically detect Aβ-binding laminin derived protein fragments and/or Aβ-binding laminin derived polypeptides in human tissues and/or biological fluids. Polyclonal or monoclonal antibodies that are made specifically against a peptide portion or fragment of laminin which interacts with Aβ can be utilized to detect and quantify amyloid disease specific laminin fragments in human tissues and/or biological fluids. These antibodies can be made by administering the peptides in antigenic form to a suitable host. Polyclonal or monoclonal antibodies may be prepared by standard techniques known to those skilled in the art.

Another object of the present invention is to use laminin, the Aβ-binding laminin fragments and/or laminin-derived polypeptides referred to above, for the detection and specific localization of laminin peptides important in the amyloid diseases in human tissues, cells, and/or cell culture using standard immunohistochemical techniques.

Yet another aspect of the present invention is to use antibodies recognizing laminin, any of the Aβ-binding laminin fragments, and/or laminin-derived polypeptides including, but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, for in vivo labelling; for example, with a radionucleotide, for radioimaging to be utilized for in vivo diagnosis, and/or for in vitro diagnosis.

Yet another aspect of the present invention is to make use of laminin, Aβ-binding laminin protein fragments and/or Aβ-binding laminin-derived polypeptides including, but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as potential therapeutics to inhibit the deposition, formation, and accumulation of fibrillar amyloid in Alzheimer's disease and other amyloidoses (described above), and to enhance the clearance and/or removal of preformed amyloid deposits in brain (for Alzheimer's disease and Down's syndrome amyloidosis) and in systemic organs (for systemic amyloidoses).

Another object of the present invention is to use Aβ-binding laminin-derived polypeptides or fragments thereof, in conjunction with polyclonal and/or monoclonal antibodies generated against these peptide fragments, using in vitro assays to detect amyloid disease specific autoantibodies in human biological fluids. Specific assay systems can be utilized to not only detect the presence of autoantibodies against Aβ-binding laminin-derived protein fragments or polypeptides thereof in biological fluids, but also to monitor the progression of disease by following elevation or diminution of laminin protein fragments and/or laminin-derived polypeptide autoantibody levels.

Another aspect of the invention is to utilize laminin, laminin-derived protein fragments and/or laminin-derived polypeptide antibodies and/or molecular biology probes for the detection of these laminin derivatives in human tissues in the amyloid diseases.

Yet another object of the present invention is to use the laminin-derived protein fragments of the present invention in each of the various therapeutic and diagnostic applications described above. The laminin-derived protein fragments include, but are not limited to, the laminin A1 chain, the globular repeats within the laminin A1 chain, the laminin B1 chain, the laminin B2 chain, the laminin G1 chain, the laminin A2 chain (also known as merosin), and all constituents or variations thereof, including but not limited to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, including peptides which have at least 70% homology to the sequences disclosed herein. Specific laminin-derived protein fragments or peptides as described above may be derived from any species including, but are not limited to, human, murine, bovine, porcine, and/or equine species.

Another object of the invention is to provide polyclonal and/or monoclonal peptide antibodies which can be utilized in a number of in vitro assays to specifically detect laminin protein fragments in human tissues and/or biological fluids. Polyclonal or monoclonal antibodies made specifically against a peptide portion or fragment of any of the laminin fragments described herein can be utilized to detect and quantify laminin-derived protein fragments in human tissues and/or biological fluids. A preferred embodiment is a polyclonal antibody made to the ~130 kilodalton Aβ-binding laminin fragment present in human serum and cerebrospinal fluid. These antibodies can be made by isolating and administering the laminin-derived fragments and/or polypeptides in antigenic form to a suitable host. Polyclonal or monoclonal antibodies may be prepared by standard techniques by one skilled in the art.

Yet another object of the present invention is to use laminin-derived fragment antibodies as described herein as a specific indicator for the presence and extent of laminin breakdown in brain by monitoring biological fluids including, but not limited to, cerebrospinal fluid, blood, serum, urine, saliva, sputum, and stool.

Yet another object of the present invention is to use laminin-derived fragment antibodies as described herein as a specific indicator for the presence, extent and/or progression of Alzheimer's disease and/or other brain amyloidoses by monitoring biological fluids including, but not limited to, cerebrospinal fluid, blood, serum, urine, saliva, sputum, and stool.

Yet another object of the present invention is to use laminin-derived fragment antibodies as described herein as a specific indicator for the presence and extent of laminin breakdown in systemic organs by monitoring biological fluids including, but not limited to, cerebrospinal fluid, blood, serum, urine, saliva, sputum, and stool.

Yet another object of the present invention is to use laminin-derived fragment antibodies as described herein as a specific indicator for the presence and extent of amyloidosis in type II diabetes by monitoring biological fluids including, but not limited to, cerebrospinal fluid, blood, serum, urine, saliva, sputum, and stool.

Yet another object of the present invention is to use laminin-derived fragment antibodies as described herein as a specific indicator for the presence and extent of amyloidosis in other systemic amyloidoses by monitoring biological fluids including, but not limited to, cerebrospinal fluid, blood, serum, urine, saliva, sputum, and stool.

Yet another object of the present invention is to make use of peptides or fragments of laminin as described herein, including but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as potential blocking therapeutics for the interaction of laminin and laminin-derived fragments in a number of biological processes and diseases (such as in Alzheimer's disease and other amyloid diseases described herein).

Yet another object of the invention is to utilize specific laminin-derived fragment antibodies, as described herein, for the detection of these laminin fragments in human tissues in the amyloid diseases.

Another object of the present invention is to use laminin, laminin-derived protein fragments, and laminin-derived polypeptides, as described herein, for the treatment of amyloid formation, deposition, accumulation and/or persistence in Alzheimer's disease and other amyloidoses.

Another object of the present invention is to use pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, and sterile packaged powders, which contain laminin, laminin-derived protein fragments, and laminin-derived polypeptides, including, but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, to treat patients with Alzheimer's disease and other amyloidoses.

Yet another object of the present invention is to use laminin, laminin-derived protein fragments, and laminin-derived polypeptides, including, but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as potent agents which inhibit amyloid formation, amyloid deposition, amyloid accumulation, amyloid persistence, and/or cause a dissolution of pre-formed or pre-deposited amyloid fibrils in Alzheimer's disease, and other amyloidoses.

Yet another object of the present invention is to provide the use of laminin, laminin-derived protein fragments, and laminin-derived polypeptides, as described herein, for inhibition of amyloid formation, deposition, accumulation, and/or persistence, regardless of its clinical setting.

Yet another object of the present invention is to provide compositions and methods involving administering to a subject a therapeutic dose of laminin, laminin-derived protein fragments, and laminin-derived polypeptides, which inhibit amyloid deposition, including but not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof. Accordingly, the compositions and methods of the invention are useful for inhibiting amyloidosis in disorders in which amyloid deposition occurs. The proteins or polypeptides of the invention can be used therapeutically to treat amyloidosis or can be used prophylactically in a subject susceptible to amyloidosis. The methods of the invention are based, at least in part, in directly inhibiting amyloid fibril formation, and/or causing dissolution of pre-formed amyloid fibrils.

Yet another object of the present invention is to provide pharmaceutical compositions for treating amyloidosis. The pharmaceutical compositions include a therapeutic compound of the invention in an amount effective to inhibit amyloid deposition and a pharmaceutically acceptable vehicle.

These and other features and advantages of the present invention will become more fully apparent when the following detailed description of the invention is read in conjunction with the accompanying figures.

BRIEF DESCRIPTION OF THE DRAWINGS

The following drawings are illustrative of embodiments of the invention and are not meant to limit the scope of the invention.

FIGS. 9A & 9B are black and white photographs of laminin digested with elastase, separated by SDS-PAGE and following interaction with biotinylated Aβ(1-40). A ~55 kilodalton laminin fragment (arrow) that binds biotinylated Aβ was identified and sequenced. Note also the presence of a ~130 kDa fragment (arrowheads) that binds Aβ following 1.5 hours of elastase digestion (lane 2). FIG. 9A is a ligand blot using biotinylated Aβ as a probe, whereas FIG. 9B is Coomassie blue staining of the same blot in FIG. 9A to locate the specific band(s) for sequencing.

FIG. 10 (SEQ. ID NO: 12) shows the complete amino acid sequence of the mouse laminin A chain. Sequencing of the ~55 kilodalton Aβ-binding band shown in FIGS. 9A & 9B leads to the identification of an 11 amino acid segment (underline and arrowhead) within the laminin A chain. This Aβ binding region of laminin is situated within the globular domain repeats of the laminin A chain.

DETAILED DESCRIPTION OF THE INVENTION

Figure 1:
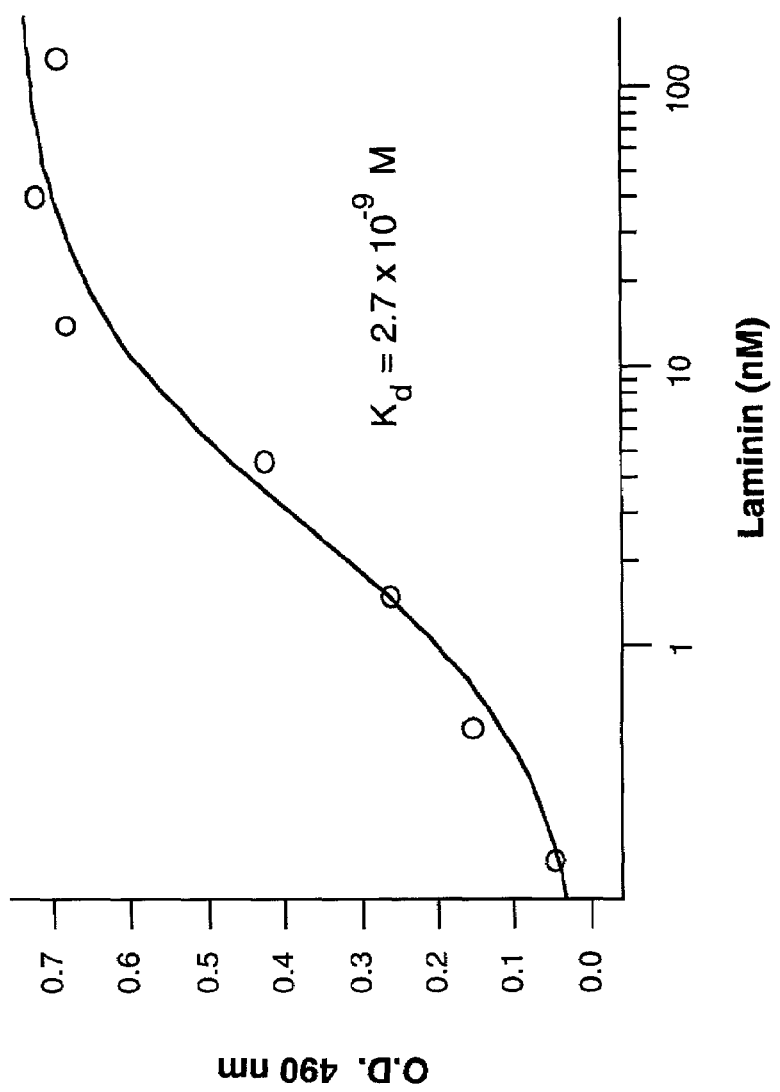
FIG. 1 is a binding curve demonstrating the binding interaction of EHS laminin to substrate bound Aβ (1-40). A single binding site with a $K_d=2.7\times10^{-9}$ M is determined.

The following sections are provided by way of background to better appreciate the invention.

Alzheimer's Disease

Alzheimer's disease is the most common cause of dementia in middle and late life, and is manifested by progressive impairment of memory, language, visuospatial perceptions and behavior (*A Guide to the Understanding of Alzheimer's Disease and Related Disorders*, edited by Jorm, New York University Press, New York 1987). A diagnosis of probable Alzheimer's disease can be made on clinical criteria (usually by the exclusion of other diseases, memory tests etc), but a definite diagnosis requires the histological examination of specific abnormalities in the brain tissue usually obtained at autopsy.

In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al, *Proc. Natl. Acad. Sci. USA* 82:4245-4249, 1985; Husby et al, *Bull. WHO* 71:105-108, 1993). Aβ is derived from larger precursor proteins termed beta-amyloid precursor proteins (or βPPs) of which there are several alternatively spliced variants. The most abundant forms of the βPPs include proteins consisting of 695, 751 and 770 amino acids (Tanzi et al, *Nature* 331:528-530, 1988; Kitaguchi et al, *Nature* 331:530-532, 1988; Ponte, et al, *Nature* 331:525-528, 1988). The small Aβ peptide is a major component which makes up the amyloid deposits of neuritic "plaques" and in the walls of blood vessels (known as cerebrovascular amyloid deposits) in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913-4917, 1986; Kosik et al, *Proc. Natl. Acad. Sci. USA* 83:4044-4048, 1986; Lee et al, *Science* 251:675-678, 1991). The pathological hallmarks of Alzheimer's disease is therefore the presence of "plaques" and "tangles", with amyloid being deposited in the central core of plaques and within the blood vessel walls. It is important to note that a so-called "normal aged brain" has some amyloid plaques and neurofibrillary tangles present. However, in comparison, an Alzheimer's disease brain shows an over abundance of plaques and tangles. Therefore, differentiation of an Alzheimer's disease brain from a normal brain from a diagnostic point of view is primarily based on quantitative assessment of "plaques" and "tangles".

In an Alzheimer's disease brain, there are usually thousands of neuritic plaques. The neuritic plaques are made up of extracellular deposits consisting of an amyloid core usually surrounded by enlarged axons and synaptic terminals, known as neurites, and abnormal dendritic processes, as well as variable numbers of infiltrating microglia and surrounding astrocytes. The neurofibrillary tangles present in the Alzheimer's disease brain mainly consist of tau protein, which is a microtubule-associated protein (Grundke-Iqbal et al, *Proc. Natl. Acad. Sci. USA* 83:4913-4917, 1986; Kosik et al, *Proc. Natl. Acad. Sci. USA* 83:4044-4048, 1986; Lee et al, *Science* 251:675-678, 1991). At the ultrastructural level, the tangle consists of paired helical filaments twisting like a ribbon, with a specific crossing over periodicity of 80 nanometers. In many instances within a neurofibrillary tangle, there are both paired helical filaments and straight filaments. In addition, the nerve cells will many times die, leaving the filaments behind. These tangles are known as "ghost tangles" since they are the filamentous remnants of the dead neuron.

The other major type of lesion found in the brain of an Alzheimer's disease patient is the accumulation of amyloid in the walls of blood vessels, both within the brain parenchyma and in the walls of the larger meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al, *J. Neurochem.* 49:1394-1401, 1987).

In addition, Alzheimer's disease patients demonstrate neuronal loss and synaptic loss. Furthermore, these patients also exhibit loss of neurotransmitters such as acetylcholine. Tacrine, the first FDA approved drug for Alzheimer's disease is a cholinesterase inhibitor (Cutler and Sramek, *New Engl. J. Med.* 328:808-810, 1993). However, this drug has showed limited success, if any, in the cognitive improvement in Alzheimer's disease patients and initially had major side effects such as liver toxicity.

For many years there has been an ongoing scientific debate as to the importance of "amyloid" in Alzheimer's disease and whether the "plaques" and "tangles" characteristic of this disease, were a cause or merely the consequences of the disease. Recent studies during the last few years have now implicated that amyloid is indeed a causative factor for Alzheimer's disease and not merely an innocent bystander. The Alzheimer's disease Aβ protein in cell culture has been shown to cause degeneration of nerve cells within short periods of time (Pike et al, *Br. Res.* 563:311-314, 1991; *J. Neurochem.* 64:253-265, 1994). Studies suggest that it is the fibrillar structure, a characteristic of all amyloids, that is responsible for the neurotoxic effects. The Aβ has also been found to be neurotoxic in slice cultures of hippocampus (the major memory region affected in Alzheimer's)(Harrigan et al, *Neurobiol. Aging* 16:779-789, 1995) and induces nerve cell death in transgenic mice (Games et al, *Nature* 373:523-527, 1995; Hsiao et al, *Neuron* 15:1203-1218, 1995). In addition, injection of the Alzheimer's Aβ into rat brain causes memory impairment and neuronal dysfunction (Flood et al, *Proc. Natl. Acad. Sci. U.S.A.* 88:3363-3366, 1991; *Br. Res.* 663:271-276, 1994), two additional hallmarks of Alzheimer's disease. Probably, the most convincing evidence that amyloid (ie. beta-amyloid protein) is directly involved in the pathogenesis of Alzheimer's disease comes from genetic studies. It has been discovered that the production of Aβ can result from mutations in the gene encoding, its precursor, known as the beta-amyloid precursor protein (Van Broeckhoven et al, *Science* 248:1120-1122, 1990; *Europ. Neurol.* 35:8-19, 1995; Murrell et al, *Science* 254:97-99, 1991; Haass et al, *Nature Med.* 1:1291-1296, 1995). This precursor protein when normally processed usually only produces very little of the toxic Aβ. The identification of mutations in the amyloid precursor protein gene which causes familial, early onset Alzheimer's disease is the strongest argument that amyloid is central to the pathogenetic process underlying this disease. Four reported disease-causing mutations have now been discovered which demonstrate the importance of the beta-amyloid protein in causing familial Alzheimer's disease (reviewed in Hardy, *Nature Genet.* 1:233-234, 1992). All of these studies suggest that providing a drug to reduce, eliminate or prevent fibrillar Aβ formation, deposition, accumulation and/or persistence in the brains of human patients should be considered an effective therapeutic.

Other Amyloid Diseases

The "amyloid diseases" consist of a group of clinically and generally unrelated human diseases which all demonstrate a marked accumulation in tissues of an insoluble extracellular substance known as "amyloid", and usually in an amount sufficient to impair normal organ function. Rokitansky in 1842 (Rokitansky, "*Handbuch der pathologischen Anatomie*", Vol. 3, Braumuller and Seidel, Vienna) was the first to observe waxy and amorphous looking tissue deposits in a number of tissues from different patients. However, it wasn't until 1854 when Virchow (Virchow, *Arch. Path. Anat.* 8:416, 1854) termed these deposits as "amyloid" meaning "starch-like" since they gave a positive staining with the sulfuric acid-iodine reaction, which was used in the 1850's for demonstrating cellulose. Although cellulose is not a constituent of amyloid, nonetheless, the staining that Virchow observed was probably due to the present of proteoglycans (PGs) which appear to be associated with all types of amyloid deposits. The name amyloid has remained despite the fact that Friederich and Kekule in 1859 discovered the protein nature of amyloid (Friedrich and Kekule, *Arch. Path. Anat. Physiol.* 16:50, 1859). For many years, based on the fact that all amyloids have the same staining and structural properties, lead to the postulate that a single pathogenetic mechanism was involved in amyloid deposition, and that amyloid deposits were thought to be composed of a single set of constituents. Current research has clearly shown that amyloid is not a uniform deposit and that amyloids may consist of different proteins which are totally unrelated (Glenner, *N. England J. Med.* 302:1283-1292, 1980).

Although the nature of the amyloid itself has been found to consist of completely different and unrelated proteins, all amyloids appear similar when viewed under the microscope due to amyloid's underlying protein able to adapt into a fibrillar structure. All amyloids regardless of the nature of the underlying protein 1) stain characteristically with the Congo red dye and display a classic red/green birefringence when viewed under polarized light (Puchtler et al, *J. Histochem. Cytochem.* 10:355-364, 1962), 2) ultrastructurally consists of fibrils with a diameter of 7-10 nanometers and of indefinite length, 3) adopt a predominant beta-pleated sheet secondary structure. Thus, amyloid fibrils viewed under an electron microscope (30,000 times magnification) from the post-mortem brain of an Alzheimer's disease patient would look nearly identical to the appearance of amyloid present in a biopsied kidney from a rheumatoid arthritic patient. Both these amyloids would demonstrate a similar fibril diameter of 7-10 nanometers.

In the mid to late 1970's amyloid was clinically classified into 4 groups, primary amyloid, secondary amyloid, familial amyloid and isolated amyloid. Primary amyloid, is amyloid appearing de novo, without any preceding disorder. In 25-40% of these cases, primary amyloid was the antecedent of plasma cell dysfunction such as the development of multiple myeloma or other B-cell type malignancies. Here the amyloid appears before rather than after the overt malignancy. Secondary amyloid, appeared as a complication of a previously existing disorder. 10-15% of patients with multiple myeloma eventually develop amyloid (Hanada et al, *J. Histochem. Cytochem.* 19:1-15, 1971). Patients with rheumatoid arthritis, osteoarthritis, ankylosing spondylitis can develop secondary amyloidosis as with patients with tuberculosis, lung abscesses and osteomyelitis (Benson and Cohen, *Arth. Rheum.* 22:36-42, 1979; Kamei et al, *Acta Path. Jpn.* 32:123-133, 1982; McAdam et al, *Lancet* 2:572-575, 1975). Intravenous drug users who self-administer and who then develop chronic skin abscesses can also develop secondary amyloid (Novick, *Mt. Sin. J. Med.* 46:163-167, 1979). Secondary amyloid is also seen in patients with specific malignancies such as Hodgkin's disease and renal cell carcinoma (Husby et al, *Cancer Res.* 42:1600-1603, 1982). Although these were all initially classified as secondary amyloid, once the amyloid proteins were isolated and sequenced many of these turned out to contain different amyloid proteins.

The familial forms of amyloid also showed no uniformity in terms of the peptide responsible for the amyloid fibril deposited. Several geographic populations have now been identified with genetically inherited forms of amyloid. One group is found in Israel and this disorder is called Familial Mediterranean Fever and is characterized by amyloid deposition, along with recurrent inflammation and high fever (Mataxas, *Kidney* 20:676-685, 1981). Another form of inherited amyloid is Familial Amyloidotic Polyneuropathy, and has been found in Swedish (Skinner and Cohen, *Biochem. Biophys. Res. Comm.* 99:1326-1332, 1981), Portuguese (Saraiva et al, *J. Lab. Clin. Med.* 102:590-603, 1983; *J. Clin. Invest.* 74:104-119, 1984) and Japanese (Tawara et al, *J. Lab. Clin. Med.* 98:811-822, 1981) nationalities. Amyloid deposition in this disease occurs predominantly in the peripheral and autonomic nerves. Hereditary amyloid angiopathy of Icelandic origin is an autosomal dominant form of amyloid deposition primarily affecting the vessels in the brain, and has been identified in a group of families found in Western Iceland (Jennson et al, *Clin. Genet.* 36:368-377, 1989). These patients clinically have massive cerebral hemorrhages in early life which usually causes death before the age of 40.

The primary, secondary and familial forms of amyloid described above tend to involve many organs of the body including heart, kidney, liver, spleen, gastrointestinal tract, skin, pancreas, and adrenal glands. These amyloid diseases are also referred to as "systemic amyloids" since so many organs within the body demonstrate amyloid accumulation. For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3 to 5 years.

Isolated forms of amyloid, on the other hand, tend to involve a single organ system. Isolated amyloid deposits have been found in the lung, and heart (Wright et al, *Lab. Invest.* 30:767-773, 1974; Pitkanen et al, *Am. J. Path.* 117:391-399, 1984). Up to 90% of type II diabetic patients (non-insulin dependent form of diabetes) have isolated amyloid deposits in the pancreas restricted to the beta cells in the islets of Langerhans (Johnson et al, *New Engl. J. Med.* 321:513-518, 1989; *Lab. Invest.* 66:522-535, 1992). Isolated forms of amyloid have also been found in endocrine tumors which secrete polypeptide hormones such as in medullary carcinoma of the thyroid (Butler and Khan, *Arch. Path. Lab. Med.* 110:647-649, 1986; Berger et al, *Virch. Arch. A Path. Anat. Hist.* 412:543-551, 1988). A serious complication of long term hemodialysis is amyloid deposited in the medial nerve and clinically associated with carpal tunnel syndrome (Gejyo et al, *Biochem. Biophys. Res. Comm.* 129:701-706, 1985; *Kidney Int.* 30:385-390, 1986). By far, the most common type and clinically relevant type of organ-specific amyloid, and amyloid in general, is that found in the brains of patients with Alzheimer's disease (see U.S. Pat. No. 4,666,829 and Glenner and Wong, *Biochem. Biophys. Res. Comm.* 120:885-890, 1984; Masters et al, *Proc. Natl. Acad. Sci.*, USA 82:4245-4249, 1985). In this disorder, amyloid is predominantly restricted to the central nervous system. Similar deposition of amyloid in the brain occurs in Down's syndrome patients once they reach the age of 35 years (Rumble et al, *New England J. Med.* 320:1446-1452, 1989; Mann et al, *Neurobiol. Aging* 10:397-399, 1989). Other types of central nervous system amyloid deposition include rare but highly infectious disorders known as the prion diseases which include Creutzfeldt-Jakob disease, Gerstmann-Straussler syndrome, and kuru (Gajdusek et al, *Science* 197:943-960, 1977; Prusiner et al, *Cell* 38:127-134, 1984; Prusiner, *Scientific American* 251:50-59, 1984; Prusiner et al, *Micr. Sc.* 2:33-39, 1985; Tateishi et al, *Ann. Neurol.* 24:35-40, 1988).

It was misleading to group the various amyloidotic disorders strictly on the basis of their clinical features, since when the major proteins involved were isolated and sequenced, they turned out to be different. For example, amyloid seen in rheumatoid arthritis and osteoarthritis, now known as AA amyloid, was the same amyloid protein identified in patients with the familial form of amyloid known as Familial Mediterranean Fever. Not to confuse the issue, it was decided that the best classification of amyloid should be according to the major protein found, once it was isolated, sequenced and identified.

Thus, amyloid today is classified according to the specific amyloid protein deposited. The amyloid diseases include, but are not limited to, the amyloid associated with Alzheimer's disease, Down's syndrome and hereditary cerebral hemorrhage with amyloidosis of the Dutch type (wherein the specific amyloid is now known as the beta-amyloid protein or Aβ), the amyloid associated with chronic inflammation, various forms of malignancy and Familial Mediterranean Fever (AA amyloid or inflammation-associated amyloidosis), the amyloid associated with multiple myeloma and other B-cell abnormalities (AL amyloid), the amyloid associated with type II diabetes (amylin or islet amyloid), the amyloid associated with the prion diseases including Creutzfeldt-Jakob disease, Gerstmann-Straussler syndrome, kuru and animal scrapie (PrP amyloid), the amyloid associated with long-term hemodialysis and carpal tunnel syndrome ($beta_2$-microglobulin amyloid), the amyloid associated with senile cardiac amyloid and Familial Amyloidotic Polyneuropathy (prealbumin or transthyretin amyloid), and the amyloid associated with endocrine tumors such as medullary carcinoma of the thyroid (variants of procalcitonin).

Laminin and Its Structural Domains

Laminin is a large and complex 850 kDa glycoprotein which normally resides on the basement membrane and is produced by a variety of cells including embryonic, epithelial and tumor cells (Foidart et al, *Lab. Invest.* 42:336-342, 1980; Timpl et al, *Methods Enzymol.* 82:831-838, 1982). Laminin-1 (is derived from the Engelbreth-Holm-Swarm tumor) and is composed of three distinct polypeptide chains, A, B1 and B2 (also referred to as alpha1, β1 and gamma-1, respectively), joined in a multidomain structure possessing three shorts arms and one long arm (Burgeson et al, *Matrix Biol.* 14:209-211, 1994). Each of these arms is subdivided into globular and rodlike domains. Studies involving in vitro self-assembly and the analysis of cell-formed basement membranes have shown that laminin exists as a polymer, forming part of a basement membrane network (Yurchenco et al, *J. Biol. Chem.* 260:7636-7644, 1985; Yurchenco et at, *J. Cell Biol.* 117:1119-1133, 1992; Yurchenco and Cheng, *J. Biol. Chem.* 268: 17286-17299, 1993). Laminin is believed to play important roles in a number of fundamental biological processes including promotion of neural crest migration (Newgreen and Thiery, *Cell Tissue Res.* 211:269-291, 1980; Rovasio et al, *J. Cell Biol.* 96:462-473, 1983), promotion of neurite outgrowth (Lander et al, *Proc. Natl. Acad. Sci.* 82:2183-2187, 1985; Bronner-Fraser and Lallier, *Cell Biol.* 106:1321-1329, 1988), the formation of basement membranes (Kleinman et al, *Biochem.* 22:4969-4974, 1983), the adhesion of cells (Engvall et al, *J. Cell Biol.* 103: 2457-2465, 1986) and is inducible in adult brain astrocytes by injury (Liesi et al, *EMBO J.* 3:683-686, 1984). Laminin interacts with other components including type IV collagen (Terranova et al, *Cell* 22:719-726, 1980; Rao et at, *Biochem. Biophys. Res. Comm.* 128:45-52, 1985; Charonis et at, *J. Cell Biol.* 100: 1848-1853, 1985; Laurie et at, *J. Mol. Biol.* 189:205-216, 1986), heparan sulfate proteoglycans (Riopelle and Dow, *Brain Res.* 525:92-100, 1990; Battaglia et al, *Eur. J. Biochem.* 208:359-366, 1992) and heparin (Sakashita et al, *FEBS Lett.* 116:243-246, 1980; Del Rosso et al, *Biochem. J.* 199:699-704, 1981; Skubitz et al, *J. Biol. Chem.* 263:4861-4868, 1988).

Several of the functions of laminin have been found to be associated with the short arms. First, the short arms have been found to participate in laminin polymerization (Yurchenco et al, *J. Cell Biol.* 117:1119-1133, 1992; Yurchenco and Cheng, *J. Biol. Chem.* 268: 17286-17299, 1993). A recently proposed three-arm interaction hypothesis of laminin polymerization (Yurchenco and Cheng, *J. Biol. Chem.* 268: 17286-17299, 1993) further holds that self-assembly is mediated through the end regions of each of the three short arms. A prediction of this model is that each short arm can independently and competitively inhibit laminin polymerization. However, it has not been possible to formally test this prediction using conventional biochemical techniques because of an inability to separate the alpha and gamma chains. Second, several heparin binding sites have been thought to reside in the short arms (Yurchenco et al, *J. Biol. Chem.* 265:3981-3991, 1990; Skubitz et al, *J. Cell Biol.* 115:1137-1148, 1991), although the location of these sites have remained obscure. Third, the alpha1β1 integrin has been found to selectively interact with large short arm fragments containing all or most of the short arm domains (Hall et al, *J. Cell Biol.* 110:2175-2184, 1990; Goodman et al, *J. Cell Biol.* 113:931-941, 1991).

Most functional activities of laminin appear to be dependent upon the conformational state of the glycoprotein. Specifically, self-assembly and its calcium dependence, nidogen (entactin) binding to laminin, alpha6β1 integrin recognition of the long arm, heparin binding to the proximal G domain (cryptic) and RGD-dependent recognition of the short A chain of laminin (cryptic) have all been found to be conformationally dependent (Yurchenco et al, *J. Biol. Chem.* 260:7636-7644, 1985; Fox et al, *EMBO J.* 10:3137-3146, 1991; Sung et al, *J. Cell Biol.* 123:1255-1268, 1993). Two consequences of improperly folded laminin, loss of normal functional activity and the activation of previously cryptic activities, suggest that it is important to map and characterize biological activities using correctly folded laminin or conformational homologues to any particular laminin or laminin fragment.

Laminin may also be involved in the pathogenesis of a number of important diseases. For example, in diabetes significant decrease in the levels of laminin on the glomerular basement membranes indicates that a molecular imbalance occurs (Shimomura and Spiro, *Diabetes* 36:374-381, 1987). In experimental AA amyloidosis (ie. inflammation-associated amyloidosis), increased levels of laminin are observed at the sites of AA amyloid deposition (Lyon et al, *Lab. Invest.* 64:785-790, 1991). However, the role(s) of laminin in systemic amyloidosis is not known. In Alzheimer's disease and Down's syndrome, laminin is believed to be present in the vicinity of Aβ-containing amyloid plaques (Perlmutter and Chui, *Brain Res. Bull.* 24:677-686, 1990; Murtomaki et al, *J. Neurosc. Res.* 32:261-273, 1992; Perlmutter et al, *Micro. Res. Tech.* 28:204-215, 1994).

Previous studies have indicated that the various isoforms of the beta-amyloid precursor proteins of Alzheimer's disease, bind both the basement membrane proteins perlecan (Narindrasorasak et al, *J. Biol. Chem.* 266:12878-12883, 1991) and laminin (Narindrasorasak et al, *Lab. Invest.* 67:643-652, 1992). With regards to laminin, it was not previously known whether laminin interacts with Aβ, whether a particular domain of laminin (if any) participates in Aβ interactions, and whether laminin had any significant role(s) in Aβ amyloid fibrillogenesis.

The present invention has discovered that laminin binds Aβ with relatively high affinity and surprisingly laminin is a potent inhibitor of Aβ amyloid formation, and causes dissolution of pre-formed Alzheimer's disease amyloid fibrils. In addition, a 55-kilodalton elastase resistent fragment of laminin which also binds Aβ has been localized to the globular domain repeats within the A chain of laminin. This region is believed to be responsible for many of the inhibitory effects that laminin has on Alzheimer's disease amyloidosis. These findings indicate that laminin, laminin-derived protein fragments and/or laminin-derived polypeptides, particularly those containing the disclosed Aβ-binding site within the globular domain repeats within the laminin A chain, may serve as novel inhibitors of Aβ amyloidosis in Alzheimer's disease and other amyloidoses. In addition, the discovery and identification of an Alzheimer's Aβ-binding region within the globular domain repeats of the laminin A chain, and the discovery of its presence in human serum and cerebrospinal fluid, as a ~130 kDa laminin-derived fragment, leads to novel diagnostic and therapeutic applications for Alzheimer's disease and other amyloidoses.

EXAMPLES

The following examples are provided to disclose in detail preferred embodiments of the binding interaction of laminin with Aβ, and the potent inhibitory effects of laminin and disclosed fragments on Aβ fibril formation. However, it should not be construed that the invention is limited to these specific examples.

Example 1

Binding of Laminin to the Beta-Amyloid Protein (Aβ) of Alzheimer's Disease

2 μg of Aβ (1-40)(Bachem Inc., Torrance, Calif. USA; Lot #WM365) in 40 μl of Tris-buffered saline (TBS)(pH 7.0) was allowed to bind overnight at 4° C. to microtiter wells (Nunc plates, Maxisorb). The next day all of the microtiter wells were blocked by incubating with 300 μl of Tris-buffered saline containing 100 mM Tris-HCl, 50 MM NaCl, 0.05% Tween-20, and 3 mM $NaN_3$ (pH 7.4)(TTBS) plus 2% bovine serum albumin (BSA). Various dilutions (ie. 1:10, 1:30, 1:90, 1:270, 1:810, 1:2430 and 1:7290) of Engelbreth-Holm-Swarm (EHS) mouse tumor laminin (1 mg/ml)(Sigma Chemical Co., St. Louis, Mo., USA) in 250 μl of TBS (pH 7.4) were placed in wells (in triplicate) either containing substrate bound Aβ (1-40) or blank, and allowed to bind overnight at 4° C. overnight. The next day, the wells were rinsed 3 times with TTBS, and then probed for 2 hours with 100 μl of rabbit anti-laminin antibody (Sigma Chemical Company, St. Louis, Mo.) diluted 1:10,000 in TTBS. After 3 rinses with TTBS, the wells were then incubated for 2 hours on a rotary shaker with 100 μl of secondary probe consisting of biotinylated goat anti-rabbit (1:1000) and strepavidin-peroxidase (1:500 dilution of a 2 μg/ml solution) in TTBS containing 0.1% BSA. The wells were then rinsed 3 times with TTBS and 100 μl of a substrate solution (OPD-Sigma Fast from Sigma Chemical Co., St. Louis, Mo.) was added to each well and allowed to develop for 10 minutes or until significant color differences were observed. The reaction was stopped with 50 μl of 4N $H_2SO_4$ and read on a Model 450 microplate reader (Biorad, Hercules, Calif. USA) at 490 nm. Data points representing a mean of triplicate determinations were plotted and the affinity constants (ie. $K_d$) were determined using Ultrafit (version 2.1, Biosoft, Cambridge, U.K.) as described below.

The binding data were analyzed assuming a thermodynamic equilibrium for the formation of the complex BL, from the laminin ligand in solution, L, and the uncomplexed Aβ adsorbed to the microtiter well, B, according to the equation: $K_d=[B]\times[L]/[BL]$. We elected to determine $K_d$'s by using an enzyme-linked immunoassay that gives a color signal that is proportional to the amount of unmodified laminin bound to Aβ (Engel, J. and Schalch, W., Mol. Immunol. 17:675-680, 1980; Mann, K. et al, Eur. J. Biochem. 178:71-80, 1988; Fox, J. W. et al, EMBO J. 10:3137-3146, 1991; Battaglia, C. et al, Eur. J. Biochem. 208:359-366, 1992).

To account for potential non-specific binding, control wells without Aβ (in triplicate) were included for each concentration of laminin used in each binding experiment. Optical densities of the control wells never exceeded 0.050 at all laminin concentrations employed for these experiments. The optical densities of the control wells were subtracted from the optical densities of the Aβ-containing wells that received similar laminin concentrations. Non-specific absorbance obtained from Aβ containing wells that did not receive laminin were also subtracted from all data points. Thus, the equation in the form of: $OD_{exp}=OD_o+(S\times[laminin])+(OD_{max}\times[laminin]/([laminin]+K_d)$ where ($S\times[laminin]$) represents non-specific binding (control wells) and $OD_o$ is the non-specific absorbance, becomes $OD_{exp}=OD_{max}\times[laminin]/([laminin]+K_d)$. Therefore, at 50% saturation $OD_{exp}=0.50\ OD_{max}$ and $K_d=[laminin]$. Determination of [laminin] at 50% saturation was performed by non-linear least square program (Ultrafit from Biosoft, UK) using a one-site model.

As demonstrated in FIG. 1, EHS laminin bound immobilized Aβ (1-40) with a single binding constant with an apparent dissociation constant of $K_d=2.7\times10^{-9}$ M. Several repeated experiments utilizing this solid phase binding immunoassay indicated that laminin bound Aβ (1-40) repetitively with one apparent binding constant.

Example 2

Inhibition of Alzheimer's Disease Aβ Fibril Formation by Laminin

The effects of laminin on Aβ fibrillogenesis was also determined using the previously described method of Thioflavin T fluorometry (Naiki et al, Lab. Invest. 65:104-110, 1991; Levine III, Protein Sci. 2:404-410, 1993; Levine III, Int. J. Exp. Clin. Invest. 2:1-6, 1995; Naiki and Nakakuki, Lab. Invest. 74:374-383, 1996). In this assay, Thioflavin T binds specifically to fibrillar amyloid and this binding produces a fluorescence enhancement at 480 nm that is directly proportional to the amount of amyloid fibrils formed (Naiki et al, Lab. Invest. 65:104-110, 1991; Levine III, Protein Sci. 2:404-410, 1993; Levine III, Int. J. Exp. Clin. Invest. 2:1-6, 1995; Naiki and Nakakuki, Lab. Invest. 74:374-383, 1996). In a first study, the effects of EHS laminin on Aβ (1-40) fibrillogenesis was assessed. For this study, 25 μM of freshly solubilized Aβ (1-40)(Bachem Inc., Torrance, Calif., USA; Lot #WM365) was incubated in microcentrifuge tubes at 37° C. for 1 week (in triplicate), either alone, or in the presence of 100 nM EHS laminin (Sigma Chemical Company, St. Louis, Mo., USA) in 100 mM Tris, 50 mM NaCl, pH 7.0 (TBS). 100 nM of laminin utilized for these studies represented a Aβ:laminin molar ratio of 250:1. 50 μl aliquots were then taken from each tube for analysis at 1 hr, 1 day, 3 days, and 1 week. In a second set of studies, the effects of laminin on Aβ (1-40) fibril formation was directly compared to other basement membrane components including fibronectin, type IV collagen and perlecan. For these studies, 25 μM of freshly solubilized Aβ (1-40) was incubated in microcentrifuge tubes for 1 week (in triplicate) either alone, or in the presence of 100 nM of EHS perlecan (isolated as previously described) (Castillo et al, *J. Biochem.* 120:433-444, 1996), fibronectin (Sigma Chemical Company, St. Louis, Mo., USA) or type IV collagen (Sigma Chemical Company, St. Louis, Mo., USA). 50 ul aliquots were then taken for analysis at 1 hour, 1 day, 3 days and 1 week. In a third set of studies, 25 µM of freshly solubilized Aβ (1-40) was incubated in microcentrifuge tubes for 1 week (in triplicate) either alone, or in the presence of increasing concentrations of laminin (i.e. 5 nM, 15 nM, 40 nM and 100 nM). 50 µl aliquots were taken for analysis at 1 hour, 1 day, 3 days and 1 week.

For each determination described above, following each incubation period, Aβ peptides +/− laminin, perlecan, fibronectin or type IV collagen, were added to 1.2 ml of 100 µM Thioflavin T (Sigma Chemical Co., St. Louis, Mo.) in 50 mM phosphate buffer (pH 6.0). Fluorescence emission at 480 nm was measured on a Turner instrument-model 450 fluorometer at an excitation wavelength of 450 nm. For each determination, the fluorometer was calibrated by zeroing in the presence of the Thioflavin T reagent alone, and by seting the 50 ng/ml riboflavin (Sigma Chemical Co., St. Louis, Mo.) in the Thioflavin T reagent to 1800 fluorescence units. All fluorescence determinations were based on these references and any background fluorescence given off by laminin, perlecan, type IV collagen, or fibronectin alone in the presence of the Thioflavin T reagent was always subtracted from all pertinent readings.

Figure 2:
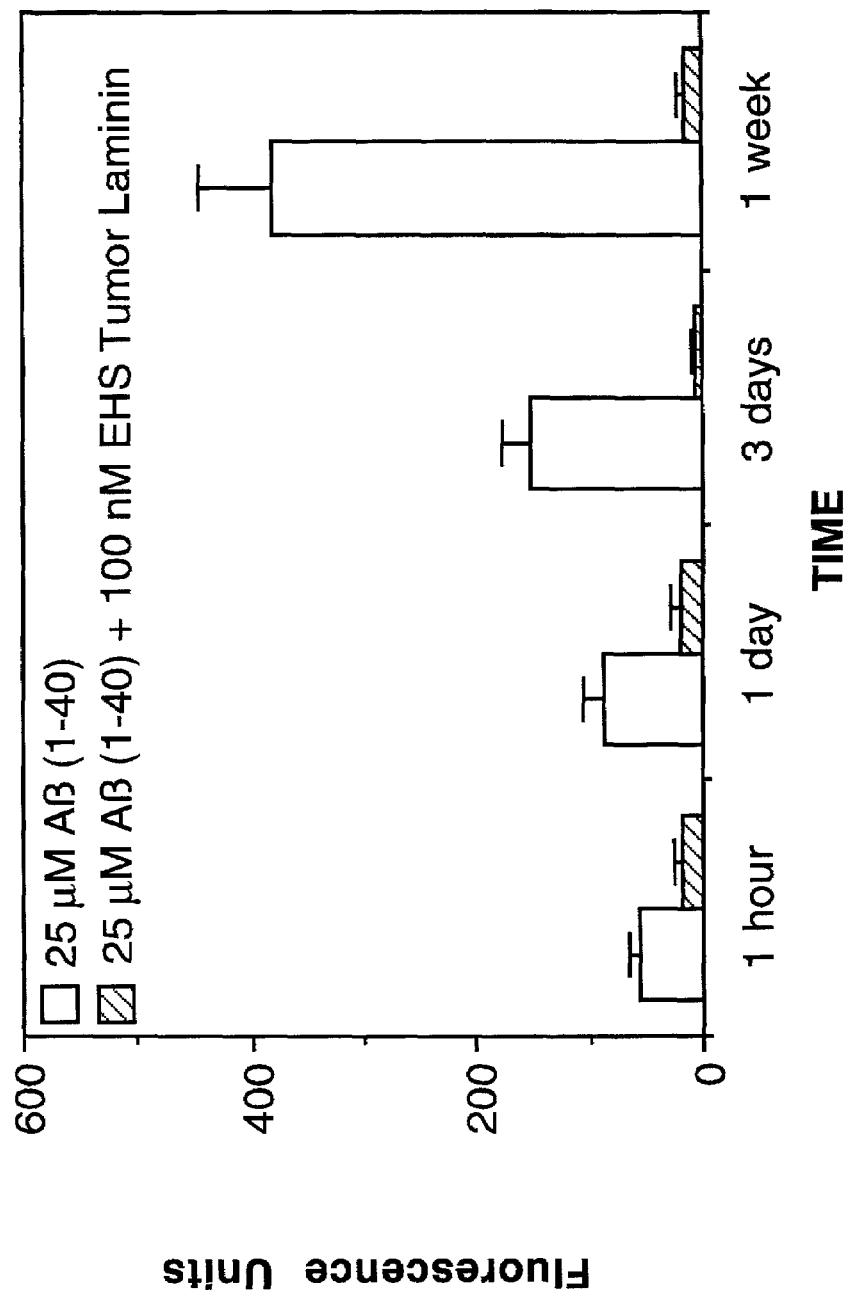
FIG. 2 demonstrates the potent inhibition of Aβ amyloid fibril formation by laminin as determined by a Thioflavin T fluorometry assay over a 1 week experimental period.

As shown in FIG. 2, freshly suspended Aβ (1-40) alone, following a 1 hour incubation at 37° C., demonstrated an initial fluorescence of 41 fluorescence units. During the 1 week incubation period there was a gradual increase in the fluorescence of 25 µM Aβ (1-40) alone, increasing 6.7-fold from 1 hour to 1 week, with a peak fluorescence of 379 fluorescence units observed at 1 week. This increase was significantly inhibited when Aβ (1-40) was co-incubated with laminin, in comparison to Aβ alone. Aβ (1-40) co-incubated with laminin displayed fluorescence values that were 2.9-fold lower ($p<0.001$) at 1 hour, 4.6-fold lower ($p<0.0001$) at 1 day, 30.6-fold lower ($p<0.0001$) at 3 days and 27.1-fold lower ($p<0.0001$) at 1 week. This study indicated that laminin was a potent inhibitor of Aβ amyloid fibril formation, nearly completely inhibiting amyloid fibril formation even after 1 week of incubation.

Figure 3:
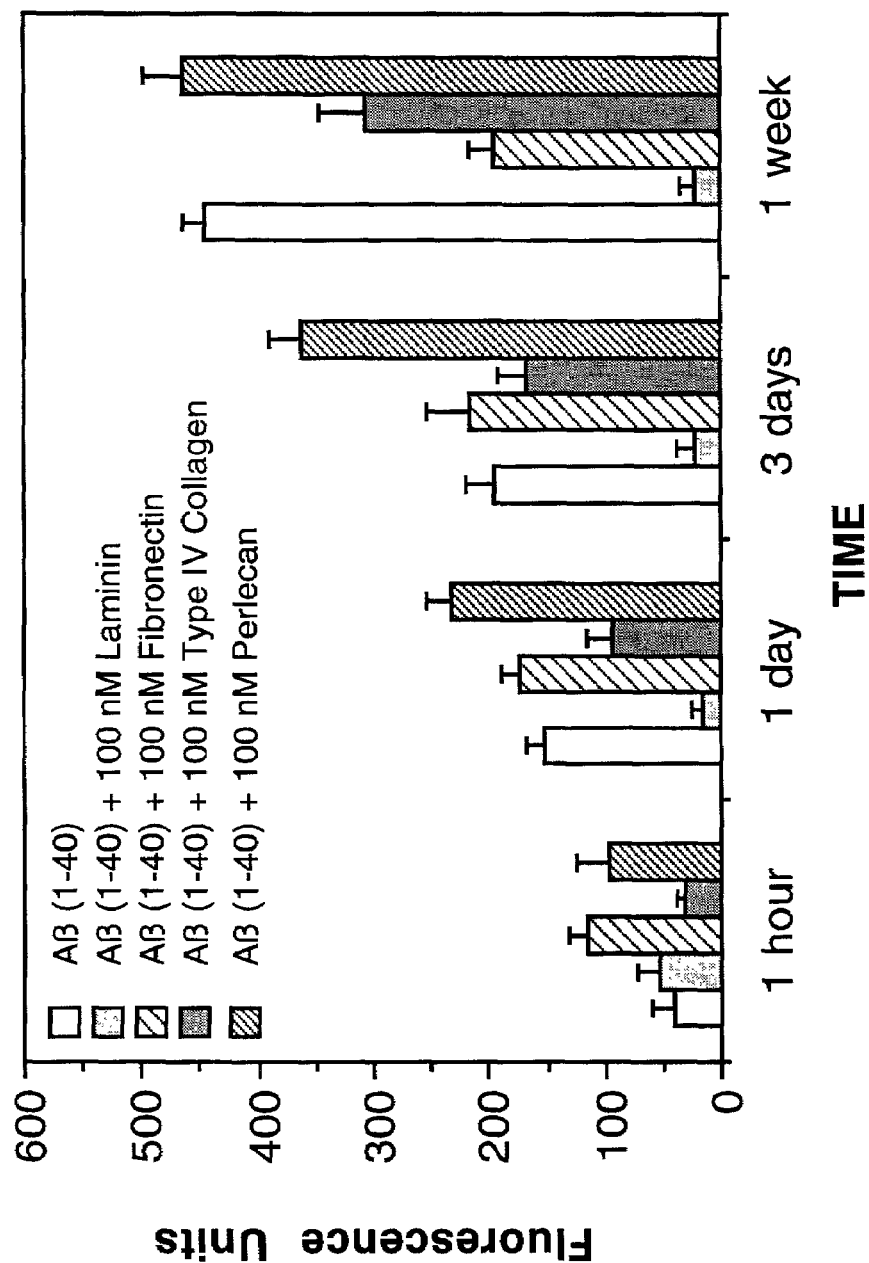
FIG. 3 compares the potent inhibition of Aβ amyloid fibril formation by laminin to other basement membrane components including fibronectin, type IV collagen and perlecan. Only laminin is found to have a potent inhibitory effect on Aβ fibrillogenesis as early as 1 hour after incubation.

To determine whether the inhibitory effects of laminin was specific to this basement membrane component, an direct comparison was made to other known basement membrane components including perlecan, fibronectin, and type IV collagen. In these studies 25 µM of Aβ (1-40) was incubated in the absence or presence of either 100 nM of laminin, 100 nM of fibronectin, 100 nM of type IV collagen and 100 nM of perlecan (FIG. 3). Freshly solubilized Aβ (1-40) when incubated at 37° C. gradually increased in fluorescence levels from 1 hour to 1 week (by 10.8-fold) (FIG. 3), as previously demonstrated (FIG. 2). Perlecan was found to significantly accelerate Aβ (1-40) amyloid formation at 1 day and 3 days, whereas fibronectin and type IV collagen only showed significant inhibition of Aβ (1-40) fibrillogenesis at 1 week. Laminin, on the other hand, was again found to be a very potent inhibitor of Aβ fibrillogenesis causing a 9-fold decrease at 1 and 3 days, and a 21-fold decrease at 1 week. This study reconfirmed the potent inhibitory effects of laminin on Aβ fibrillogenesis, and demonstrated the specificity of this inhibition, since none of the other basement membrane components (including fibronectin, type IV collagen and perlecan) were very effective inhibitors.

Figure 4:
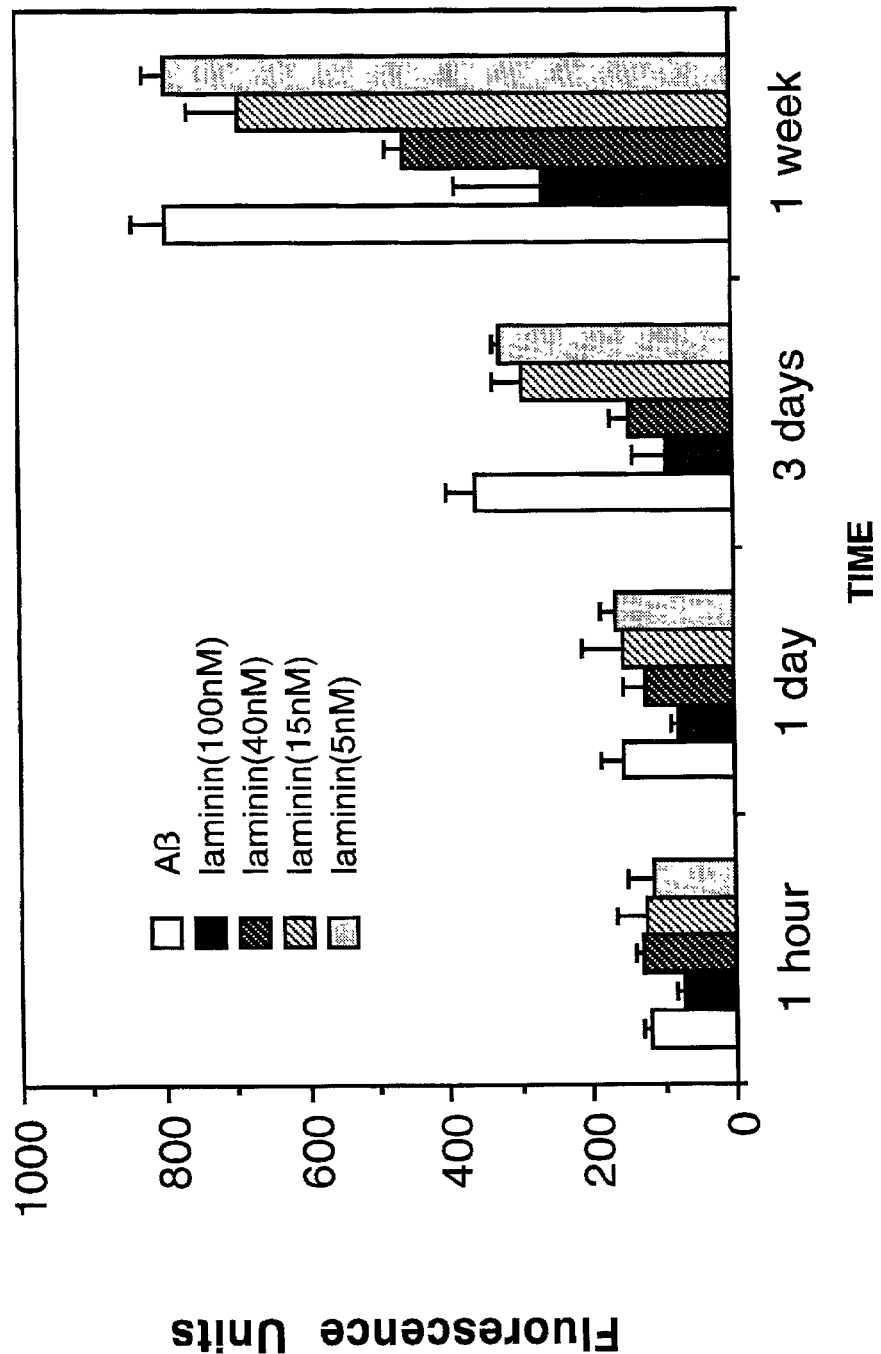
FIG. 4 is a graph of a 1 week Thioflavin T fluorometry assay utilized to determine the potential dose-dependent effects of laminin on inhibition of Aβ amyloid fibril formation. Significant dose-dependent inhibition of Aβ (1-40) amyloid fibril formation is observed at 1 day, 3 days and 1 week of treatment with increasing concentrations of laminin.

To determine whether the inhibitory effects of laminin on Aβ fibrillogenesis occurred in a dose-dependent manner, different concentrations of laminin (i.e. 5 nM, 15 nM, 40 nM and 100 nM) were tested. As shown in FIG. 4, freshly solubilized Aβ (1-40) when incubated at 37° C. gradually increased from 1 hour to 1 week, as previously demonstrated (FIGS. 2 and 3). 100 nM of laminin significantly inhibited Aβ fibril formation at all time points studied, including 1 hour, 1 day, 3 days and 7 days. Laminin was also found to inhibit Aβ fibril formation in a dose-dependent manner which was significant ($p<0.05$) by 3 days of incubation. At 3 days and 7 days, both 100 nM and 40 nM of laminin significantly inhibited Aβ fibril formation. This study reconfirmed that laminin was a potent inhibitor of Aβ fibril formation and that this inhibition occurred in a dose-dependent manner.

Example 3

Laminin Causes Dose-Dependent Dissolution of Pre-Formed Alzheimer's Disease Amyloid Fibrils The next study was implemented to determine whether laminin was capable of causing a dose-dependent dissolution of pre-formed Alzheimer's disease Aβ (1-40) amyloid fibrils. This type of activity would be important for any potential anti-Alzheimer's amyloid drug which can be used in patients who already have substantial amyloid deposition in brain. For example, Alzheimer's disease patients in mid-to late stage disease have abundant amyloid deposits in their brains as part of both neuritic plaques and cerebrovascular amyloid deposits. A therapeutic agent capable of causing dissolution of pre-existing amyloid would be advantageous for use in these patients who are at latter stages of the disease process.

For this study, 1 mg of Aβ (1-40)(Bachem Inc., Torrance, Calif., USA; Lot #WM365) was dissolved in 1.0 ml of double distilled water (1 mg/ml solution) and then incubated at 37° C. for 1 week. 25 µM of fibrillized Aβ was then incubated at 37° C. in the presence or absence of laminin (from EHS tumor; Sigma Chemical Company, St. Louis, Mo., USA) at concentrations of 125 nM, 63 nM, 31 nM and 16 nM containing 150 mM Tris HCl, 10 mM NaCl, pH 7.0. Following a 4 day incubation, 50 µl aliquots were added to 1.2 ml of 100 µM Thioflavin T (Sigma Chemical Co., St. Louis, Mo.) in 50 mM NaPO$_4$ (pH 6.0) for fluorometry readings as described in example 2.

Figure 5:
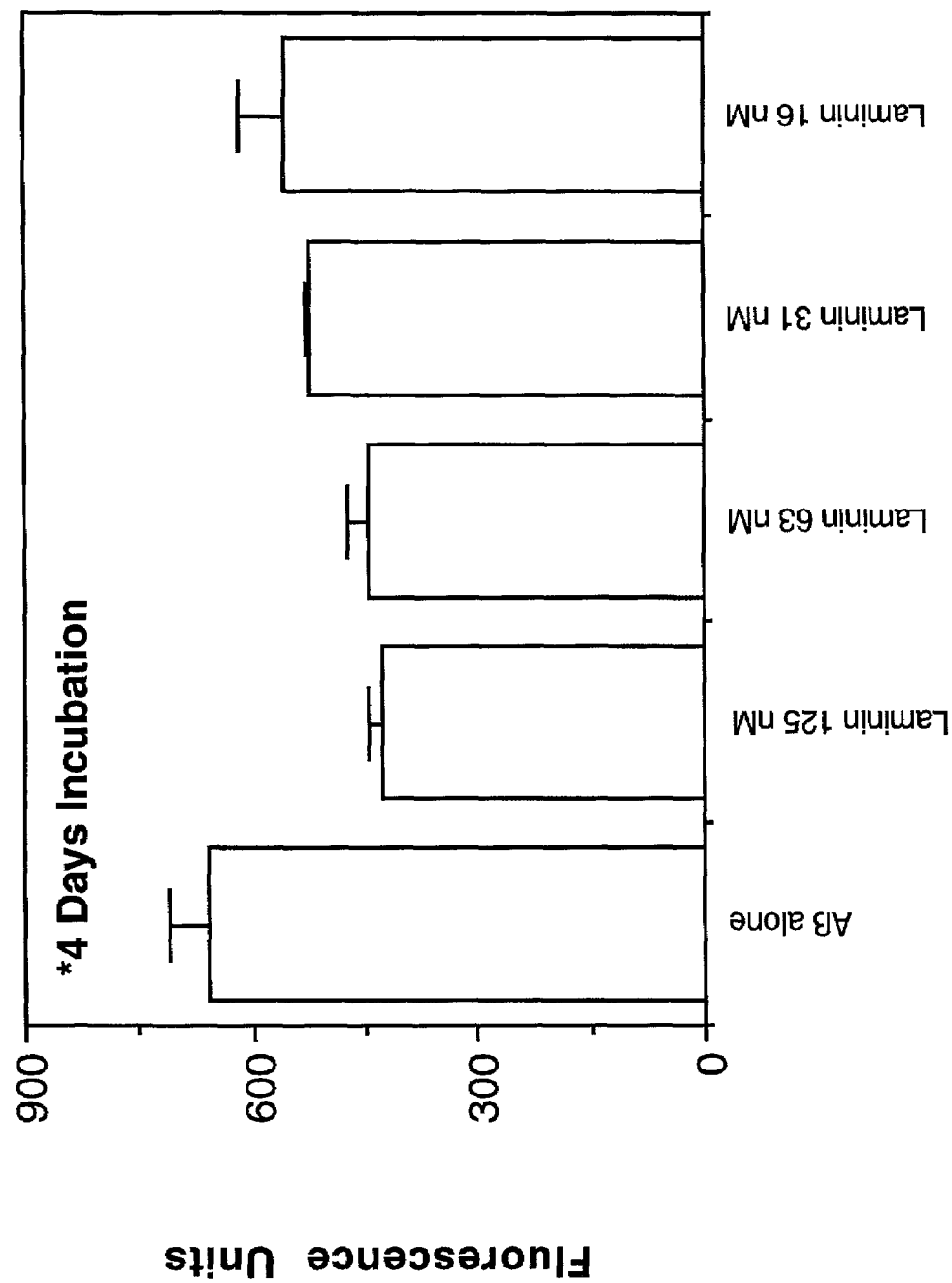
FIG. 5 is a graph of a Thioflavin T fluorometry assay utilized to determine the potential dose-dependent effects of laminin on dissolution of pre-formed Aβ (1-40) amyloid fibrils within a 4 day incubation period. Laminin causes dissolution of pre-formed Aβ amyloid fibrils in a dose-dependent manner.

As shown in FIG. 5, dissolution of pre-formed Alzheimer's disease Aβ amyloid fibrils by laminin occurred in a dose-dependent manner. A significant ($p<0.001$) 41% dissolution of pre-formed Aβ amyloid fibrils was observed with 125 nM of laminin, whereas 63 nM of laminin caused a significant ($p<0.001$) 39% dissolution. Furthermore, 31 nM and 16 nM of laminin still caused a significant ($p<0.01$) 28% and 25% dissolution of pre-formed Aβ amyloid fibrils. These data demonstrated that laminin causes dissolution of pre-formed Alzheimer's disease amyloid fibrils in a dose-dependent manner following a 4-day incubation.

Example 4

Laminin Does Not Significantly Inhibit Islet Amyloid Polypeptide (Amylin) Fibril Formation In the next study, the specificity of the laminin inhibitory effects on Alzheimer's disease amyloid was determined by testing laminin's potential effects on another type of amyloid. Amyloid accumulation occurs in the islets of Langerhans in ~90% of patients with type II diabetes (Westermark et al, *Am. J. Path.* 127:414-417, 1987). The major protein in islet amyloid is a 37 amino acid peptide, termed islet amyloid polypeptide or amylin which is known to be a normal secretory product of the beta-cells of the pancreas (Cooper et al, *Proc. Natl. Acad. Sci.,* 84:8628-8632, 1987). The dose-dependent effects of laminin on amylin fibrillogenesis was determined using the Thioflavin T fluorometry assay. 25 µM of Aβ (1-40) (Bachem Inc., Torrance, Calif., USA; Lot #WM365) was incubated in microcentrifuge tubes at 37° C. for 1 week (in triplicate), either alone, or in the presence of 5 nM, 15 nM, 40 nM and 100 nM of laminin in 150 mM Tris HCl, 10 mM NaCl, pH 7.0 (TBS). 50 µl aliquots were taken from each tube for analysis at 1 hr, 1 day, 3 days, and 1 week using Thioflavin T fluorometry as described in example 2.

Figure 6:
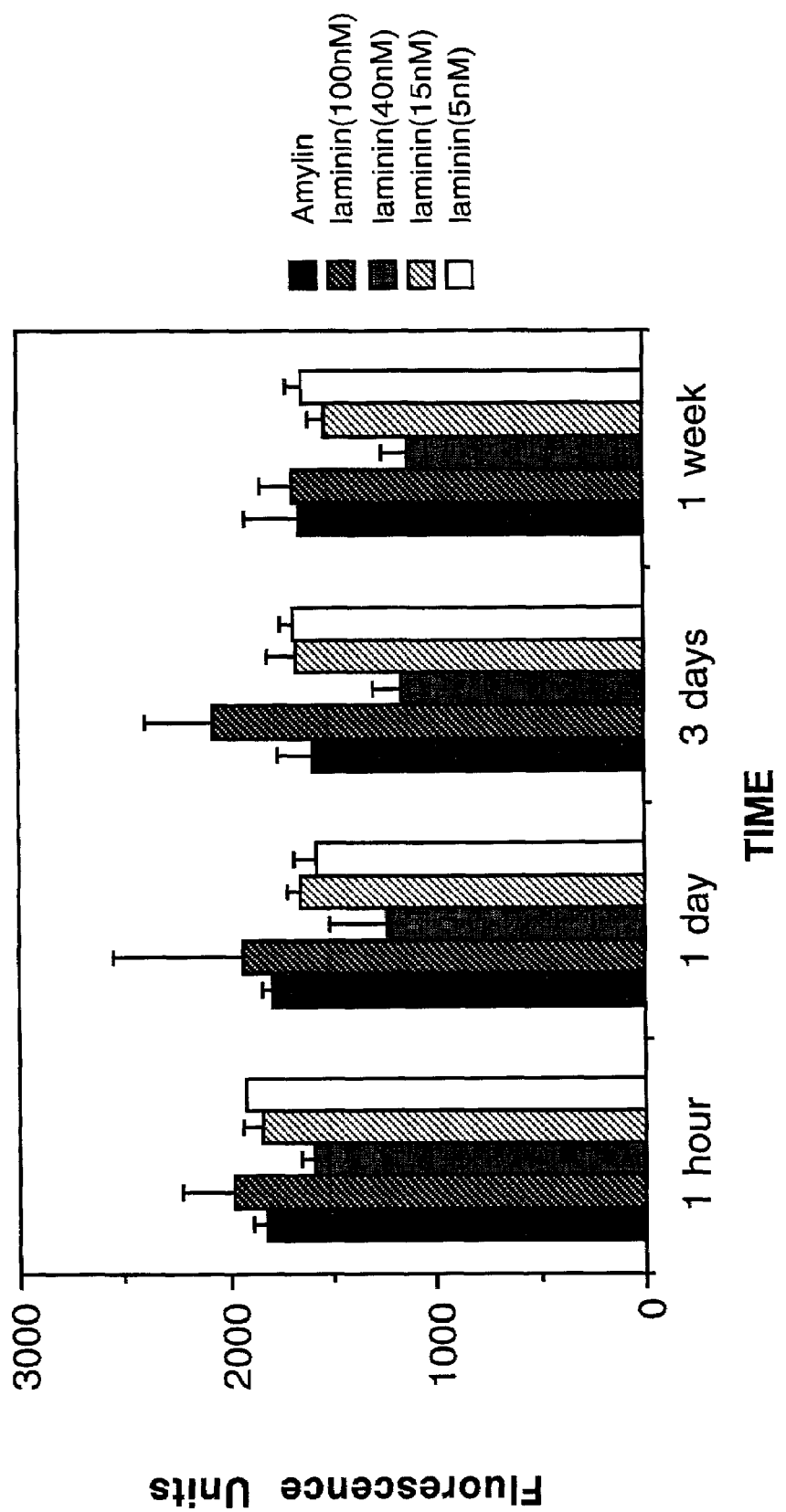
FIG. 6 is a graph of a 1 week Thioflavin T fluorometry assay utilized to determine the effects of laminin on islet amyloid polypeptide (amylin) fibrillogenesis, and determine whether laminin causes a dose-dependent inhibition of amylin fibril formation. Laminin does not significantly inhibit amylin fibrillogenesis suggesting its specificity for Alzheimer's disease amyloidosis.

As shown in FIG. 6, freshly suspended amylin alone following a 1-hour incubation at 37° C. reached a maximum fluorescence of 1800 fluorescence units, which did not significantly change during the 1 week experimental period. The initial high fluorescence of amylin was attributed to amylin's ability to spontaneously form amyloid fibrils within a very short incubation period. Laminin at 100 nM did not significantly inhibit amylin fibril formation at all time points within the 1 week experimental period (FIG. 6). In addition, no significant inhibition of amylin fibrillogenesis by laminin at decreasing concentrations (i.e. 40 nM, 15 nM and 5 nM) was observed, even though a decrease (but not significant) in amylin fibril formation was observed with 40 nM of laminin at 1 day, 3 days and 1 week (FIG. 6). This study demonstrated that the inhibitory effects of laminin did not occur with amylin fibril formation, and demonstrated the specificity of the observed laminin inhibitory effects on Alzheimer's disease amyloid.

Example 5

Identification of V8 and Trypsin-Resistant Laminin Fragments which Interact with the Beta-Amyloid Protein of Alzheimer's Disease In the next set of studies, we determined whether small fragment(s) of laminin generated by V8 or trypsin digestion would bind to Aβ. This would enable one to determine the domain(s) of laminin which bind Aβ and likely play a role in inhibition of Aβ fibril formation and causing dissolution of preformed Alzheimer's amyloid fibrils (as demonstrated in the invention).

For these experiments, Aβ (1-40) was biotinylated according to the manufacturer's protocol (Pierce, Rockford, Ill.). For the ligand studies, intact EHS laminin was left undigested, or digested with V8 or trypsin (Sigma Chemical Company, St. Louis, Mo., USA). More specifically, 2 µg of trypsin or V8 protease in 2 µl of 50 MM Tris-HCl buffer (pH 8.0) were added to 50 µl of laminin (50 µg)(in the same buffer) and incubated overnight at 37° C. The next day, 10 µl of protease-digested laminin (or undigested laminin) was mixed with 10 µl of 2× sodium dodecyl sulfate polyacrylamide gel electrophoresis (SDS-PAGE) sample buffer, and heated for 5 minutes in a boiling water bath. SDS-PAGE was performed according to the method of Laemmli (Laemmli, U.K. *Nature* 227:680-685, 1970), or according to the method of Schägger and Jagow (Schägger and Jagow, *Anal. Biochem.* 166:368-379, 1987) using a Mini-Protean II electrophoresis system (Biorad) with precast 4-15% Tris-Glycine or 10-20% tricine polyacrylamide gels, respectively, and under non-reducing conditions. Electrophoresis occurred at 200V for 45 minutes along with pre-stained molecular weight standards.

After SDS-PAGE (10-20% tricine or 4-15% Tris-Glycine gels) was performed as described above, the separated laminin and its fragments (total protein of 10 µg/lane) were transferred to polyvinylidine difluoride membrane (PVDF) using a Mini transblot electrophoresis transfer cell (Biorad, Hercules, Calif., U.S.A.). Electrotransfer was performed at 100V for 2 hours. Following transfer, membranes were rinsed with methanol and dried. The fragment(s) of laminin involved in binding to Aβ were then detected by using biotinylated-Aβ (1-40), as described above. Blots were probed for 2 hours with 2 µM biotinylated Aβ (1-40) in TTBS. The membranes were then rinsed three times (10 seconds each) with TTBS, probed for 30 minutes with strepavidin alkaline phosphatase conjugate (Vectastain), rinsed again (as described above), and followed by the addition of an alkaline phosphatase substrate solution (Vectastain). Following color development, the reaction was stopped by flushing the membranes with double distilled water.

Figure 7:
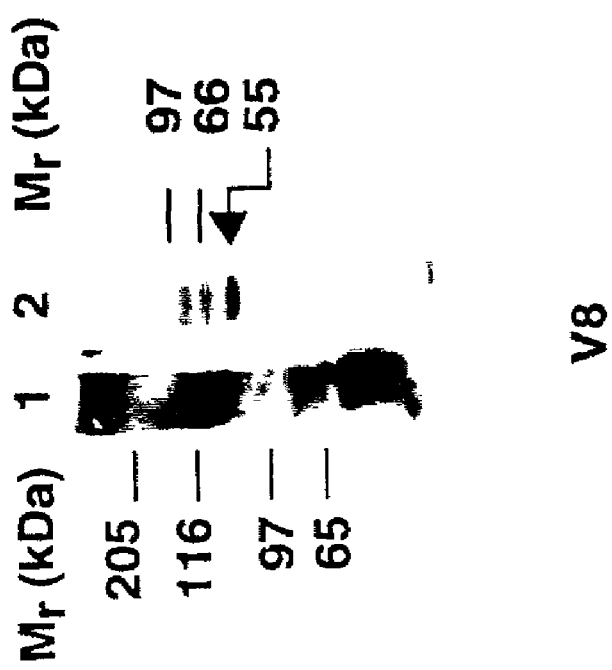
FIG. 7 is a black and white photograph of laminin digested with V8 protease, separated by SDS-PAGE and following interaction with biotinylated Aβ (1-40). The smallest fragment of V8-resistant laminin that interacts with Aβ is a ~55 kilodalton fragment.

As shown in FIG. 7, V8-digested laminin produced multiple protein fragments which interacted with biotinylated Aβ (1-40). Using a 4-15% Tris-Glycine gel system (FIG. 7, lane 1), V8-resistent laminin fragments which interacted with Aβ included fragments of ~400 kDa (which probably represented intact laminin which was left undigested), ~100-130 kDa, ~85 kDa, and a prominent fragment at ~55 kDa. Using a 10-20% tricine gel system (FIG. 7, lane 2), V8-resistent laminin fragments which interacted with Aβ included fragments of ~130 kDa, ~85 kDa, and a prominent fragment at ~55 kDa (FIG. 7, lane 2, arrow). It is important to note that molecular size expressed in kilodaltons (kDa) are generally approximate. This study demonstrated that the smallest V8-resistant protein fragment of laminin which interacted with Aβ (1-40) was ~55 kDa.

Figure 8:
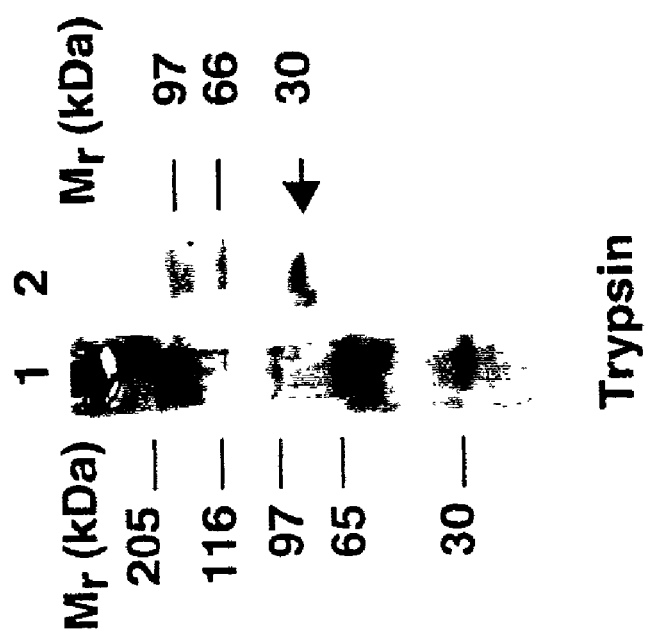
FIG. 8 is a black and white photograph of laminin digested with trypsin, separated by SDS-PAGE and following interaction with biotinylated Aβ (1-40). The smallest fragment of trypsin-resistant laminin that interacts with Aβ is a ~30 kilodalton fragment.

As shown in FIG. 8, trypsin-digested laminin produced multiple protein fragments which interacted with biotinylated Aβ (1-40). Using a 4-15% Tris-Glycine gel system (FIG. 8, lane 1), trypsin-resistant laminin fragments which interacted with Aβ included fragments of ~400 kDa (which probably represented intact laminin which was left undigested), ~150-200 kDa, ~97 kDa, ~65 kDa and a prominent fragment at ~30 kDa. Using a 10-20% tricine gel system (FIG. 8, lane 2), trypsin-resistant laminin fragments which interacted with Aβ included fragments of ~97 kDa, ~90 kDa, ~65 kDa and a prominent fragment at ~30 kDa (FIG. 8, lane 2, arrow). This study demonstrated that the smallest trypsin-resistant fragment of laminin which interacted with Aβ (1-40) was ~30 kDa.

Example 6

Identification of Elastase-Resistant Laminin Fragments Which Interact with the Beta-Amyloid Protein of Alzheimer's Disease In the next set of studies, we determined whether small fragment(s) of laminin generated by elastase digestion would bind to Aβ. In addition, we sequenced and identified the region within elastase-resistant laminin which interacted with Aβ. For these experiments, Aβ (1-40) was biotinylated according to the manufacturer's protocol (Pierce, Rockford, Ill.). For the ligand studies, intact EHS laminin was left undigested, or digested with elastase (Sigma Chemical Company, St. Louis, Mo., USA). For elastase digestion, 2 µg of elastase in 8 µl of 50 mM Tris-HCl buffer (pH 8.0) was added to 50 µl of laminin (50 µg)(in the same buffer) and incubated for 1.5 hours or 2.5 hours at 37° C. In addition, as a control, 2 µg of elastase in 50 µl of 50 mM Tris-HCl buffer (pH 8.0) was incubated for 2.5 hours at 37° C. Following the appropriate incubation times as described above, 10 µl of each of the above incubations were mixed with 10 µl of 2× SDS-PAGE electrophoresis sample buffer, and heated for 5 minutes in a boiling water bath. SDS-PAGE was performed according to the method of Laemmli (Laemmli, Nature 227:680-685, 1970) using a Mini-Protean II electrophoresis system with precast 4-15% Tris-Glycine polyacrylamide gels, and under non-reducing conditions. Electrophoresis occurred at 200V for 45 minutes along with pre-stained molecular weight standards (Biorad).

After SDS-PAGE was performed as described above, the separated laminin fragments were transferred to PVDF using a Mini transblot electrophoresis transfer cell (Millipore, Bedford, Mass., U.S.A.). Electrotransfer was performed at 100V for 2 hours. Following transfer, membranes were rinsed with methanol, dried and cut into two equal parts which were used for Aβ ligand blotting, or Coomassie blue staining and subsequent amino acid sequencing. The fragment(s) of laminin involved in binding to Aβ were then detected by using biotinylated-Aβ (1-40), as described above. Blots were probed for 2 hours with 2 µM biotinylated Aµ (1-40) in TTBS. The membranes were then rinsed three times (10 seconds each) with TTBS, probed for 30 minutes with strepavidin alkaline phosphatase conjugate (Vectastain), rinsed again (as described above), and followed by the addition of an alkaline phosphatase substrate solution (Vectastain). Following color development, the reaction was stopped by flushing the membranes with double distilled water.

For Coomassie blue staining, PVDF membranes were immersed with 0.2% Coomassie Brilliant blue (w/v) in 50% methanol, 10% acetic acid, and 40% distilled water for 2 minutes, and then rinsed with 50% methanol, 10% acetic acid, and 40% distilled water until visible bands were observed, and no background staining was present. The 55 kDa Aβ-binding laminin fragment, described below, was sent to the Biotechnology Service Center (Peptide Sequence Analysis Facility at the University of Toronto, Toronto, Ontario, Canada) and subjected to amino acid sequencing using a Porton 2090 Gas-Phase Microsequencer (Porton Instruments, Tarzana, Calif.) with on-line analysis of phenylthiohydantoin derivatives.

In FIG. 9A represents an Aβ ligand blot whereas FIG. 9B represents the equivalent Coomassie blue stained blot. As shown in FIG. 9A (lanes 2 and 3), elastase-digested laminin produced multiple protein fragments which bound biotinylated Aβ(1-40). FIG. 9A, lane 1 represents undigested mouse EHS laminin, whereas lanes 2 and 3 represents laminin which had been digested with elastase for 1.5 hours or 2.5 hours, respectively. FIG. 9A, lane 4 represents elastase digestion for 2.5 hours in the absence of laminin. Undigested laminin (FIG. 9A, lane 1) which interacted with Aβ included multiple bands from >400 kDa to >~86 kDa, with the most prominent Aβ-interaction occurring with intact laminin (i.e. 400 kDa). Elastase-resistant laminin protein fragments which interacted with Aβ (FIG. 9A, lanes 2 and 3) included fragments of >~400 kDa, ~130 kDa (arrowhead), ~80-90 kDa, ~65 kDa and a prominent band at ~55 kDa (arrow). The interaction of these elastase-resistant laminin protein fragments with Aβ were only observed under non-reducing conditions suggesting that the Aβ interaction was also conformation dependent. The 130 kDa elastase resistant laminin fragment which interacts with Aβ, is also believed to be part of the E8 fragment (see FIG. 11), and is the same protein fragment of laminin that appears to be present in human serum and cerebrospinal fluid (see Examples 10 and 11). FIG. 9A, lane 4 demonstrates that the band observed at ~29 kDa represents non-specific Aβ binding due to the presence of the elastase enzyme alone.

FIG. 9B demonstrates all of the multiple protein bands which were stained by Coomassie blue. Note, for example, in FIG. 9B, lanes 2 and 3, that elastase digestion of laminin produced multiple protein fragments between ~55 kDa and ~90 kDa which did not bind Aβ, and were not observed in the Aβ ligand blot (FIG. 9A, lanes 2 and 3).

Example 7

An Aβ-Binding Domain Within Laminin is Identified Within the Globular Repeats of the Laminin A Chain The 55 kDa laminin fragment (ie. produced following 1.5 hours of elastase digestion) that demonstrated positive Aβ binding interaction by ligand blotting was then prepared (FIG. 9, Panel B, lane 2, arrow) in large amounts for amino acid sequencing (as described in example 6). Sequence data determined the exact location within laminin that was involved in binding to Aβ. An 11-amino acid sequence was determined from sequencing of the 55 kDa band. The sequence identified was:

Leu-His-Arg-Glu-His-Gly-Glu-Leu-Pro-Pro-Glu (SEQ ID NO:1).

The specific Aβ-binding domain within laminin was then identified by comparison to known mouse laminin sequence (Sasaki and Yamada, J. Biol. Chem. 262:17111-17117, 1987; Sasaki et al, Proc. Natl. Acad. Sci. 84:935-939, 1987; Durkin, et al, Biochem. 27:5198-5204, 1988; Sasaki et al, J. Biol. Chem. 263:16536-16544, 1988), since mouse EHS laminin was utilized in the studies of the present invention. In addition, the complete amino acid sequence within laminin was retrieved from the National Center for Biotechnology Information, Bethesda, Md., U.S.A.

Figure 11:
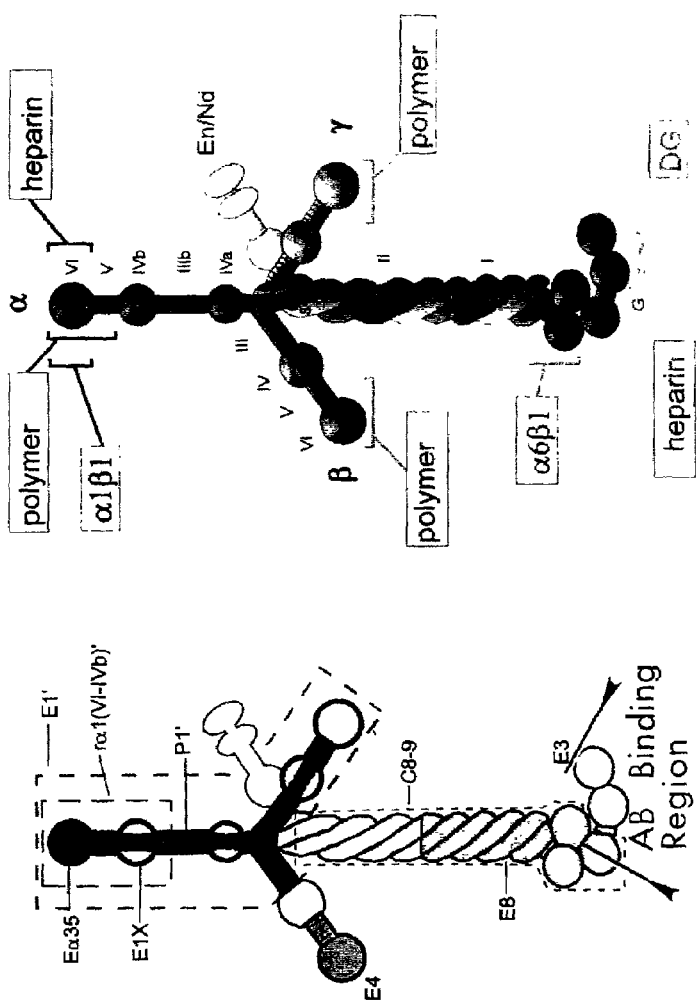
FIG. 11 shows schematic diagrams of laminin and the newly discovered "Aβ-binding region" of laminin (shown in left panel; between the two arrowheads) which is situated within the last three globular domains of the laminin A chain.

FIG. 10 shows the complete amino acid sequence of mouse laminin A chain (Genebank accession number P19137; SEQ ID NO: 4). The 11 amino acid protein fragment sequenced from the ~55 kDa protein within laminin which binds Aβ is identified (FIG. 10; bold underline and arrowhead; SEQ ID NO: 1) and matches exactly to the region within the third globular domain repeat of laminin A chain (FIG. 11). The fourth globular domain repeat of mouse laminin A chain is shown as SEQ ID NO: 2 (Genebank Accession Number P19137; amino acids #2746-2922), whereas the fourth globular domain repeat of human laminin A chain is shown as SEQ ID NO: 3 (Genebank Accession Number P25391; amino acids #2737-2913).

FIG. 11 shows two schematic representations of laminin (Colognato-Pyke et al, J. Biol. Chem. 270:9398-9406, 1995) and the newly discovered Aβ-binding region of laminin (shown in left panel; between the two arrowheads) which is situated within the last three globular domains of the laminin A chain. The left panel of FIG. 11 illustrates laminin and fragments generated following protease digestions. Elastase fragments E1', E1X (dark line border), E-alpha-35 and E4 all correspond to regions of the short arms of laminin. Long arm fragments are E8, E3 and cathepsin G fragment C8-9. The E8 fragment produced by elastase digestion of laminin contains the long arm fragments containing the distal part of the long arm and the G subdomains 1-3, and consists of a 130-150 kda (Yurchenco and Cheng, *J. Biol. Chem.* 268: 17286-17299, 1993). The E3 fragments also produced by elastase digestion of laminin contains the distal long arm globule with G subdomains 4 and 5. The E3 fragment shown in FIG. 11, Panel A, has previously shown to be a doublet at ~60 kDa and ~55 kDa (Yurchenco and Cheng, *J. Biol. Chem.* 268:17286-17299, 1993). This also confirms our discovery whereby the ~55 kDa fragment which we found to bind Aβ is localized within the E3 region of laminin (FIG. 11, Left Panel).

The right panel of FIG. 11 depicts the function map with the alpha (A chain), β (B1 chain) and gamma (B2 chain) chains of laminin shown in shades of decreasing darkness. EGF repeats are indicated by bars in the rod domains of the short arm. Domains, based on sequence analysis, are indicated in small Roman numerals and letters. The locations of heparin-binding, polymer-forming, and the active alpha1β1 integrin-binding sites are shown in bold-face for the alpha-chain short arm. The long arm functions of heparin binding (heparin), alpha6β1 integrin-recognition site (alpha6β1), and dystroglycan (DG), mapped in other studies, are indicated in gray-shaded labels. It is interesting to note that the Aβ-binding region of laminin is also a region involved in binding to heparin.

It should also be emphasized that the globular domain repeats of the laminin A chain likely interacts with Aβ in a conformation dependent manner, since the interaction of the ~55-kilodalton elastase-resistant protein fragments with Aβ was only observed under non-reducing conditions.

Example 8

Identification of Laminin and Laminin Protein Fragments in Human Serum and Cerebrospinal Fluid Derived from Alzheimer's disease, Type II Diabetes, and/or Normal Aged Patients In the next study, western blotting techniques using a polyclonal antibody against laminin was used to determine whether intact laminin and/or laminin fragments were present in human serum and cerebrospinal fluid obtained from Alzheimer's disease, type II diabetes and/or normal aged patients. In this study, human serum was obtained from the Alzheimer's disease Research Center at the University of Washington from either living aged patients who may have had corresponding mini-mental state examinations (where a score of 30 is normal, a score of 15 suggests moderate dementia and a score <10 suggests severe dementia), or from living aged patients who had subsequently died and were diagnosed at autopsy with Alzheimer's disease (following examination of their brains obtained postmortem). In addition, human serum was obtained from the Diabetes Endocrinology Research Center at the University of Washington. The following human serums were obtained and analyzed as part of this study: 1) patient #9; a normal 67 yr old female with a mini-mental score of 30; 2) patient #5226—a 70 year old female with confirmed moderate Alzheimer's disease who also had a mini-mental score of 12; 3) patient #5211—a 66 year old male with confirmed Alzheimer's disease who also had a mini-mental score of 25; 4) patient B—a 63 year old male who had confirmed type II diabetes; 5) patient #5223—a 68 year old female with confirmed Alzheimer's disease who also had a mini-mental score of 22; 6) patient #22—an 83 yr old normal aged female who also had a mini-mental score of 30; 7) patient #C—a 68 year old male with confirmed type II diabetes. Each of these serums were utilized in this study and represent lanes 1-7 (left side) of FIG. 12 (in the same order as above).

In addition, cerebrospinal fluid was obtained from the Alzheimer's disease Research Center at the University of Washington from either living aged patients who may have had corresponding mini-mental state examinations, or from living aged patients who had subsequently died and were diagnosed at autopsy with Alzheimer's disease (following examination of their brains obtained postmortem). The following human cerebrospinal fluids were obtained as part of this study: 1) patient #6—a normal 64 year old female who had a mini-mental score of 30; 2) patient #7—a normal 67 year old male who had a mini-mental score of 30; 3) patient #8—a normal 80 year old female who had a mini-mental score of 30; 4) patient #9—a normal 67 year old female who had a mini-mental score of 30; 5) patient #1111P—a normal 78 year old female who had a mini-mental score of 30; 6) patient #50—a 66 year old male patient with probable moderate Alzheimer's disease as indicated by a mini-mental score of 15; 7) patient #54—a 73 year old male with probable severe Alzheimer's disease as indicated by a mini-mental score of 8. Each of these cerebrospinal fluid samples were utilized in this study and represent lanes 1-7 (right side) of FIG. 12 (in the same order as above).

For the study described above, 10 µl of human serum diluted at 1:10, or 10 µl of undiluted human cerebrospinal fluid was added to 10 µl of SDS-PAGE buffer and ligand blots were prepared as in Example 6. Blots were probed for 2 hours with a polyclonal antibody (used at a dilution of 1:10,000 in TTBS) against EHS laminin (Sigma Chemical Company, St. Louis, Mo.). The membranes were then rinsed 3 times (10 seconds each) with TTBS and incubated for 1 hour with a biotinylated goat anti-rabbit IgG secondary antibody diluted 1:1,000 with TTBS. The membranes were then rinsed three times (10 seconds each) with TTBS, probed for 30 minutes with strepavidin alkaline phosphatase conjugate (Vectastain), rinsed again (as described above), followed by the addition of an alkaline phosphatase substrate solution (Vectastain). Following color development, the reaction was stopped by flushing the membranes with double distilled water.

Figure 12:
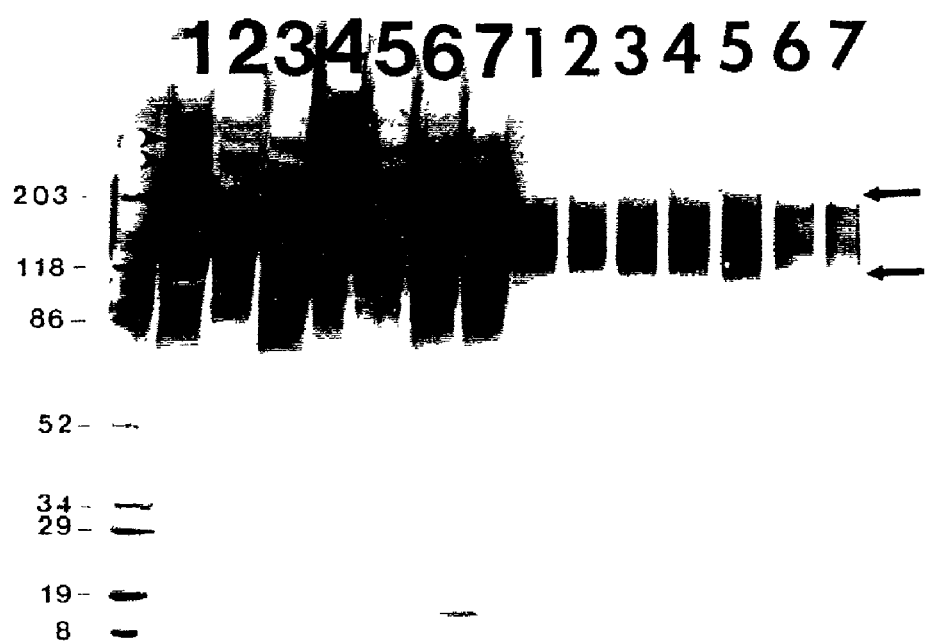
FIG. 12 is a black and white photograph of a Western blot demonstrating the presence of laminin (arrowheads) and/or laminin-derived protein fragments (bands between the two arrows) in human serum (lanes 1-7; left side) and human cerebrospinal fluid (lanes 1-7; right side) obtained from Alzheimer's disease, type II diabetes and normal aged patients. A ~110-130 kilodalton range of laminin positive protein fragments (between the two arrows) is present in both human serum and cerebrospinal fluid, whereas intact laminin (arrowheads) is only present in serum but not in cerebrospinal fluid.

As shown in FIG. 12, intact laminin (arrowheads) was present in human serum (lanes 1-7; left side) but not in human cerebrospinal fluid (lanes 1-7; right side). Qualitative observations suggest that intact laminin (as described above) may have been decreased in serum of Alzheimer's disease patients in comparison to controls (i.e. compare intact laminin in FIG. 12, lane 1, left side-normal individual; to FIG. 12, lane 2, left side-Alzheimer's disease patient). In addition to intact laminin, human serum derived from Alzheimer's disease, type II diabetes and normal aged patients also contained laminin immunoreactivity in a series of band from ~120 kDa to ~200 kDa (FIG. 12, bands observed between the two arrows). On the other hand, cerebrospinal fluid samples did not contain intact laminin (FIG. 12; lanes 1-7; right side) but only contained a series of laminin immunoreactive protein fragments from ~120 kDa to ~200 kDa (i.e. FIG. 12, bands observed between the two arrows). This study determined that a series of laminin protein fragments are present in both human serum and cerebrospinal fluid of Alzheimer's disease, type II diabetes and normal aged patients, whereas intact laminin is only present in human serum. The novel discovery of the laminin fragments in human cerebrospinal fluid suggests that it may be used as a marker to determine the extent of laminin breakdown in the brain during Alzheimer's disease and other brain disorders.

Example 9

Identification of a ~130 Kilodalton Laminin Protein Fragment in Human Serum of Alzheimer's disease, Type II Diabetes and Normal Aged Patients which Binds Aβ

In the next study, Aβ ligand blotting techniques were utilized to identify whether laminin or laminin protein fragments present in human serum bind Aβ. In this study, human serum was obtained from the Alzheimer's disease Research Center at the University of Washington from either living patients who may have had corresponding mini-mental state examinations (where a score of 30 is normal, a score of 15 suggests moderate dementia and a score <10 suggests severe dementia), or from living patients who had subsequently died and were diagnosed at autopsy with Alzheimer's disease (following examination of their brains obtained postmortem). In addition. human serum was obtained from the Diabetes Endocrinology Research Center at the University of Washington. The first six human serum samples (i.e. FIG. 13, lanes 1-6) were the same serum samples as indicated in Example 8. In addition, FIG. 13 lanes 7-10 consisted of human serum obtained from lane 7) patient #E—a 54 year old male with confirmed type II diabetes, lane 8) patient #5230—a 72 year old female with confirmed moderate Alzheimer's disease who had a mini-mental score of 19, lane 9) patient #E—a 54 year old male with confirmed type II diabetes, and lane 10) patient #F—a 69 year old male with confirmed type II diabetes.

For this study, Aβ (1-40) was biotinylated according to the manufacturer's protocol (Pierce, Rockford, Ill.). For the ligand studies, following SDS-PAGE as described above in Example 8, separated laminin and its fragments present in human serum were transferred to polyvinylidine difluoride membrane (PVDF) using a Mini transblot electrophoresis transfer cell. Electrotransfer was performed at 100V for 2 hours. Following transfer, membranes were rinsed with methanol and dried. The fragment(s) of laminin in human serum involved in binding to Aβ were then detected by using biotinylated-Aβ (1-40). Blots were probed for 2 hours with 1 μM biotinylated Aβ (1-40) in TTBS. The membranes were then rinsed three times (10 seconds each) with TTBS, probed for 30 minutes with strepavidin alkaline phosphatase conjugate (Vectastain), rinsed again (as described above), and followed by the addition of an alkaline phosphatase substrate solution (Vectastain). Following color development, the reaction was stopped by flushing the membranes with double distilled water.

Figure 13:
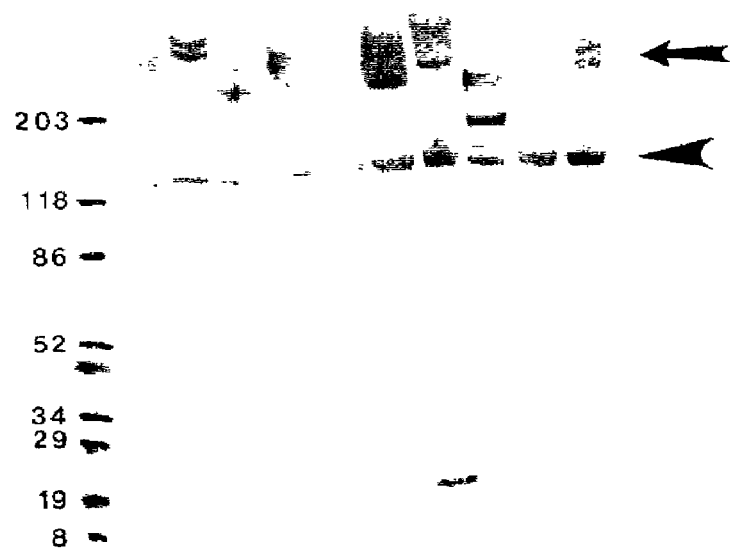
FIG. 13 is a black and white photograph demonstrating that intact laminin (arrow) and a prominent ~130 kilodalton band (arrowhead) present in human Alzheimer's disease, type II diabetes and normal aged patient serum, bind Aβ. The Aβ-binding laminin and specific Aβ-binding laminin fragments in human serum were identified following separation by SDS-PAGE and interaction with nanomolar concentrations of biotinylated Aβ (1-40).

As shown in FIG. 13, Aβ interacted with intact human laminin (arrow) in most samples of human serum. However, it was surprising to note that intact laminin was virtually absent in 2 of the 4 Alzheimer's disease patients serum (FIG. 13, lanes 5 and 8), suggesting that laminin-derived fragments may be important in Alzheimer's disease as a diagnostic marker. The most interesting discovery was that of all the laminin immunoreactive protein fragments found in human serum (i.e ~120 kDa to ~200 kDa, bands observed between the arrows, FIG. 12, lanes 1-7, right side), only a prominent ~130 kDa band was found to interact with Aβ (FIG. 13, arrowhead). This same prominent band is approximately the same molecular weight of the E8 band generated from mouse laminin following elastase digestion (see FIG. 9), and which also contains the globular domain repeats of the laminin A chain. This study therefore determined that besides intact laminin, human serum contains a ~130 kDa laminin fragment which binds to Aβ, and may be important for keeping Aβ soluble in biological fluids such as blood. This study also suggests that qualitative and quantitative assessment of laminin fragments in human serum may prove diagnostic for the extent and progression of Alzheimer's disease, type II diabetes and other amyloidoses.

Example 10

Identification of a ~130 Kilodalton Laminin Protein Fragment in Human Cerebrospinal Fluid of Alzheimer's disease and Normal Aged Patients which Binds Aβ

In the next study, Aβ ligand blotting techniques were utilized to identify whether laminin protein fragments (<200 kDa) present in human cerebrospinal fluid bind Aβ. In this study, human cerebrospinal fluid was obtained from the Alzheimer's disease Research Center at the University of Washington from either living aged patients who may have had corresponding mini-mental state examinations (where a score of 30 is normal, a score of 15 suggests moderate Alzheimer's disease and a score <10 suggests moderate Alzheimer's disease), or from living aged patients who had subsequently died and were diagnosed at autopsy with Alzheimer's disease (following examination of their brains obtained postmortem). The following human cerebrospinal fluids were obtained and analyzed as part of this study (depicted in FIG. 14, lanes 1-10): 1) patient #65—a 71 yr old male with probable severe Alzheimer's disease as indicated by a mini-mental score of 0; 2) patient #54—a 73 yr old male with probable severe Alzheimer's disease as indicated by a mini-mental score of 8.; 3) patient #6—a normal 64 yr old female who had a mini-mental score of 30; 4) patient #7—a normal 67 yr old male who had a mini-mental score of 30; 5) patient #8—a normal 80 yr old female who had a mini-mental score of 30; 6) patient #9—a normal 67 yr old female who had a mini-mental score of 30; 7) patient #1111P—a normal 78 yr old female who had a mini-mental score of 30; 8) patient #50—a 66 yr old male patient with probable moderate Alzheimer's disease as indicated by a mini-mental score of 15; 9) patient #52—a 69 yr old male with probable moderate Alzheimer's disease as indicated by a mini-mental score of 16; 10) patient #64—a 64 yr old male with probable severe Alzheimer's disease as indicated by a mini-mental score of 0. Each of these cerebrospinal fluid samples were utilized in this study and represent lanes 1-10 of FIG. 14 (in the same order as above).

For this study, Aβ ligand blotting was employed as described in Example 9. The fragment(s) of laminin in human cerebrospinal fluid involved in binding to Aβ were detected by using biotinylated-Aβ (1-40). Blots were probed for 2 hours with 50 nM of biotinylated Aβ (1-40) in TTBS. The rest of the Aβ ligand blotting procedure is as described above in Example 9.

Figure 14:
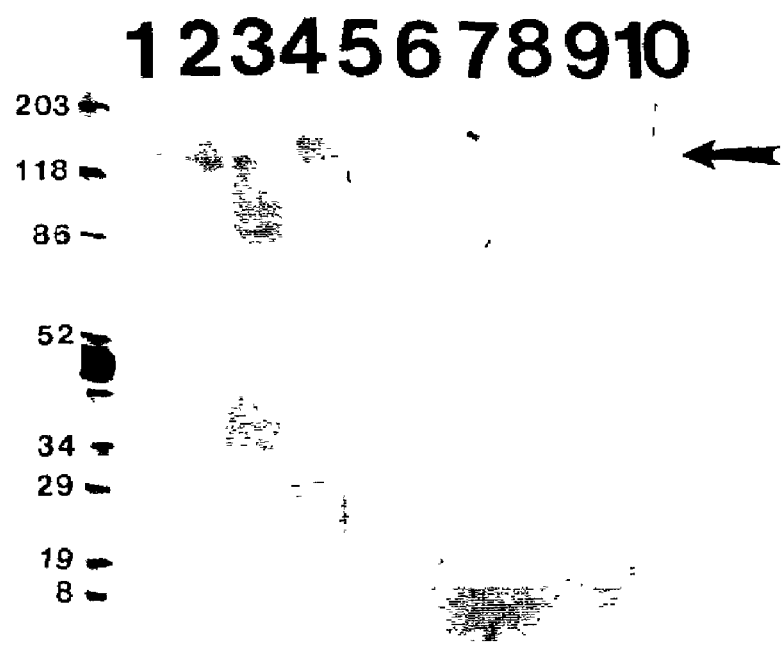
FIG. 14 is a black and white photograph demonstrating the presence of a prominent ~130 kilodalton band (arrow) in human Alzheimer's disease and normal aged patient cerebrospinal fluid, identified following separation by SDS-PAGE and following interaction with nanomolar concentrations of biotinylated Aβ (1-40). This same ~130 kilodalton Aβ-binding protein is also present in human serum (FIG. 13).

As shown in FIG. 14, Aβ interacted with laminin fragment bands between ~120 kDa and ~200 kDa in most samples of human cerebrospinal fluid. As observed in human serum, most samples of human cerebrospinal fluid also contained a prominent ~130 kDa laminin fragment (FIG. 14, arrow) which interacted with Aβ. No intact Aβ-binding laminin was found in human cerebrospinal fluid (not shown), as previously demonstrated (FIG. 12, Example 8). Again, this same prominent ~130 kDa Aβ-binding laminin fragment present in human cerebrospinal fluid is approximately the same molecular weight of the E8 band generated from laminin, and which also contains the globular domain repeats of the laminin A chain. This study therefore determined that human cerebrospinal fluid also contains a ~130 kDa laminin fragment which binds to Aβ, and may be important for keeping Aβ soluble in biological fluids such as cerebrospinal fluid.

Further Aspects and Utilizations of the Invention

Laminin-Derived Protein Fragments and Polypeptides

One therapeutic application of the present invention is to use laminin, laminin protein fragments which bind Aβ or other amyloid proteins, and/or laminin polypeptides derived from amino acid sequencing of the laminin fragments which bind Aβ (such as the ~130 kilodalton protein described herein) or other amyloid proteins, as potent inhibitors of amyloid formation, deposition, accumulation and/or persistence in Alzheimer's disease and other amyloidoses. The amyloid diseases include, but are not limited to, the amyloid associated with Alzheimer's disease and Down's syndrome (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $beta_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

The polypeptides referred to above may be a natural polypeptide, a synthetic polypeptide or a recombinant polypeptide. The fragments, derivatives or analogs of the polypeptides to any laminin fragment referred to herein may be a) one in which one or more of the amino acid residues are substituted with a conserved or non-conserved amino acid residue and such substituted amino acid residue may or may not be encoded by the genetic code, or b) one in which one or more of the amino acid residues includes a substituent group, or c) one in which the mature polypeptide is fused with another compound, such as a compound used to increase the half-life of the polypeptide (for example, polylysine), or d) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of the invention.

The tertiary structure of proteins refers to the overall 3-dimensional architecture of a polypeptide chain. The complexity of 3-dimensional structure arises from the intrinsic ability of single covalent bonds to be rotated. Rotation about several such bonds in a linear molecule will produce different nonsuperimpossable 3-dimensional arrangements of the atoms that are generally described as conformations.

Protein conformation is an essential component of protein-protein, protein-substrate, protein-agonist, protein-antagonist interactions. Changes in the component amino acids of protein sequences can result in changes that have little or no effect on the resultant protein conformation. Conversely, changes in the peptide sequences can have effects on the protein conformation resulting in reduced or increased protein-protein, etc. interactions. Such changes and their effects are generally disclosed in *Proteins: Structures and Molecular Properties* by Thomas Creightonm W. H. Freeman and Company, New York, 1984 which is hereby incorporated by reference.

"Conformation" and "conformation similarity" when used in this specification and claims refers to a polypeptide's ability (or any other organic or inorganic molecule) to assume a given shape, through folding and the like, so that the shape, or conformation, of the molecule becomes an essential part of it's functionality, sometimes to the exclusion of its chemical makeup. It is generally known that in biological processes two conformational similar molecules may be interchangeable in the process, even the chemically different. "Conformational similarity" refers to the latter interchangeability or substitutability. For example, laminin and laminin-derived protein fragments are among the subjects of the invention because they have been shown to bind the Aβ protein and render it inactive in fibril formation; it is contemplated that other molecules that are conformationally similar to laminin, or any claimed laminin fragment or polypeptide, may be substituted in the claimed method to similarly render the Aβ inactive in fibrillogenesis and other amyloid processes. In general it is contemplated that levels of conformational similarity at or above 70% are sufficient to assume homologous functionality in the claimed processes, though reduced levels of conformational similarity may be made to serve as well. Conformational similar levels at or above 90% should provide some level of additional homologue functionality.

Thus, one skilled in the art would envisage that changes can be made to the laminin sequence, or fragments or polypeptides thereof, that would increase, decrease or have no effect on the binding of laminin or fragments thereof, to Aβ amyloid. In addition, one skilled in the art would envisage various post-translational modifications such as phosphorylation, glycosylation and the like would alter the binding of laminin, laminin fragments or laminin polypeptides to Aβ amyloid.

The polypeptides of the present invention include the polypeptides or fragments of laminin described herein, including but not limited to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as well as polypeptides which have at least 70% similarity (preferably 70% identity) and more preferably a 90% similarity (more preferably a 90% identity) to the polypeptides described above.

Fragments or portions of the polypeptides or fragments of laminin of the present invention may be employed for producing the corresponding full-length polypeptides by peptide synthesis; therefore, the fragments may be employed as intermediates for producing the full length polypeptides.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant procedure, the polypeptides of the present invention may be glycosylated or may be non-glycosylated. Polypeptides of the invention may also include an initial methionine amino acid residue.

Chemical polypeptide synthesis is a rapidly evolving area in the art, and methods of solid phase polypeptide synthesis are well-described in the following references, hereby entirely incorporated by reference (Merrifield, *J. Amer. Chem. Soc.* 85:2149-2154, 1963; Merrifield, *Science* 232: 341-347, 1986; Fields, *Int. J. Polypeptide Prot. Res.* 35, 161, 1990).

Recombinant production of laminin polypeptides can be accomplished according to known method steps. Standard reference works seting forth the general principles of recombinant DNA technology include Watson, *Molecular Biology of the Gene*, Volumes I and II, The Benjamin/Cummings Publishing Company Inc., publisher, Menlo Park, Calif. 1987; Ausubel et al, eds., *Current Protocols in Molecular Biology*, Wiley Interscience, publisher, New York, N.Y. 1987; 1992; and Sambrook et al, *Molecular Cloning: A Laboratory Manual*, Second Edition, Cold Spring Harbor Laboratory, publisher, Cold Spring Harbor, N.Y. 1989, the entire contents of which references are herein incorporated by reference.

The polypeptides of the present invention may also be utilized as research reagents and materials for discovery of treatments and diagnostics for human diseases.

Antibodies

Antibodies generated against the polypeptides corresponding to specific sequences recognizing the laminin fragments of the present invention which bind Aβ or other amyloid proteins can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide. Preferred embodiments include, but are not limited to, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, and fragments thereof, as well as polypeptides which have at least 70% similarity (preferably 70% identity) and more preferably a 90% similarity (more preferably a 90% identity) to the polypeptides described above.

The term "antibody" is meant to include polyclonal antibodies, monoclonal antibodies, chimeric antibodies, anti-idiotypic antibodies to antibodies specific for laminin-derived protein fragments or polypeptides of the present invention.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. For preparation of monoclonal antibodies, any technique which provides antibodies produced by continuous cell line cultures can be used. Examples include the hybridoma technique (Kohler and Milstein, *Nature* 256:495-497, 1975), the trioma technique, the human B-cell hybridoma technique (Kozbor et al, *Immunology Today* 4:72, 1983), and the EBV-hybridoma technique to produce human monoclonal antibodies (Cole et al, in *Monoclonal Antibodies and Cancer Therapy*, Alan R. Liss, Inc., pp. 77-96, 1985). Such antibodies may be of any immunoglobulin class including IgG, IgM, IgE, IgA, GILD and any subclass thereof.

Chimeric antibodies are molecules different portions of which are derived from different animal species, such as those having variable region derived from a murine monoclonal antibody and a human immunoglobulin constant region, which are primarily used to reduce immunogenicity in application and to increase yields in production. Chimeric antibodies and methods for their production are known in the art (ex. Cabilly et al, *Proc. Natl. Acad. Sci. U.S.A* 81:3273-3277, 1984; Harlow and Lane: *Antibodies: A Laboratory Manual*, Cold Spring Harbor Laboratory 1988).

An anti-idiotypic antibody is an antibody which recognizes unique determinants generally associated with the antigen-binding site of an antibody. An anti-iodiotypic antibody can be prepared by immunizing an animal of the same species and genetic type (e.g., mouse strain) as the source of the monoclonal antibody with the monoclonal antibody to which an anti-iodiotypic antibody is being prepared. The immunized animal will recognize and respond to the idiotypic determinants of the immunizing antibody by producing an antibody to these idiotypic determinants (the anti-idiotypic antibody). See, for example, U.S. Pat. No. 4,699,880, which is herein incorporated by reference.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al, *J. Nucl. Med.* 24:316-325, 1983).

The antibodies or fragments of antibodies, useful in the present invention may be used to quantitatively or qualitatively detect laminin or laminin-derived fragments in a sample or to detect presence of cells which express a laminin polypeptide of the present invention. This can be accomplished by immunofluorescence techniques employing a fluorescently labeled antibody coupled with light microscopic, flow cytometric or fluorometric detection.

One of the ways in which a laminin fragment antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric, or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colometric methods which employ a chromogenic substrate for the enzyme. Detection can be accomplished by colometric methods which employ a chromogenic substrate for the enzyme. Detection can also be accomplished by visual comparison of the extent of enzymatic reaction of a substrate with similarly prepared standards (see Harlow and Lane, *Antibodies: A Laboratory Manual*, Cold Spring Harbor Laboratory 1988; Ausubel et al, eds., *Current Protocols in Molecular Biology*, Wiley Interscience, N.Y. 1987, 1992).

Detection may be accomplished using any of a variety of other immunoassays. For example, by radiolabeling of the antibodies or antibody fragments, it is possible to detect R-PTPase through the use of a radioimmunoassay (RIA). A good description of RIA may be found in *Laboratory Techniques and Biochemistry in Molecular Biology*, by Work et al, North Holland Publishing Company, NY (1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also possible to label a laminin fragment polypeptide antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg., U.S.A.).

The antibody can also be detectably labeled using fluorescence emitting metals such as $^{152}$EU, or other of the lanthanide series. These metals can be attached to the antibody using such metal groups as diethylenetriamine pentaacetic acid (EDTA).

The antibody can also be detectably labeled by coupling it to a chemiluminescent compound. The presence of the chemiluminescent-tagged antibody is then determined by detecting the presence of luminescence that arises during the course of a chemical reaction, Examples of particularly useful chemiluminescent labeling compounds are luminol, isoluminol, theromatic acridinium ester, imidazole, acridinium salt, and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibodies (or fragments thereof) useful in the present invention may be employed histologically, as in immunofluorescence or immunoelectron microscopy, for in situ detection of a laminin fragment of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of a laminin fragment polypeptide but also its distribution on the examined tissue. Using the present invention, those of ordinary skill will readily perceive that any of a wide variety of histological methods (such as staining procedures) can be modified in order to achieve such in situ detection.

In accordance with yet a further aspect of the present invention there are provided antibodies against laminin, laminin fragments and/or laminin-derived polypeptides which interact with Aβ or other amyloid proteins, or derivatives thereof. These antibodies can be used for a number of important diagnostic and/or therapeutic applications as described herein. In one aspect of the invention, polyclonal and/or monoclonal antibodies made against laminin, laminin fragments and/or laminin-derived polypeptides which bind Aβ or other amyloid proteins, may be utilized for Western blot analysis (using standard Western blotting techniques knowledgeable to those skilled in the art) to detect the presence of amyloid protein-binding laminin fragments or amyloid protein-binding laminin polypeptides in human tissues and in tissues of other species. Western blot analysis can also be used to determine the apparent size of each amyloid protein-binding laminin fragment. In addition, Western blotting following by scanning densitometry (known to those skilled in the art) can be used to quantitate and compare levels of each of the laminin fragments in tissue samples, biological fluids or biopsies obtained from individuals with specific diseases (such as the amyloid diseases) in comparison to tissue samples, biological fluids or biopsies obtained from normal individuals or controls. Biological fluids, include, but are not limited to, blood, plasma, serum, cerebrospinal fluid, sputum, saliva, urine and stool.

In yet another aspect of the invention, polyclonal and/or monoclonal antibodies made against laminin, laminin fragments and/or laminin-derived peptides which bind Aβ or other amyloid proteins, can be utilized for immunoprecipitation studies (using standard immunoprecipitation techniques known to one skilled in the art) to detect laminin, laminin fragments and/or laminin-derived peptides which bind Aβ or other amyloid proteins, in tissues, cells and/or biological fluids. Use of the laminin, laminin fragment and/or laminin-derived peptide antibodies for immunoprecipitation studies can also be quantitated to determine relative levels of laminin, laminin fragments and/or laminin-derived peptides which interact with Aβ or other amyloid proteins, in tissues, cells and/or biological fluids. Quantitative immunoprecipitation can be used to compare levels of laminin, laminin fragments and/or laminin amyloid protein-binding peptides in tissue samples, biological fluids or biopsies obtained from individuals with specific diseases (such as the amyloid diseases) in comparison to tissue samples, biological fluids or biopsies obtained from normal individuals or controls.

Therapeutic Applications

Yet another aspect of the present invention is to make use of laminin, laminin fragments and/or laminin-derived polypeptides as amyloid inhibitory therapeutic agents. The laminin-derived peptide sequences or fragments can be synthesized utilizing standard techniques (ie. using an automated synthesizer). Laminin, laminin fragments and/or laminin-derived polypeptides which bind Aβ or other amyloid proteins, can be used as potential blocking therapeutics for the interaction of laminin in a number of biological processes and diseases (such as in the amyloid diseases described above). In a preferred embodiment, specific peptides made against the amino acid sequence of laminin contained within the ~55 kDa laminin fragment (i.e. globular repeats within the laminin A chain; SEQ ID NO 3) described in the present invention, may be used to aid in the inhibition of amyloid formation, deposition, accumulation, and/or persistence in a given patient. Likewise, in another preferred embodiment anti-idiotypic antibodies made against laminin, laminin fragments and/or laminin-derived polypeptides (as described above) may be given to a human patient as potential blocking antibodies to disrupt continued amyloid formation, deposition, accumulation and/or persistence in the given patient.

Preparations of laminin-derived polypeptides for parenteral administration include sterile aqueous or non-aqueous solutions, suspensions, and emulsions, which may contain axillary agents or excipients which are known in the art. Pharmaceutical compositions such as tablets, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art.

In yet another aspect of the invention, laminin, laminin fragments and/or laminin-derived polypeptides may be used as an effective therapy to block amyloid formation, deposition, accumulation and/or persistence as observed in the amyloid diseases. For example, the invention includes a pharmaceutical composition for use in the treatment of amyloidoses comprising a pharmaceutically effective amount of a laminin, laminin fragment and/or laminin-derived polypeptide anti-idiotypic antibody and a pharmaceutically acceptable carrier. The compositions may contain the laminin, laminin fragments and/or laminin-derived polypeptide anti-idiotypic antibody, either unmodified, conjugated to a potentially therapeutic compound, conjugated to a second protein or protein portion or in a recombinant form (ie. chimeric or bispecific laminin, laminin fragment and/or laminin polypeptide antibody). The compositions may additionally include other antibodies or conjugates. The antibody compositions of the invention can be administered using conventional modes of administration including, but not limited to, topical, intravenous, intra-arterial, intraperitoneal, oral, intralymphatic, intramuscular or intralumbar. Intravenous administration is preferred. The compositions of the invention can be a variety of dosage forms, with the preferred form depending upon the mode of administration and the therapeutic application. Optimal dosage and modes of administration for an individual patient can readily be determined by conventional protocols.

Laminin, laminin-derived protein fragments, and laminin-derived polypeptides, or antibodies of the present invention may be administered by any means that achieve their intended purpose, for example, to treat laminin involved pathologies, such as Alzheimer's disease and other amyloid diseases, or other related pathologies, using a laminin-derived polypeptide described herein, in the form of a pharmaceutical composition.

For example, administration of such a composition may be by various parenteral routes such as subcutaneous, intravenous, intradermal, intramuscular, intraperitoneal, intranasal, transdermal or buccal routes. Alternatively, or concurrently, administration may be by the oral route. Parenteral administration can be by bolus injection or by gradual perfusion over time.

A preferred mode of using a laminin-derived polypeptide, or antibody pharmaceutical composition of the present invention is by oral administration or intravenous application.

A typical regimen for preventing, suppressing or treating laminin-involved pathologies, such as Alzheimer's disease amyloidosis, comprises administration of an effective amount of laminin-derived polypeptides, administered over a period of one or several days, up to and including between one week and about 24 months.

It is understood that the dosage of the laminin-derived polypeptides of the present invention administered in vivo or in vitro will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The total dose required for each treatment may be administered by multiple doses or in a single dose. A laminin-derived polypeptide may be administered alone or in conjunction with other therapeutics directed to laminin-involved pathologies, such as Alzheimer's disease or amyloid diseases, as described herein.

Effective amounts of a laminin-derived polypeptide or composition, which may also include a laminin-fragment derived antibody, are about 0.01 µg to about 100 mg/kg body weight, and preferably from about 10 µg to about 50 mg/kg body weight, such as 0.05, 0.07, 0.09, 0.1, 0.5, 0.7, 0.9., 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain axillary agents or excipients which are known in the art. Pharmaceutical compositions comprising at least one laminin-derived polypeptide, such as 1-10 or 1, 2, 3, 4, 5, 6, 7, 8, 9, or 10 laminin-derived polypeptides, of the present invention may include all compositions wherein the laminin-derived polypeptide is contained in an amount effective to achieve its intended purpose. In addition to at least one laminin-derived polypeptide, a pharmaceutical composition may contain suitable pharmaceutically acceptable carriers, such as excipients, carriers and/or axillaries which facilitate processing of the active compounds into preparations which can be used pharmaceutically.

Pharmaceutical compositions comprising at least one laminin-derived polypeptide or antibody may also include suitable solutions for administration intravenously, subcutaneously, dermally, orally, mucosally, rectally or may by injection or orally, and contain from about 0.01 to 99 percent, preferably about 20 to 75 percent of active component (i.e. polypeptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

The laminin, laminin-derived protein fragments, and laminin-derived polypeptides for Alzheimer's disease and other central nervous system amyloidoses may be optimized to cross the blood-brain barrier. Methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, laminin, laminin-derived protein fragments, and laminin-derived polypeptides may be directly administered to the cerebrospinal fluid by intraventricular injection. In a specific embodiment, it may be desirable to administer laminin, laminin-derived protein fragments, and laminin-derived polypeptides locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment laminin, laminin-derived protein fragments, and laminin-derived polypeptides may be delivered in a controlled release system, such as an osmotic pump. In yet another embodiment, a controlled release system can be placed in proximity to the therapeutic target, ie. the brain, thus requiring only a fraction of the systemic dose.

In yet another aspect of the present invention, peptidomimetic compounds modelled from laminin, laminin fragments and/or laminin-derived polypeptides identified as binding Aβ or other amyloid proteins, may serve as potent inhibitors of amyloid formation, deposition, accumulation and/or persistence in Alzheimer's disease and other amyloidoses. Peptidomimetic modelling is implemented by standard procedures known to those skilled in the art.

In yet another aspect of the present invention, compounds that mimic the 3-dimensional Aβ binding site on laminin using computer modelling, may serve as potent inhibitors of amyloid formation, deposition, accumulation and/or persistence in Alzheimer's disease and other amyloidoses. Design and production of such compounds using computer modelling technologies is implemented by standard procedures known to those skilled in the art.

Recombinant DNA technology, including human gene therapy, has direct applicability to the laminin proteins and their fragments, of this invention. One skilled in the art can take the peptide sequences disclosed herein and create corresponding nucleotide sequences that code for the corresponding peptide sequences. These sequences can be cloned into vectors such as retroviral vectors, and the like. These vectors can, in turn, be transfected into human cells such as hepatocytes or fibroblasts, and the like. Such transfected cells can be introduced into humans to treat amyloid diseases. Alternatively, the genes can be introduced into the patients directly. The basic techniques of recombinant DNA technology are known to those of ordinary skill in the art and are disclosed in *Recombinant DNA* Second Edition, Watson, et al., W. H. Freeman and Company, New York, 1992, which is hereby incorporated by reference.

Diagnostic Applications

Another aspect of the invention is to provide polyclonal and/or monoclonal antibodies against laminin, laminin fragments and/or laminin-derived polypeptides which bind Aβ or other amyloid proteins, which would be utilized to specifically detect laminin, laminin fragments and/or laminin-derived peptides in human tissues and/or biological fluids. In one preferred embodiment, polyclonal or monoclonal antibodies made against a peptide portion or fragment of laminin, can be used to detect and quantify laminin, laminin fragments and/or laminin-derived polypeptides in human tissues and/or biological fluids. Polyclonal and/or monoclonal peptide antibodies can also be utilized to specifically detect laminin fragments and/or laminin-derived polypeptides in human tissues and/or biological fluids. In a preferred embodiment, a polyclonal or monoclonal antibody made specifically against a peptide portion or fragment of ~55 kDa elastase-resistant protein which binds Aβ (as described herein), can be used to detect and quantify this laminin fragment in human tissues and/or biological fluids. In another preferred embodiment, a polyclonal or monoclonal antibody made specifically against a peptide portion or fragment of ~130 kDa laminin-derived protein which is present in human biological fluids and binds Aβ (as described herein), can be used to detect and quantify this laminin fragment in human tissues and/or biological fluids. Other preferred embodiments include, but are not limited to, making polyclonal or monoclonal antibodies made specifically against a peptide portion or fragment of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, as well as polypeptides which have at least 70% similarity (preferably 70% identity) and more preferably a 90% similarity (more preferably a 90% identity) to the polypeptides described above.

For detection of laminin fragments and/or laminin-derived polypeptides described above in human tissues, cells, and/or in cell culture, the polyclonal and/or monoclonal antibodies can be utilized using standard immunohistochemical and immunocytochemical techniques, known to one skilled in the art.

For detection and quantitation of laminin, laminin fragments and/or laminin-derived polypeptides in biological fluids, including cerebrospinal fluid, blood, plasma, serum, urine, sputum, and/or stool, various types of ELISA assays can be utilized, known to one skilled in the art. An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier, and a quantity of detectable labeled soluble antibody is added to permit detection and/or quantitation of the ternary complex formed between solid-phase antibody, antigen, and labeled antibody.

In a preferred embodiment, a "sandwich" type of ELISA can be used. Using this preferred method a pilot study is first implemented to determine the quantity of binding of each laminin-fragment monoclonal antibody to microtiter wells. Once this is determined, aliquots (usually in 40 μl of TBS; pH 7.4) of the specific laminin-fragment antibody are allowed to bind overnight to microtiter wells (Maxisorb C plate from Nunc) at 4° C. A series of blank wells not containing any laminin-fragment specific monoclonal antibody are also utilized as controls. The next day, non-bound monoclonal antibody is shaken off the microtiter wells. All of the microtiter wells (including the blank wells) are then blocked by incubating for 2 hours with 300 μl of Tris-buffered saline containing 0.05% Tween-20 (TTBS) plus 2% bovine serum albumin, followed by 5 rinses with TTBS. 200 μl of cerebrospinal fluid, blood, plasma, serum, urine, sputum, and/or stool and/or any other type of biological sample is then diluted (to be determined empirically) in TTBS containing 2% bovine serum albumin and placed in wells (in triplicate) containing bound laminin-fragment antibody (or blank) and incubated for 2 hours at room temperature. The wells are then washed 5 times with TTBS. A second biotinylated-monoclonal antibody against the same laminin-derived fragment (but which is against a different epitope) is then added to each well (usually in 40 μl of TBS; pH 7.4) and allowed to bind for 2 hours at room temperature to any laminin-fragment captured by the first antibody. Following incubation, the wells are washed 5 times with TTBS. Bound materials are then detected by incubating with 100 μl of peroxidase-avidin complex (1:250 dilution in TTBS with 0.1% BSA) for 1 hour on a rotary shaker. After 5 washes with TTBS, a substrate solution (100 μl, OPD-Sigma Fast from Sigma Chemical Co., St. Louis, Mo., USA) is added and allowed to develop significant color (usually 8-10 minutes). The reaction is stopped with 50 μl of 4N sulfuric acid and read on a standard spectrophotometer at 490 nm. This ELISA can be utilized to determine differences in specific laminin fragments (and/or Aβ-binding laminin fragments) in biological fluids which can serve as a diagnostic marker to follow the progression on a live patient during the progression of disease (ie. monitoring of amyloid disease as an example). In addition, quantitative changes in laminin fragments can also serve as a prognostic indicator monitoring how a live patient will respond to treatment which targets a given amyloid disease such as Alzheimer's disease. Such assays can be provided in a kit form.

A competition assay may also be employed wherein antibodies specific to laminin, laminin fragments and/or laminin-derived polypeptides are attached to a solid support and labelled laminin, laminin fragments and/or laminin-derived polypeptides and a sample derived from a host are passed over the solid support and the amount of label detected attached to the solid support can be correlated to the quantity of laminin, laminin fragments and/or laminin-derived polypeptides in the sample. This standard technique is known to one skilled in the art.

Another object of the present invention is to use laminin, laminin fragments and/or laminin-derived polypeptides, in conjunction with laminin, laminin fragment and/or laminin-derived peptide antibodies, in an ELISA assay to detect potential laminin, laminin fragment and/or laminin-derived peptide autoantibodies in human biological fluids. Such a diagnostic assay may be produced in a kit form. In a preferred embodiment, peptides containing the sequences of laminin, laminin-derived fragments and laminin-derived polypeptides as in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11, as well as polypeptides which have at least 70% similarity (preferably 70% identity) and more preferably a 90% similarity (more preferably a 90% identity) to the polypeptides described above, will be used to initially bind to microtiter wells in an ELISA plate. A pilot study is first implemented to determine the quantity of binding of each laminin fragment polypeptide to microtiter wells. Once this is determined, aliquots (usually 1-2 µg in 40 µl of TBS; pH 7.4) of specific laminin fragment polypeptides (as described herein) are allowed to bind overnight to microtiter wells (Maxisorb C plate from Nunc) at 4° C. All the microtiter wells (including blank wells without the laminin fragment polypeptides) are blocked by incubating for 2 hours with 300 µl of Tris-buffered saline (pH 7.4) with 0.05% Tween-20 (TTBS), containing 2% albumin. This is followed by 5 rinses with TTBS. The patients' biological fluids (i.e., cerebrospinal fluid, blood, plasma, serum, sputum, urine, and/or stool) are then utilized and 200 µl are diluted (to be determined empirically) with TTBS containing 2% bovine serum albumin, and placed in microtiter wells (in triplicate) containing a specific laminin fragment polypeptide or blank wells (which do not contain peptide), and are incubated at 1.5 hours at room temperature. Any autoantibodies present in the biological fluids against the laminin fragment will bind to the substrate bound laminin fragment polypeptide (or fragments thereof). The wells are then rinsed by washing 5 times with TTBS. 100 µl of biotinylated polyclonal goat anti-human IgGs (Sigma Chemical company, St. Louis, Mo., USA), diluted 1:500 in TTBS with 0.1% bovine serum albumin, is then aliquoted into each well. Bound materials are detected by incubating with 100 µl of peroxidase-avidin complex (1:250 dilution in TTBS with 0.1% bovine serum albumin) for 1 hour on a rotary shaker. Following 5 washes with TTBS, substrate solution (100 µl, OPD-Sigma Fast from Sigma Chemical Company, St. Louis, Mo., USA) is added and allowed to develop significant color (usually 8-10 minutes). The reaction is stopped with 50 µl of 4N sulfuric acid added to each well and read on a standard spectrophotometer at 490 nm. This assay system can be utilized to not only detect the presence of autoantibodies against laminin fragments in biological fluids, but also to monitor the progression of disease by following elevation or diminution of laminin fragment autoantibody levels. It is believed that patients demonstrating excessive laminin fragment formation, deposition, accumulation and/or persistence as may be observed in the amyloid diseases, will also carry autoantibodies against the laminin fragments in their biological fluids. Various ELISA assay systems, knowledgeable to those skilled in the art, can be used to accurately monitor the degree of laminin fragments in biological fluids as a potential diagnostic indicator and prognostic marker for patients during the progression of disease (ie. monitoring of an amyloid disease for example). Such assays can be provided in a kit form. In addition, quantitative changes in laminin fragment autoantibody levels can also serve as a prognostic indicator monitoring how a live patient will respond to treatment which targets a given amyloid disease.

Other diagnostic methods utilizing the invention include diagnostic assays for measuring altered levels of laminin, laminin fragments and/or laminin-derived polypeptides in various tissues compared to normal control tissue samples. Assays used to detect levels of laminin, laminin fragments and/or laminin-derived polypeptides in a sample derived from a host are well-known to those skilled in the art and included radioimmunoassays, competitive-binding assays, Western blot analysis and preferably ELISA assays (as described above).

Yet another aspect of the present invention is to use the antibodies recognizing laminin, laminin fragments and/or laminin-derived polypeptides for labellings, for example, with a radionucleotide, for radioimaging or radioguided surgery, for in vivo diagnosis, and/or for in vitro diagnosis. In one preferred embodiment, radiolabelled peptides or antibodies made (by one skilled in the art) against laminin, laminin fragments and/or laminin-derived polypeptides may be used as minimally invasive techniques to locate laminin, laminin fragments and/or laminin-derived polypeptides, and concurrent amyloid deposits in a living patient. These same imaging techniques could then be used at regular intervals (ie. every 6 months) to monitor the progression of the amyloid disease by following the specific levels of laminin, laminin fragments and/or laminin-derived polypeptides.

Yet another aspect of the present invention is to provide a method which can evaluate a compound's ability to alter (diminish or eliminate) the affinity of a given amyloid protein (as described herein) or amyloid precursor protein, to laminin, laminin-derived fragments or laminin-derived polypeptides. By providing a method of identifying compounds which affect the binding of amyloid proteins, or amyloid precursor proteins to such laminin-derived fragments, the present invention is also useful in identifying compounds which can prevent or impair such binding interaction. Thus, compounds can be identified which specifically affect an event linked with the amyloid formation, amyloid deposition, and/or amyloid persistence condition associated with Alzheimer's disease and other amyloid diseases as described herein.

According to one aspect of the invention, to identify for compounds which allow the interaction of amyloid proteins or precursor proteins to laminin-derived fragments or laminin polypeptides, either amyloid or laminin fragments are immobilized, and the other of the two is maintained as a free entity. The free entity is contacted with the immobilized entity in the presence of a test compound for a period of time sufficient to allow binding of the free entity to the immobilized entity, after which the unbound free entity is removed. Using antibodies which recognize the free entity, or other means to detect the presence of bound components, the amount of free entity bound to immobilized entity can be measured. By performing this assay in the presence of a series of known concentrations of test compound and, as a control, the complete absence of test compound, the effectiveness of the test compound to allow binding of free entity to immobilized entity can be determined and a quantitative determination of the effect of the test compound on the affinity of free entity to immobilized entity can be made. By comparing the binding affinity of the amyloid-laminin fragment complex in the presence of a test compound to the binding affinity of the amyloid-laminin fragment complex in the absence of a test compound, the ability of the test compound to modulate the binding can be determined.

In the case in which the amyloid is immobilized, it is contacted with free laminin-derived fragments or polypeptides, in the presence of a series of concentrations of test compound. As a control, immobilized amyloid is contacted with free laminin-derived polypeptides, or fragments thereof in the absence of the test compound. Using a series of concentrations of laminin-derived polypeptides, the dissociation constant ($K_d$) or other indicators of binding affinity of amyloid-laminin fragment binding can be determined. In the assay, after the laminin-derived polypeptides or fragments thereof is placed in contact with the immobilized amyloid for a sufficient time to allow binding, the unbound laminin polypeptides are removed. Subsequently, the level of laminin fragment-amyloid binding can be observed. One method uses laminin-derived fragment antibodies, as described in the invention, to detect the amount of specific laminin fragments bound to the amyloid or the amount of free laminin fragments remaining in solution. This information is used to determine first qualitatively whether or not the test compound can allow continued binding between laminin-derived fragments and amyloid. Secondly, the data collected from assays performed using a series of test compounds at various concentrations, can be used to measure quantitatively the binding affinity of the laminin fragment-amyloid complex and thereby determine the effect of the test compound on the affinity between laminin fragments and amyloid. Using this information, compounds can be identified which do not modulate the binding of specific laminin fragments to amyloid and thereby allow the laminin-fragments to reduce the amyloid formation, deposition, accumulation and/or persistence, and the subsequent development and persistence of amyloidosis.

Therefore a kit for practicing a method for identifying compounds useful which do not alter laminin, laminin-derived fragments or laminin-derived polypeptides to an immobilized amyloid protein, said kit comprising a) a first container having amyloid protein immobilized upon the inner surface, b) a second container which contains laminin, laminin-derived fragments or laminin-derived polypeptides dissolved in solution, c) a third container which contains antibodies specific for said laminin, laminin-derived fragments or laminin-derived polypeptides, said antibodies dissolved in solution, and d) a fourth container which contains labelled antibodies specific for laminin, laminin-derived fragments or laminin-derived polypeptides, said antibodies dissolved in solution.

We claim:

1. A method for inhibiting or reducing beta-amyloid protein fibril formation, deposition or accumulation in vitro, the method comprising administering to vitro a cell culture containing beta-amyloid protein, an effective amount of a polypeptide consisting of SEQ ID NO: 3, the amount administered effective for the inhibition or reduction of the beta-amyloid protein fibril formation, deposition or accumulation, as compared to cell culture containing beta-amyloid protein in absence of polypeptide SEQ ID NO: 3.

2. The method of claim 1 wherein the polypeptide SEQ ID NO: 3 is synthetic.

3. The method of claim 1 wherein the polypeptide SEQ ID NO: 3 is taken from a globular domain repeat within a laminin A chain.

4. The method of claim 3, wherein the polypeptide of SEQ ID NO: 3 is taken from a 4$^{th}$ globular domain repeat within human laminin A chain.

* * * * *

UNITED STATES PATENT AND TRADEMARK OFFICE
CERTIFICATE OF CORRECTION

| | | |
|---|---|---|
| PATENT NO. | : 7,314,724 B2 | |
| APPLICATION NO. | : 09/938275 | |
| DATED | : January 1, 2008 | |
| INVENTOR(S) | : Castillo et al. | |

It is certified that error appears in the above-identified patent and that said Letters Patent is hereby corrected as shown below:

Please insert the following statement in Column 1 after line 8:

--This invention was made with Government support under 1 R43 AG17787-01 awarded by the National Institute on Aging. The Government has certain rights in the invention.--

Signed and Sealed this

Third Day of March, 2009

JOHN DOLL
*Acting Director of the United States Patent and Trademark Office*

SEQUENCE LISTING

```
<160> NUMBER OF SEQ ID NOS: 11

<210> SEQ ID NO 1
<211> LENGTH: 11
<212> TYPE: PRT
<213> ORGANISM: Mus Musculus
<300> PUBLICATION INFORMATION:
<308> DATABASE ACCESSION NUMBER: Swissprot P19137
<309> DATABASE ENTRY DATE: 1990-11-01

<400> SEQUENCE: 1

Leu His Arg Glu His Gly Glu Leu Pro Pro Glu
1               5                   10

<210> SEQ ID NO 2
<211> LENGTH: 177
<212> TYPE: PRT
<213> ORGANISM: Mus Musculus
<300> PUBLICATION INFORMATION:
<308> DATABASE ACCESSION NUMBER: Swissprot P19137
<309> DATABASE ENTRY DATE: 1990-11-01

<400> SEQUENCE: 2

Leu Gln Val Gln Leu Ser Ile Arg Thr Phe Ala Ser Ser Gly Leu Ile
1               5                   10                  15

Tyr Tyr Val Ala His Gln Asn Gln Met Asp Tyr Ala Thr Leu Gln Leu
            20                  25                  30

Gln Glu Gly Arg Leu His Phe Met Phe Asp Leu Gly Lys Gly Arg Thr
        35                  40                  45

Lys Val Ser His Pro Ala Leu Leu Ser Asp Gly Lys Trp His Thr Val
    50                  55                  60

Lys Thr Glu Tyr Ile Lys Arg Lys Ala Phe Met Thr Val Asp Gly Gln
65                  70                  75                  80
```

-continued

```
Glu Ser Pro Ser Val Thr Val Val Gly Asn Ala Thr Thr Leu Asp Val
                85                  90                  95

Glu Arg Lys Leu Tyr Leu Gly Leu Pro Ser His Tyr Arg Ala Arg
            100                 105                 110

Asn Ile Gly Thr Ile Thr His Ser Ile Pro Ala Cys Ile Gly Glu Ile
            115                 120                 125

Met Val Asn Gly Gln Gln Leu Asp Lys Asp Arg Pro Leu Ser Ala Ser
        130                 135                 140

Ala Val Asp Arg Cys Tyr Val Ala Gln Glu Gly Thr Phe Phe Glu
145                 150                 155                 160

Gly Ser Gly Tyr Ala Ala Leu Val Lys Glu Gly Tyr Lys Val Arg Leu
                165                 170                 175

Asp

<210> SEQ ID NO 3
<211> LENGTH: 177
<212> TYPE: PRT
<213> ORGANISM: Homo Sapiens
<300> PUBLICATION INFORMATION:
<308> DATABASE ACCESSION NUMBER: Swissprot P25391
<309> DATABASE ENTRY DATE: 1992-05-01

<400> SEQUENCE: 3

Leu Ser Val Glu Leu Ser Ile Arg Thr Phe Ala Ser Ser Gly Leu Ile
1               5                   10                  15

Tyr Tyr Met Ala His Gln Asn Gln Ala Asp Tyr Ala Val Leu Gln Leu
            20                  25                  30

His Gly Gly Arg Leu His Phe Met Phe Asp Leu Gly Lys Gly Arg Thr
        35                  40                  45

Lys Val Ser His Pro Ala Leu Leu Ser Asp Gly Lys Trp His Thr Val
    50                  55                  60

Lys Thr Asp Tyr Val Lys Arg Lys Gly Phe Ile Thr Val Asp Gly Arg
65                  70                  75                  80

Glu Ser Pro Met Val Thr Val Val Gly Asp Gly Thr Met Leu Asp Val
                85                  90                  95

Glu Gly Leu Phe Tyr Leu Gly Gly Leu Pro Ser Gln Tyr Gln Ala Arg
            100                 105                 110

Lys Ile Gly Asn Ile Thr His Ser Ile Pro Ala Cys Ile Gly Asp Val
            115                 120                 125

Thr Val Asn Ser Lys Gln Leu Asp Lys Asp Ser Pro Val Ser Ala Phe
        130                 135                 140

Thr Val Asn Arg Cys Tyr Ala Val Ala Gln Glu Gly Thr Tyr Phe Asp
145                 150                 155                 160

Gly Ser Gly Tyr Ala Ala Leu Val Lys Glu Gly Tyr Lys Val Gln Ser
                165                 170                 175

Asp

<210> SEQ ID NO 4
<211> LENGTH: 3084
<212> TYPE: PRT
<213> ORGANISM: Mus Musculus
<300> PUBLICATION INFORMATION:
<308> DATABASE ACCESSION NUMBER: Swissprot P19137
<309> DATABASE ENTRY DATE: 1990-11-01

<400> SEQUENCE: 4

Met Arg Gly Ser Gly Thr Gly Ala Ala Leu Leu Val Leu Leu Ala Ser
```

-continued

```
  1               5                   10                  15
Val Leu Trp Val Thr Val Arg Ser Gln Gln Arg Gly Leu Phe Pro Ala
            20                  25                  30

Ile Leu Asn Leu Ala Thr Asn Ala His Ile Ser Ala Asn Ala Thr Cys
            35                  40                  45

Gly Glu Lys Gly Pro Glu Met Phe Cys Lys Leu Val Glu His Val Pro
50                      55                  60

Gly Arg Pro Val Arg His Ala Gln Cys Arg Val Cys Asp Gly Asn Ser
65                      70                  75                  80

Thr Asn Pro Arg Glu Arg His Pro Ile Ser His Ala Ile Asp Gly Thr
                85                  90                  95

Asn Asn Trp Trp Gln Ser Pro Ser Ile Gln Asn Gly Arg Glu Tyr His
                100                 105                 110

Trp Val Thr Val Thr Leu Asp Leu Arg Gln Val Phe Gln Val Ala Tyr
                115                 120                 125

Ile Ile Ile Lys Ala Ala Asn Ala Pro Arg Pro Gly Asn Trp Ile Leu
            130                 135                 140

Glu Arg Ser Val Asp Gly Val Lys Phe Lys Pro Trp Gln Tyr Tyr Ala
145                 150                 155                 160

Val Ser Asp Thr Glu Cys Leu Thr Arg Tyr Lys Ile Thr Pro Arg Arg
                165                 170                 175

Gly Pro Pro Thr Tyr Arg Ala Asp Asn Glu Val Ile Cys Thr Ser Tyr
                180                 185                 190

Tyr Ser Lys Leu Val Pro Leu Glu His Gly Glu Ile His Thr Ser Leu
            195                 200                 205

Ile Asn Gly Arg Pro Ser Ala Asp Pro Ser Pro Gln Leu Leu Glu
            210                 215                 220

Phe Thr Ser Ala Arg Tyr Ile Arg Leu Arg Leu Gln Arg Ile Arg Thr
225                 230                 235                 240

Leu Asn Ala Asp Leu Met Thr Leu Ser His Arg Asp Leu Arg Asp Leu
                245                 250                 255

Asp Pro Ile Val Thr Arg Arg Tyr Tyr Tyr Ser Ile Lys Asp Ile Ser
                260                 265                 270

Val Gly Gly Met Cys Ile Cys Tyr Gly His Ala Ser Ser Cys Pro Trp
            275                 280                 285

Asp Glu Glu Ala Lys Gln Leu Gln Cys Gln Cys Glu His Asn Thr Cys
            290                 295                 300

Gly Glu Ser Cys Asp Arg Cys Cys Pro Gly Tyr His Gln Gln Pro Trp
305                 310                 315                 320

Arg Pro Gly Thr Ile Ser Ser Gly Asn Glu Cys Glu Cys Asn Cys
                325                 330                 335

His Asn Lys Ala Lys Asp Cys Tyr Tyr Asp Ser Ser Val Ala Lys Glu
            340                 345                 350

Arg Arg Ser Leu Asn Thr Ala Gly Gln Tyr Ser Gly Gly Val Cys
            355                 360                 365

Val Asn Cys Ser Gln Asn Thr Thr Gly Ile Asn Cys Glu Thr Cys Ile
            370                 375                 380

Asp Gln Tyr Tyr Arg Pro His Lys Val Ser Pro Tyr Asp His Pro
385                 390                 395                 400

Cys Arg Pro Cys Asn Cys Asp Pro Val Gly Ser Leu Ser Ser Val Cys
                405                 410                 415

Ile Lys Asp Asp Arg His Ala Asp Leu Ala Asn Gly Lys Trp Pro Gly
            420                 425                 430
```

-continued

```
Gln Cys Pro Cys Arg Lys Gly Tyr Ala Gly Asp Lys Cys Asp Arg Cys
            435                 440                 445

Gln Phe Gly Tyr Arg Gly Phe Pro Asn Cys Ile Pro Cys Asp Cys Arg
    450                 455                 460

Thr Val Gly Ser Leu Asn Glu Asp Pro Cys Ile Glu Pro Cys Leu Cys
465                 470                 475                 480

Lys Lys Asn Val Glu Gly Lys Asn Cys Asp Arg Cys Lys Pro Gly Phe
                485                 490                 495

Tyr Asn Leu Lys Glu Arg Asn Pro Glu Gly Cys Ser Glu Cys Phe Cys
            500                 505                 510

Phe Gly Val Ser Gly Val Cys Asp Ser Leu Thr Trp Ser Ile Ser Gln
        515                 520                 525

Val Thr Asn Met Ser Gly Trp Leu Val Thr Asp Leu Met Ser Thr Asn
    530                 535                 540

Lys Ile Arg Ser Gln Gln Asp Val Leu Gly His Arg Gln Ile Ser
545                 550                 555                 560

Ile Asn Asn Thr Ala Val Met Gln Arg Leu Thr Ser Thr Tyr Tyr Trp
                565                 570                 575

Ala Ala Pro Glu Ala Tyr Leu Gly Asn Lys Leu Thr Ala Phe Gly Gly
            580                 585                 590

Phe Leu Lys Tyr Thr Val Ser Tyr Asp Ile Pro Val Glu Thr Val Asp
        595                 600                 605

Ser Asp Leu Met Ser His Ala Asp Ile Ile Lys Gly Asn Gly Leu
        610                 615                 620

Thr Ile Ser Thr Arg Ala Glu Gly Leu Ser Leu Gln Pro Tyr Glu Glu
625                 630                 635                 640

Tyr Phe Asn Val Val Arg Leu Val Pro Glu Asn Phe Arg Asp Phe Asn
                645                 650                 655

Thr Arg Arg Glu Ile Asp Arg Asp Gln Leu Met Thr Val Leu Ala Asn
            660                 665                 670

Val Thr His Leu Leu Ile Arg Ala Asn Tyr Asn Ser Ala Lys Met Ala
        675                 680                 685

Leu Tyr Arg Leu Asp Ser Val Ser Leu Asp Ile Ala Ser Pro Asn Ala
        690                 695                 700

Ile Asp Leu Ala Val Ala Ala Asp Val Glu His Cys Glu Cys Pro Gln
705                 710                 715                 720

Gly Tyr Thr Gly Thr Ser Cys Glu Ala Cys Leu Pro Gly Tyr Tyr Arg
                725                 730                 735

Val Asp Gly Ile Leu Phe Gly Gly Ile Cys Gln Pro Cys Glu Cys His
            740                 745                 750

Gly His Ala Ser Glu Cys Asp Ile His Gly Ile Cys Ser Val Cys Thr
        755                 760                 765

His Asn Thr Thr Gly Asp His Cys Glu Gln Cys Leu Pro Gly Phe Tyr
        770                 775                 780

Gly Thr Pro Ser Arg Gly Thr Pro Gly Asp Cys Gln Pro Cys Ala Cys
785                 790                 795                 800

Pro Leu Ser Ile Asp Ser Asn Asn Phe Ser Pro Thr Cys His Leu Thr
                805                 810                 815

Asp Gly Glu Glu Val Val Cys Asp Gln Cys Ala Pro Gly Tyr Ser Gly
            820                 825                 830

Ser Trp Cys Glu Arg Cys Ala Asp Gly Tyr Tyr Gly Asn Pro Thr Val
        835                 840                 845
```

-continued

```
Pro Gly Gly Thr Cys Val Pro Cys Asn Cys Ser Gly Asn Val Asp Pro
    850                 855                 860
Leu Glu Ala Gly His Cys Asp Ser Val Thr Gly Glu Cys Leu Lys Cys
865                 870                 875                 880
Leu Trp Asn Thr Asp Gly Ala His Cys Glu Arg Cys Ala Asp Gly Phe
                885                 890                 895
Tyr Gly Asp Ala Val Thr Ala Lys Asn Cys Arg Ala Cys Asp Cys His
            900                 905                 910
Glu Asn Gly Ser Leu Ser Gly Val Cys His Leu Glu Thr Gly Leu Cys
        915                 920                 925
Asp Cys Lys Pro His Val Thr Gly Gln Gln Cys Asp Gln Cys Leu Ser
    930                 935                 940
Gly Tyr Tyr Gly Leu Asp Thr Gly Leu Gly Cys Val Pro Cys Asn Cys
945                 950                 955                 960
Ser Val Glu Gly Ser Val Ser Asp Asn Cys Thr Glu Gly Gln Cys
                965                 970                 975
His Cys Gly Pro Gly Val Ser Gly Lys Gln Cys Asp Arg Cys Ser His
            980                 985                 990
Gly Phe Tyr Ala Phe Gln Asp Gly Gly Cys Thr Pro Cys Asp Cys Ala
        995                 1000                1005
His Thr Gln Asn Asn Cys Asp Pro Ala Ser Gly Glu Cys Leu Cys Pro
    1010                1015                1020
Pro His Thr Gln Gly Leu Lys Cys Glu Glu Cys Glu Ala Tyr Trp
1025                1030                1035                1040
Gly Leu Asp Pro Glu Gln Gly Cys Gln Ala Cys Asn Cys Ser Ala Val
                1045                1050                1055
Gly Ser Thr Ser Ala Gln Cys Asp Val Leu Ser Gly His Cys Pro Cys
            1060                1065                1070
Lys Lys Gly Phe Gly Gly Gln Ser Cys His Gln Cys Ser Leu Gly Tyr
        1075                1080                1085
Arg Ser Phe Pro Asp Cys Val Pro Cys Gly Cys Asp Leu Arg Gly Thr
    1090                1095                1100
Leu Pro Asp Thr Cys Asp Leu Glu Gln Gly Leu Cys Ser Cys Ser Glu
1105                1110                1115                1120
Asp Ser Gly Thr Cys Ser Cys Lys Glu Asn Val Val Gly Pro Gln Cys
                1125                1130                1135
Ser Lys Cys Gln Ala Gly Thr Phe Ala Leu Arg Gly Asp Asn Pro Gln
            1140                1145                1150
Gly Cys Ser Pro Cys Phe Cys Phe Gly Leu Ser Gln Leu Cys Ser Glu
        1155                1160                1165
Leu Glu Gly Tyr Val Arg Thr Leu Ile Thr Leu Ala Ser Asp Gln Pro
    1170                1175                1180
Leu Leu His Val Val Ser Gln Ser Asn Leu Lys Gly Thr Ile Glu Gly
1185                1190                1195                1200
Val His Phe Gln Pro Pro Asp Thr Leu Leu Asp Ala Glu Ala Val Arg
                1205                1210                1215
Gln His Ile Tyr Ala Glu Pro Phe Tyr Trp Arg Leu Pro Lys Gln Phe
            1220                1225                1230
Gln Gly Asp Gln Leu Leu Ala Tyr Gly Gly Lys Leu Gln Tyr Ser Val
        1235                1240                1245
Ala Phe Tyr Ser Thr Leu Gly Thr Gly Thr Ser Asn Tyr Glu Pro Gln
    1250                1255                1260
Val Leu Ile Lys Gly Gly Arg Ala Arg Lys His Val Ile Tyr Met Asp
```

-continued

```
              1265                1270                1275                1280
        Ala Pro Ala Pro Glu Asn Gly Val Arg Gln Asp Tyr Glu Val Gln Met
                            1285                1290                1295
        Lys Glu Glu Phe Trp Lys Tyr Phe Asn Ser Val Ser Glu Lys His Val
                        1300                1305                1310
        Thr His Ser Asp Phe Met Ser Val Leu Ser Asn Ile Asp Tyr Ile Leu
                    1315                1320                1325
        Ile Lys Ala Ser Tyr Gly Gln Gly Leu Gln Gln Ser Arg Ile Ala Asn
                1330                1335                1340
        Ile Ser Met Glu Val Gly Arg Lys Ala Val Glu Leu Pro Ala Glu Gly
        1345                1350                1355                1360
        Glu Ala Ala Leu Leu Leu Glu Leu Cys Val Cys Pro Pro Gly Thr Ala
                        1365                1370                1375
        Gly His Ser Cys Gln Asp Cys Ala Pro Gly Tyr Tyr Arg Glu Lys Leu
                    1380                1385                1390
        Pro Glu Ser Gly Gly Arg Gly Pro Arg Pro Leu Leu Ala Pro Cys Val
                1395                1400                1405
        Pro Cys Asn Cys Asn Asn His Ser Asp Val Cys Asp Pro Glu Thr Gly
            1410                1415                1420
        Lys Cys Leu Ser Cys Arg Asp His Thr Ser Gly Asp His Cys Glu Leu
        1425                1430                1435                1440
        Cys Ala Ser Gly Tyr Tyr Gly Lys Val Thr Gly Leu Pro Gly Asp Cys
                        1445                1450                1455
        Thr Pro Cys Thr Cys Pro His His Pro Pro Phe Ser Phe Ser Pro Thr
                    1460                1465                1470
        Cys Val Val Glu Gly Asp Ser Asp Phe Arg Cys Asn Ala Cys Leu Pro
                1475                1480                1485
        Gly Tyr Glu Gly Gln Tyr Cys Glu Arg Cys Ser Ala Gly Tyr His Gly
            1490                1495                1500
        Asn Pro Arg Ala Ala Gly Gly Ser Cys Gln Thr Cys Asp Cys Asn Pro
        1505                1510                1515                1520
        Gln Gly Ser Val His Ser Asp Cys Asp Arg Ala Ser Gly Gln Cys Val
                        1525                1530                1535
        Cys Lys Pro Gly Ala Thr Gly Leu His Cys Glu Lys Cys Leu Pro Arg
                    1540                1545                1550
        His Ile Leu Met Glu Ser Asp Cys Val Ser Cys Asp Asp Cys Val
                1555                1560                1565
        Gly Pro Leu Leu Asn Asp Leu Asp Ser Val Gly Asp Ala Val Leu Ser
            1570                1575                1580
        Leu Asn Leu Thr Gly Val Ser Pro Ala Pro Tyr Gly Ile Leu Glu Asn
        1585                1590                1595                1600
        Leu Glu Asn Thr Thr Lys Tyr Phe Gln Arg Tyr Leu Ile Lys Glu Asn
                        1605                1610                1615
        Ala Lys Lys Ile Arg Ala Glu Ile Gln Leu Gly Ile Ala Glu Gln
                    1620                1625                1630
        Thr Glu Asn Leu Gln Lys Glu Leu Thr Arg Val Leu Ala Arg His Gln
                1635                1640                1645
        Lys Val Asn Ala Glu Met Glu Arg Thr Ser Asn Gly Thr Gln Ala Leu
            1650                1655                1660
        Ala Thr Phe Ile Glu Gln Leu His Ala Asn Ile Lys Glu Ile Thr Glu
        1665                1670                1675                1680
        Lys Val Ala Thr Leu Asn Gln Thr Ala Arg Lys Asp Phe Gln Pro Pro
                        1685                1690                1695
```

-continued

Val Ser Ala Leu Gln Ser Met His Gln Asn Ile Ser Ser Leu Leu Gly
            1700                1705                1710

Leu Ile Lys Glu Arg Asn Phe Thr Glu Met Gln Gln Asn Ala Thr Leu
        1715                1720                1725

Glu Leu Lys Ala Ala Lys Asp Leu Leu Ser Arg Ile Gln Lys Arg Phe
        1730                1735                1740

Gln Lys Pro Gln Glu Lys Leu Lys Ala Leu Lys Glu Ala Asn Ser Leu
1745                1750                1755                1760

Leu Ser Asn His Ser Glu Lys Leu Gln Ala Ala Glu Leu Leu Lys
            1765                1770                1775

Glu Ala Gly Ser Lys Thr Gln Glu Ser Asn Leu Leu Leu Leu Val
            1780                1785                1790

Lys Ala Asn Leu Lys Glu Glu Phe Gln Glu Lys Lys Leu Arg Val Gln
            1795                1800                1805

Glu Glu Gln Asn Val Thr Ser Glu Leu Ile Ala Lys Gly Arg Glu Trp
        1810                1815                1820

Val Asp Ala Ala Gly Thr His Thr Ala Ala Gln Asp Thr Leu Thr
1825                1830                1835                1840

Gln Leu Glu His His Arg Asp Glu Leu Leu Leu Trp Ala Arg Lys Ile
            1845                1850                1855

Arg Ser His Val Asp Asp Leu Val Met Gln Met Ser Lys Arg Arg Ala
        1860                1865                1870

Arg Asp Leu Val His Arg Ala Glu Gln His Ala Ser Glu Leu Gln Ser
        1875                1880                1885

Arg Ala Gly Ala Leu Asp Arg Asp Leu Glu Asn Val Arg Asn Val Ser
    1890                1895                1900

Leu Asn Ala Thr Ser Ala Ala His Val His Ser Asn Ile Gln Thr Leu
1905                1910                1915                1920

Thr Glu Glu Ala Glu Met Leu Ala Ala Asp Ala His Lys Thr Ala Asn
            1925                1930                1935

Lys Thr Asp Leu Ile Ser Glu Ser Leu Ala Ser Arg Gly Lys Ala Val
        1940                1945                1950

Leu Gln Arg Ser Ser Arg Phe Leu Lys Glu Ser Val Gly Thr Arg Arg
    1955                1960                1965

Lys Gln Gln Gly Ile Thr Met Lys Leu Asp Glu Leu Lys Asn Leu Thr
        1970                1975                1980

Ser Gln Phe Gln Glu Ser Val Asp Asn Ile Thr Lys Gln Ala Asn Asp
1985                1990                1995                2000

Ser Leu Ala Met Leu Arg Glu Ser Pro Gly Gly Met Arg Glu Lys Gly
            2005                2010                2015

Arg Lys Ala Arg Glu Leu Ala Ala Ala Ala Asn Glu Ser Ala Val Lys
        2020                2025                2030

Thr Leu Glu Asp Val Leu Ala Leu Ser Leu Arg Val Phe Asn Thr Ser
        2035                2040                2045

Glu Asp Leu Ser Arg Val Asn Ala Thr Val Gln Glu Thr Asn Asp Leu
    2050                2055                2060

Leu His Asn Ser Thr Met Thr Thr Leu Leu Ala Gly Arg Lys Met Lys
2065                2070                2075                2080

Asp Met Glu Met Gln Ala Asn Leu Leu Leu Asp Arg Leu Lys Pro Leu
            2085                2090                2095

Lys Thr Leu Glu Glu Asn Leu Ser Arg Asn Leu Ser Glu Ile Lys Leu
        2100                2105                2110

-continued

Leu Ile Ser Arg Ala Arg Lys Gln Ala Ala Ser Ile Lys Val Ala Val
        2115                2120                2125

Ser Ala Asp Arg Asp Cys Ile Arg Ala Tyr Gln Pro Gln Thr Ser Ser
        2130                2135                2140

Thr Asn Tyr Asn Thr Leu Ile Leu Asn Val Lys Thr Gln Glu Pro Asp
2145                2150                2155                2160

Asn Leu Leu Phe Tyr Leu Gly Ser Ser Ser Ser Asp Phe Leu Ala
        2165                2170                2175

Val Glu Met Arg Arg Gly Lys Val Ala Phe Leu Trp Asp Leu Gly Ser
        2180                2185                2190

Gly Ser Thr Arg Leu Glu Phe Pro Glu Val Ser Ile Asn Asn Asn Arg
        2195                2200                2205

Trp His Ser Ile Tyr Ile Thr Arg Phe Gly Asn Met Gly Ser Leu Ser
        2210                2215                2220

Val Lys Glu Ala Ser Ala Ala Glu Asn Pro Pro Val Arg Thr Ser Lys
2225                2230                2235                2240

Ser Pro Gly Pro Ser Lys Val Leu Asp Ile Asn Asn Ser Thr Leu Met
        2245                2250                2255

Phe Val Gly Gly Leu Gly Gly Gln Ile Lys Lys Ser Pro Ala Val Lys
        2260                2265                2270

Val Thr His Phe Lys Gly Cys Met Gly Glu Ala Phe Leu Asn Gly Lys
        2275                2280                2285

Ser Ile Gly Leu Trp Asn Tyr Ile Glu Arg Glu Gly Lys Cys Asn Gly
        2290                2295                2300

Cys Phe Gly Ser Ser Gln Asn Glu Asp Ser Ser Phe His Phe Asp Gly
2305                2310                2315                2320

Ser Gly Tyr Ala Met Val Glu Lys Thr Leu Arg Pro Thr Val Thr Gln
        2325                2330                2335

Ile Val Ile Leu Phe Ser Thr Phe Ser Pro Asn Gly Leu Leu Phe Tyr
        2340                2345                2350

Leu Ala Ser Asn Gly Thr Lys Asp Phe Leu Ser Ile Glu Leu Val Arg
        2355                2360                2365

Gly Arg Val Lys Val Met Val Asp Leu Gly Ser Gly Pro Leu Thr Leu
        2370                2375                2380

Met Thr Asp Arg Arg Tyr Asn Asn Gly Thr Trp Tyr Lys Ile Ala Phe
2385                2390                2395                2400

Gln Arg Asn Arg Lys Gln Gly Leu Leu Ala Val Phe Asp Ala Tyr Asp
        2405                2410                2415

Thr Ser Asp Lys Glu Thr Lys Gln Gly Glu Thr Pro Gly Ala Ala Ser
        2420                2425                2430

Asp Leu Asn Arg Leu Glu Lys Asp Leu Ile Tyr Val Gly Gly Leu Pro
        2435                2440                2445

His Ser Lys Ala Val Arg Lys Gly Val Ser Ser Arg Ser Tyr Val Gly
        2450                2455                2460

Cys Ile Lys Asn Leu Glu Ile Ser Arg Ser Thr Phe Asp Leu Leu Arg
2465                2470                2475                2480

Asn Ser Tyr Gly Val Arg Lys Gly Cys Ala Leu Glu Pro Ile Gln Ser
        2485                2490                2495

Val Ser Phe Leu Arg Gly Gly Tyr Val Glu Met Pro Pro Lys Ser Leu
        2500                2505                2510

Ser Pro Glu Ser Ser Leu Leu Ala Thr Phe Ala Thr Lys Asn Ser Ser
        2515                2520                2525

Gly Ile Leu Leu Val Ala Leu Gly Lys Asp Ala Glu Glu Ala Gly Gly

-continued

```
            2530                2535                2540
Ala Gln Ala His Val Pro Phe Phe Ser Ile Met Leu Leu Glu Gly Arg
2545                2550                2555                2560

Ile Glu Val His Val Asn Ser Gly Asp Gly Thr Ser Leu Arg Lys Ala
                2565                2570                2575

Leu Leu His Ala Pro Thr Gly Ser Tyr Ser Asp Gly Gln Glu His Ser
                2580                2585                2590

Ile Ser Leu Val Arg Asn Arg Val Ile Thr Ile Gln Val Asp Glu
            2595                2600                2605

Asn Ser Pro Val Glu Met Lys Leu Gly Pro Leu Thr Glu Gly Lys Thr
2610                2615                2620

Ile Asp Ile Ser Asn Leu Tyr Ile Gly Gly Leu Pro Glu Asp Lys Ala
2625                2630                2635                2640

Thr Pro Met Leu Lys Met Arg Thr Ser Phe His Gly Cys Ile Lys Asn
                2645                2650                2655

Val Val Leu Asp Ala Gln Leu Leu Asp Phe Thr His Ala Thr Gly Ser
                2660                2665                2670

Glu Gln Val Glu Leu Asp Thr Cys Leu Leu Ala Glu Glu Pro Met Gln
            2675                2680                2685

Ser Leu His Arg Glu His Gly Glu Leu Pro Pro Glu Pro Thr Leu
            2690                2695                2700

Pro Gln Pro Glu Leu Cys Ala Val Asp Thr Ala Pro Gly Tyr Val Ala
2705                2710                2715                2720

Gly Ala His Gln Phe Gly Leu Ser Gln Asn Ser His Leu Val Leu Pro
                2725                2730                2735

Leu Asn Gln Ser Asp Val Arg Lys Arg Leu Gln Val Gln Leu Ser Ile
                2740                2745                2750

Arg Thr Phe Ala Ser Ser Gly Leu Ile Tyr Tyr Val Ala His Gln Asn
            2755                2760                2765

Gln Met Asp Tyr Ala Thr Leu Gln Leu Gln Glu Gly Arg Leu His Phe
        2770                2775                2780

Met Phe Asp Leu Gly Lys Gly Arg Thr Lys Val Ser His Pro Ala Leu
2785                2790                2795                2800

Leu Ser Asp Gly Lys Trp His Thr Val Lys Thr Glu Tyr Ile Lys Arg
                2805                2810                2815

Lys Ala Phe Met Thr Val Asp Gly Gln Glu Ser Pro Ser Val Thr Val
                2820                2825                2830

Val Gly Asn Ala Thr Thr Leu Asp Val Glu Arg Lys Leu Tyr Leu Gly
            2835                2840                2845

Gly Leu Pro Ser His Tyr Arg Ala Arg Asn Ile Gly Thr Ile Thr His
            2850                2855                2860

Ser Ile Pro Ala Cys Ile Gly Glu Ile Met Val Asn Gly Gln Gln Leu
2865                2870                2875                2880

Asp Lys Asp Arg Pro Leu Ser Ala Ser Ala Val Asp Arg Cys Tyr Val
                2885                2890                2895

Val Ala Gln Glu Gly Thr Phe Phe Glu Gly Ser Gly Tyr Ala Ala Leu
            2900                2905                2910

Val Lys Glu Gly Tyr Lys Val Arg Leu Asp Leu Asn Ile Thr Leu Glu
        2915                2920                2925

Phe Arg Thr Thr Ser Lys Asn Gly Val Leu Leu Gly Ile Ser Ser Ala
    2930                2935                2940

Lys Val Asp Ala Ile Gly Leu Glu Ile Val Asp Gly Lys Val Leu Phe
2945                2950                2955                2960
```

His Val Asn Asn Gly Ala Gly Arg Ile Thr Ala Thr Tyr Gln Pro Arg
            2965                2970                2975

Ala Ala Arg Ala Leu Cys Asp Gly Lys Trp His Thr Leu Gln Ala His
        2980                2985                2990

Lys Ser Lys His Arg Ile Val Leu Thr Val Asp Gly Asn Ser Val Arg
        2995                3000                3005

Ala Glu Ser Pro His Thr His Ser Thr Ser Ala Asp Thr Asn Asp Pro
        3010                3015                3020

Ile Tyr Val Gly Gly Tyr Pro Ala His Ile Lys Gln Asn Cys Leu Ser
3025                3030                3035                3040

Ser Arg Ala Ser Phe Arg Gly Cys Val Arg Asn Leu Arg Leu Ser Arg
            3045                3050                3055

Gly Ser Gln Val Gln Ser Leu Asp Leu Ser Arg Ala Phe Asp Leu Gln
            3060                3065                3070

Gly Val Phe Pro His Ser Cys Pro Gly Pro Glu Pro
        3075                3080

<210> SEQ ID NO 5
<211> LENGTH: 3075
<212> TYPE: PRT
<213> ORGANISM: Homo Sapiens
<300> PUBLICATION INFORMATION:
<308> DATABASE ACCESSION NUMBER: Swissprot P25391
<309> DATABASE ENTRY DATE: 1992-05-01

<400> SEQUENCE: 5

Met Arg Gly Gly Val Leu Leu Val Leu Leu Leu Cys Val Ala Ala Gln
1               5                   10                  15

Cys Arg Gln Arg Gly Leu Phe Pro Ala Ile Leu Asn Leu Ala Ser Asn
            20                  25                  30

Ala His Ile Ser Thr Asn Ala Thr Cys Gly Glu Lys Gly Pro Glu Met
        35                  40                  45

Phe Cys Lys Leu Val Glu His Val Pro Gly Arg Pro Val Arg Asn Pro
50                  55                  60

Gln Cys Arg Ile Cys Asp Gly Asn Ser Ala Asn Pro Arg Glu Arg His
65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Ile Thr Leu Asp
            100                 105                 110

Leu Arg Gln Val Phe Gln Val Ala Tyr Val Ile Ile Lys Ala Ala Asn
        115                 120                 125

Ala Pro Arg Pro Gly Asn Trp Ile Leu Glu Arg Ser Leu Asp Gly Thr
    130                 135                 140

Thr Phe Ser Pro Trp Gln Tyr Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
                165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
        195                 200                 205

Asp Asp Leu Ser Pro Lys Leu Leu Glu Phe Thr Ser Ala Arg Tyr Ile
    210                 215                 220

Arg Leu Arg Leu Gln Arg Ile Arg Thr Leu Asn Ala Asp Leu Met Thr

-continued

```
             225                 230                 235                 240
Leu Ser His Arg Glu Pro Lys Glu Leu Asp Pro Ile Val Thr Arg Arg
                 245                 250                 255
Tyr Tyr Tyr Ser Ile Lys Asp Ile Ser Val Gly Gly Met Cys Ile Cys
             260                 265                 270
Tyr Gly His Ala Ser Ser Cys Pro Trp Asp Glu Thr Thr Lys Lys Leu
             275                 280                 285
Gln Cys Gln Cys Glu His Asn Thr Cys Gly Glu Ser Cys Asn Arg Cys
             290                 295                 300
Cys Pro Gly Tyr His Gln Pro Trp Arg Pro Gly Thr Val Ser Ser
305              310                 315                 320
Gly Asn Thr Cys Glu Ala Cys Asn Cys His Asn Lys Ala Lys Asp Cys
                 325                 330                 335
Tyr Tyr Asp Glu Ser Val Ala Lys Gln Lys Lys Ser Leu Asn Thr Ala
                 340                 345                 350
Gly Gln Phe Arg Gly Gly Gly Val Cys Ile Asn Cys Leu Gln Asn Thr
             355                 360                 365
Met Gly Ile Asn Cys Glu Thr Cys Ile Asp Gly Tyr Tyr Arg Pro His
         370                 375                 380
Lys Val Ser Pro Tyr Glu Asp Glu Pro Cys Arg Pro Cys Asn Cys Asp
385              390                 395                 400
Pro Val Gly Ser Leu Ser Val Cys Ile Lys Asp Asp Leu His Ser
             405                 410                 415
Asp Leu His Asn Gly Lys Gln Pro Gly Gln Cys Pro Cys Lys Glu Gly
             420                 425                 430
Tyr Thr Gly Glu Lys Cys Asp Arg Cys Gln Leu Gly Tyr Lys Asp Tyr
             435                 440                 445
Pro Thr Cys Val Ser Cys Gly Cys Asn Pro Val Gly Ser Ala Ser Asp
         450                 455                 460
Glu Pro Cys Thr Gly Pro Cys Val Cys Lys Glu Asn Val Glu Gly Lys
465              470                 475                 480
Ala Cys Asp Arg Cys Lys Pro Gly Phe Tyr Asn Leu Lys Glu Lys Asn
                 485                 490                 495
Pro Arg Gly Cys Ser Glu Cys Phe Cys Phe Gly Val Ser Asp Val Cys
             500                 505                 510
Ser Ser Leu Ser Trp Pro Val Gly Gln Val Asn Ser Met Ser Gly Trp
             515                 520                 525
Leu Val Thr Asp Leu Ile Ser Pro Arg Lys Ile Pro Ser Gln Gln Asp
         530                 535                 540
Ala Leu Gly Gly Arg His Gln Val Ser Ile Asn Asn Thr Ala Val Met
545              550                 555                 560
Gln Arg Leu Ala Pro Lys Tyr Tyr Trp Ala Ala Pro Glu Ala Tyr Leu
                 565                 570                 575
Gly Asn Lys Leu Thr Ala Phe Gly Gly Phe Leu Lys Tyr Thr Val Ser
             580                 585                 590
Tyr Asp Ile Pro Val Glu Thr Val Asp Ser Asn Leu Met Ser His Ala
             595                 600                 605
Asp Val Ile Ile Lys Gly Asn Gly Leu Thr Leu Ser Thr Gln Ala Glu
         610                 615                 620
Gly Leu Ser Leu Gln Pro Tyr Glu Glu Tyr Leu Asn Val Val Arg Leu
625              630                 635                 640
Val Pro Glu Asn Phe Gln Asp Phe His Ser Lys Arg Gln Ile Asp Arg
                 645                 650                 655
```

-continued

```
Asp Gln Leu Met Thr Val Leu Ala Asn Val Thr His Leu Leu Ile Arg
            660                 665                 670
Ala Thr Tyr Asn Ser Ala Lys Met Ala Leu Tyr Arg Leu Glu Ser Val
        675                 680                 685
Ser Leu Asp Ile Ala Ser Ser Asn Ala Ile Asp Leu Val Val Ala Ala
    690                 695                 700
Asp Val Glu His Cys Glu Cys Pro Gln Gly Tyr Thr Gly Thr Ser Cys
705                 710                 715                 720
Glu Ser Cys Leu Ser Gly Tyr Tyr Arg Val Asp Gly Ile Leu Phe Gly
                725                 730                 735
Gly Ile Cys Gln Pro Cys Glu Cys His Gly His Ala Ala Glu Cys Asn
            740                 745                 750
Val His Gly Val Cys Ile Ala Cys Ala His Asn Thr Thr Gly Val His
        755                 760                 765
Cys Glu Gln Cys Leu Pro Gly Phe Tyr Gly Glu Pro Ser Arg Gly Thr
    770                 775                 780
Pro Gly Asp Cys Gln Pro Cys Ala Cys Pro Leu Thr Ile Ala Ser Asn
785                 790                 795                 800
Asn Phe Ser Pro Thr Cys His Leu Asn Asp Gly Asp Glu Val Val Cys
                805                 810                 815
Asp Trp Cys Ala Pro Gly Tyr Ser Gly Ala Trp Cys Glu Arg Cys Ala
            820                 825                 830
Asp Gly Tyr Tyr Gly Asn Pro Thr Val Pro Gly Glu Ser Cys Val Pro
        835                 840                 845
Cys Asp Cys Ser Gly Asn Val Asp Pro Ser Glu Ala Gly His Cys Asp
    850                 855                 860
Ser Val Thr Gly Glu Cys Leu Lys Cys Leu Gly Asn Thr Asp Gly Ala
865                 870                 875                 880
His Cys Glu Arg Cys Ala Asp Gly Phe Tyr Gly Asp Ala Val Thr Ala
                885                 890                 895
Lys Asn Cys Arg Ala Cys Glu Cys His Val Lys Gly Ser His Ser Ala
            900                 905                 910
Val Cys His Leu Glu Thr Gly Leu Cys Asp Cys Lys Pro Asn Val Thr
        915                 920                 925
Gly Gln Gln Cys Asp Gln Cys Leu His Gly Tyr Tyr Gly Leu Asp Ser
    930                 935                 940
Gly His Gly Cys Arg Pro Cys Asn Cys Ser Val Ala Gly Ser Val Ser
945                 950                 955                 960
Asp Gly Cys Thr Asp Glu Gly Gln Cys His Cys Val Pro Gly Val Ala
                965                 970                 975
Gly Lys Arg Cys Asp Arg Cys Ala His Gly Phe Tyr Ala Tyr Gln Asp
            980                 985                 990
Gly Ser Cys Thr Pro Cys Asp Cys Pro His Thr Gln Asn Thr Cys Asp
        995                 1000                1005
Pro Glu Thr Gly Glu Cys Val Cys Pro Pro His Thr Gln Gly Gly Lys
    1010                1015                1020
Cys Glu Glu Cys Glu Asp Gly His Trp Gly Tyr Asp Ala Glu Val Gly
1025                1030                1035                1040
Cys Gln Ala Cys Asn Cys Ser Leu Val Gly Ser Thr His His Arg Cys
                1045                1050                1055
Asp Val Val Thr Gly His Cys Gln Cys Lys Ser Lys Phe Gly Gly Arg
            1060                1065                1070
```

```
Ala Cys Asp Gln Cys Ser Leu Gly Tyr Arg Asp Phe Pro Asp Cys Val
        1075                1080                1085

Pro Cys Asp Cys Asp Leu Arg Gly Thr Ser Gly Ala Cys Asn Leu
        1090                1095                1100

Glu Gln Gly Leu Cys Gly Cys Val Glu Thr Gly Ala Cys Pro Cys
1105                1110                1115                1120

Lys Glu Asn Val Phe Gly Pro Gln Cys Asn Glu Cys Arg Gly Thr
            1125                1130                1135

Phe Ala Leu Arg Ala Asp Asn Pro Leu Gly Cys Ser Pro Cys Phe Cys
            1140                1145                1150

Ser Gly Leu Ser His Leu Cys Ser Glu Leu Glu Asp Tyr Val Arg Thr
            1155                1160                1165

Pro Val Thr Leu Gly Ser Asp Gln Pro Leu Leu Arg Val Val Ser Gln
        1170                1175                1180

Ser Asn Leu Arg Gly Thr Thr Glu Gly Val Tyr Tyr Gln Ala Pro Asp
1185                1190                1195                1200

Phe Leu Leu Asp Ala Ala Thr Val Arg Gln His Ile Arg Ala Glu Pro
            1205                1210                1215

Phe Tyr Trp Arg Leu Pro Gln Gln Phe Gln Gly Asp Gln Leu Met Ala
        1220                1225                1230

Tyr Gly Gly Lys Leu Lys Tyr Ser Val Ala Phe Tyr Ser Leu Asp Gly
        1235                1240                1245

Val Gly Thr Ser Asn Phe Glu Pro Gln Val Leu Ile Lys Gly Gly Arg
        1250                1255                1260

Ile Arg Lys Gln Val Ile Tyr Met Asp Ala Pro Ala Pro Glu Asn Gly
1265                1270                1275                1280

Val Arg Gln Glu Gln Glu Val Ala Met Arg Glu Asn Phe Trp Lys Tyr
            1285                1290                1295

Phe Asn Ser Val Ser Glu Lys Pro Val Thr Arg Glu Asp Phe Met Ser
        1300                1305                1310

Val Leu Ser Asp Ile Glu Tyr Ile Leu Ile Lys Ala Ser Tyr Gly Gln
        1315                1320                1325

Gly Leu Gln Gln Ser Arg Ile Ser Asp Ile Ser Val Glu Val Gly Arg
        1330                1335                1340

Lys Ala Glu Lys Leu His Pro Glu Glu Val Ala Ser Leu Leu Glu
1345                1350                1355                1360

Asn Cys Val Cys Pro Pro Gly Thr Val Gly Phe Ser Cys Gln Asp Cys
            1365                1370                1375

Ala Pro Gly Tyr His Arg Gly Lys Leu Pro Ala Gly Ser Asp Arg Gly
            1380                1385                1390

Pro Arg Pro Leu Val Ala Pro Cys Val Pro Cys Ser Cys Asn Asn His
        1395                1400                1405

Ser Asp Thr Cys Asp Pro Asn Thr Gly Lys Cys Leu Asn Cys Gly Asp
        1410                1415                1420

Asn Thr Ala Gly Asp His Cys Asp Val Cys Thr Ser Gly Tyr Tyr Gly
1425                1430                1435                1440

Lys Val Thr Gly Ser Ala Ser Asp Cys Ala Leu Cys Ala Cys Pro His
            1445                1450                1455

Ser Pro Pro Ala Ser Phe Ser Pro Thr Cys Val Leu Glu Gly Asp His
        1460                1465                1470

Asp Phe Arg Cys Asp Ala Cys Leu Leu Gly Tyr Glu Gly Lys His Cys
        1475                1480                1485

Glu Arg Cys Ser Ser Ser Tyr Tyr Gly Asn Pro Gln Thr Pro Gly Gly
```

```
                1490                1495                1500
Ser Cys Gln Lys Cys Asp Cys Asn Arg His Gly Ser Val His Gly Asp
1505                1510                1515                1520

Cys Asp Arg Thr Ser Gly Gln Cys Val Cys Arg Leu Gly Ala Ser Gly
                1525                1530                1535

Leu Arg Cys Asp Glu Cys Glu Pro Arg His Ile Leu Met Glu Thr Asp
                1540                1545                1550

Cys Val Ser Cys Asp Asp Glu Cys Val Gly Val Leu Leu Asn Asp Leu
                1555                1560                1565

Asp Glu Ile Gly Asp Ala Val Leu Ser Leu Asn Leu Thr Gly Ile Ile
                1570                1575                1580

Pro Val Pro Tyr Gly Ile Leu Ser Asn Leu Glu Asn Thr Thr Lys Tyr
1585                1590                1595                1600

Leu Gln Glu Ser Leu Leu Lys Glu Asn Met Gln Lys Asp Leu Gly Lys
                1605                1610                1615

Ile Lys Leu Glu Gly Val Ala Glu Glu Thr Asp Asn Leu Gln Lys Lys
                1620                1625                1630

Leu Thr Arg Met Leu Ala Ser Thr Gln Lys Val Asn Arg Ala Thr Glu
                1635                1640                1645

Arg Ile Phe Lys Glu Ser Gln Asp Leu Ala Val Ala Ile Glu Arg Leu
                1650                1655                1660

Gln Met Ser Ile Thr Glu Ile Met Glu Lys Thr Thr Leu Asn Gln Thr
1665                1670                1675                1680

Leu Asp Glu Asp Phe Leu Leu Pro Asn Ser Thr Leu Gln Asn Met Gln
                1685                1690                1695

Gln Asn Gly Thr Ser Leu Leu Glu Ile Met Gln Ile Arg Asp Phe Thr
                1700                1705                1710

Gln Leu His Gln Asn Ala Thr Leu Glu Leu Lys Ala Ala Glu Asp Leu
                1715                1720                1725

Leu Ser Gln Ile Gln Glu Asn Tyr Gln Lys Pro Leu Glu Glu Leu Glu
                1730                1735                1740

Val Leu Lys Glu Ala Ala Ser His Val Leu Ser Lys His Asn Asn Glu
1745                1750                1755                1760

Leu Lys Ala Ala Glu Ala Leu Val Arg Glu Ala Glu Ala Lys Met Gln
                1765                1770                1775

Glu Ser Asn His Leu Leu Leu Met Val Asn Ala Asn Leu Arg Glu Phe
                1780                1785                1790

Ser Asp Lys Lys Leu His Val Gln Glu Gln Asn Leu Thr Ser Glu
                1795                1800                1805

Leu Ile Val Gln Gly Arg Gly Leu Ile Asp Ala Ala Ala Gln Thr
                1810                1815                1820

Asp Ala Val Gln Asp Ala Leu Glu His Leu Glu Asp His Gln Asp Lys
1825                1830                1835                1840

Leu Leu Leu Trp Ser Ala Lys Ile Arg His Ile Asp Asp Leu Val
                1845                1850                1855

Met His Met Ser Gln Arg Asn Ala Val Asp Leu Val Tyr Arg Ala Glu
                1860                1865                1870

Asp His Ala Thr Glu Phe Gln Arg Leu Ala Asp Val Leu Tyr Ser Gly
                1875                1880                1885

Leu Glu Asn Ile Arg Asn Val Ser Leu Asn Ala Thr Ser Ala Ala Tyr
                1890                1895                1900

Val His Tyr Asn Ile Gln Ser Leu Ile Glu Glu Ser Glu Glu Leu Ala
1905                1910                1915                1920
```

-continued

Arg Asp Ala His Arg Thr Val Thr Glu Thr Ser Leu Leu Ser Glu Ser
            1925                1930                1935
Leu Val Ser Asn Gly Lys Ala Ala Val Gln Arg Ser Ser Arg Phe Leu
        1940                1945                1950
Lys Glu Gly Asn Asn Leu Ser Arg Lys Leu Pro Gly Ile Ala Leu Glu
        1955                1960                1965
Leu Ser Glu Leu Arg Asn Lys Thr Asn Arg Phe Gln Glu Asn Ala Val
    1970                1975                1980
Glu Ile Thr Arg Gln Thr Asn Glu Ser Leu Leu Ile Leu Arg Ala Ile
1985                1990                1995                2000
Pro Glu Gly Ile Arg Asp Lys Gly Ala Lys Thr Lys Glu Leu Ala Thr
                2005                2010                2015
Ser Ala Ser Gln Ser Ala Val Ser Thr Leu Arg Asp Val Ala Gly Leu
            2020                2025                2030
Ser Gln Glu Leu Leu Asn Thr Ser Ala Ser Leu Ser Arg Val Asn Thr
        2035                2040                2045
Thr Leu Arg Glu Thr His Gln Leu Leu Gln Asp Ser Thr Met Ala Thr
    2050                2055                2060
Leu Leu Ala Gly Arg Lys Val Lys Asp Val Glu Ile Gln Ala Asn Leu
2065                2070                2075                2080
Leu Phe Asp Arg Leu Lys Pro Leu Lys Met Leu Glu Glu Asn Leu Ser
                2085                2090                2095
Arg Asn Leu Ser Glu Ile Lys Leu Leu Ile Ser Gln Ala Arg Lys Gln
            2100                2105                2110
Ala Ala Ser Ile Lys Val Ala Val Ser Ala Asp Arg Asp Cys Ile Arg
        2115                2120                2125
Ala Tyr Gln Pro Gln Ile Ser Ser Thr Asn Tyr Asn Thr Leu Thr Leu
    2130                2135                2140
Asn Val Lys Thr Gln Glu Pro Asp Asn Leu Leu Phe Tyr Leu Gly Ser
2145                2150                2155                2160
Ser Thr Ala Ser Asp Phe Leu Ala Val Glu Met Arg Arg Gly Arg Val
                2165                2170                2175
Ala Phe Leu Trp Asp Leu Gly Ser Gly Ser Thr Arg Leu Glu Phe Pro
            2180                2185                2190
Asp Phe Pro Ile Asp Asp Asn Arg Trp His Ser Ile His Val Ala Arg
        2195                2200                2205
Phe Gly Asn Ile Gly Ser Leu Ser Val Lys Glu Met Ser Ser Asn Gln
    2210                2215                2220
Lys Ser Pro Thr Lys Thr Ser Lys Ser Pro Gly Thr Ala Asn Val Leu
2225                2230                2235                2240
Asp Val Asn Asn Ser Thr Leu Met Phe Val Gly Gly Leu Gly Gly Gln
                2245                2250                2255
Ile Lys Lys Ser Pro Ala Val Lys Val Thr His Phe Lys Gly Cys Leu
            2260                2265                2270
Gly Glu Ala Phe Leu Asn Gly Lys Ser Ile Gly Leu Trp Asn Tyr Ile
        2275                2280                2285
Glu Arg Glu Gly Lys Cys Arg Gly Cys Phe Gly Ser Ser Gln Asn Glu
    2290                2295                2300
Asp Pro Ser Phe His Phe Asp Gly Ser Gly Tyr Ser Val Val Glu Lys
2305                2310                2315                2320
Ser Leu Pro Ala Thr Val Thr Gln Ile Ile Met Leu Phe Asn Thr Phe
                2325                2330                2335

```
Ser Pro Asn Gly Leu Leu Tyr Leu Gly Ser Tyr Gly Thr Lys Asp
            2340                2345                2350

Phe Leu Ser Ile Glu Leu Phe Arg Gly Arg Val Lys Val Met Thr Asp
        2355                2360                2365

Leu Gly Ser Gly Pro Ile Thr Leu Thr Asp Arg Arg Tyr Asn Asn
    2370                2375                2380

Gly Thr Trp Tyr Lys Ile Ala Phe Gln Arg Asn Arg Lys Gln Gly Val
2385                2390                2395                2400

Leu Ala Val Ile Asp Ala Tyr Asn Thr Ser Asn Lys Glu Thr Lys Gln
            2405                2410                2415

Gly Glu Thr Pro Gly Ala Ser Asp Leu Asn Arg Leu Asp Lys Asp
        2420                2425                2430

Pro Ile Tyr Val Gly Gly Leu Pro Arg Ser Arg Val Val Arg Arg Gly
    2435                2440                2445

Val Thr Thr Lys Ser Phe Val Gly Cys Ile Lys Asn Leu Glu Ile Ser
    2450                2455                2460

Arg Ser Thr Phe Asp Leu Leu Arg Asn Ser Tyr Gly Val Arg Lys Gly
2465                2470                2475                2480

Cys Leu Leu Glu Pro Ile Arg Ser Val Ser Phe Leu Lys Gly Gly Tyr
            2485                2490                2495

Ile Glu Leu Pro Pro Lys Ser Leu Ser Pro Glu Ser Glu Trp Leu Val
            2500                2505                2510

Thr Phe Ala Thr Thr Asn Ser Ser Gly Ile Ile Leu Ala Ala Leu Gly
            2515                2520                2525

Gly Asp Val Glu Lys Arg Gly Asp Arg Glu Glu Ala His Val Pro Phe
        2530                2535                2540

Phe Ser Val Met Leu Ile Gly Gly Asn Ile Glu Val His Val Asn Pro
2545                2550                2555                2560

Gly Asp Gly Thr Gly Leu Arg Lys Ala Leu Leu His Ala Pro Thr Gly
            2565                2570                2575

Thr Cys Ser Asp Gly Gln Ala His Ser Ile Ser Leu Val Arg Asn Arg
            2580                2585                2590

Arg Ile Ile Thr Val Gln Leu Asp Glu Asn Asn Pro Val Glu Met Lys
        2595                2600                2605

Leu Gly Thr Leu Val Glu Ser Arg Thr Ile Asn Val Ser Asn Leu Tyr
        2610                2615                2620

Val Gly Gly Ile Pro Glu Gly Glu Gly Thr Ser Leu Leu Thr Met Arg
2625                2630                2635                2640

Arg Ser Phe His Gly Cys Ile Lys Asn Leu Ile Phe Asn Leu Glu Leu
            2645                2650                2655

Leu Asp Phe Asn Ser Ala Val Gly His Glu Gln Val Asp Leu Asp Thr
            2660                2665                2670

Cys Trp Leu Ser Glu Arg Pro Lys Leu Ala Pro Asp Ala Glu Asp Ser
            2675                2680                2685

Lys Leu Leu Arg Glu Pro Arg Ala Phe Pro Glu Gln Cys Val Val Asp
        2690                2695                2700

Ala Ala Leu Glu Tyr Val Pro Gly Ala His Gln Phe Gly Leu Thr Gln
2705                2710                2715                2720

Asn Ser His Phe Ile Leu Pro Phe Asn Gln Ser Ala Val Arg Lys Lys
            2725                2730                2735

Leu Ser Val Glu Leu Ser Ile Arg Thr Phe Ala Ser Ser Gly Leu Ile
            2740                2745                2750

Tyr Tyr Met Ala His Gln Asn Gln Ala Asp Tyr Ala Val Leu Gln Leu
```

-continued

```
                    2755                2760                2765
His Gly Gly Arg Leu His Phe Met Phe Asp Leu Gly Lys Gly Arg Thr
    2770                2775                2780
Lys Val Ser His Pro Ala Leu Leu Ser Asp Gly Lys Trp His Thr Val
2785                2790                2795                2800
Lys Thr Asp Tyr Val Lys Arg Lys Gly Phe Ile Thr Val Asp Gly Arg
                2805                2810                2815
Glu Ser Pro Met Val Thr Val Gly Asp Gly Thr Met Leu Asp Val
            2820                2825                2830
Glu Gly Leu Phe Tyr Leu Gly Gly Leu Pro Ser Gln Tyr Gln Ala Arg
        2835                2840                2845
Lys Ile Gly Asn Ile Thr His Ser Ile Pro Ala Cys Ile Gly Asp Val
    2850                2855                2860
Thr Val Asn Ser Lys Gln Leu Asp Lys Asp Ser Pro Val Ser Ala Phe
2865                2870                2875                2880
Thr Val Asn Arg Cys Tyr Ala Val Ala Gln Glu Gly Thr Tyr Phe Asp
                2885                2890                2895
Gly Ser Gly Tyr Ala Ala Leu Val Lys Glu Gly Tyr Lys Val Gln Ser
            2900                2905                2910
Asp Val Asn Ile Thr Leu Glu Phe Arg Thr Ser Ser Gln Asn Gly Val
        2915                2920                2925
Leu Leu Gly Ile Ser Thr Ala Lys Val Asp Ala Ile Gly Leu Glu Leu
    2930                2935                2940
Val Asp Gly Lys Val Leu Phe His Val Asn Asn Gly Ala Gly Arg Ile
2945                2950                2955                2960
Thr Pro Ala Tyr Glu Pro Lys Thr Ala Thr Val Leu Cys Asp Gly Lys
                2965                2970                2975
Trp His Thr Leu Gln Ala Asn Lys Ser Lys His Arg Ile Thr Leu Ile
            2980                2985                2990
Val Asp Gly Asn Ala Val Gly Ala Glu Ser Pro His Thr Gln Ser Thr
        2995                3000                3005
Ser Val Asp Thr Asn Asn Pro Ile Tyr Val Gly Gly Tyr Pro Ala Gly
    3010                3015                3020
Val Lys Gln Lys Cys Leu Arg Ser Gln Thr Ser Phe Arg Gly Cys Leu
3025                3030                3035                3040
Arg Lys Leu Ala Leu Ile Lys Ser Pro Gln Val Gln Ser Phe Asp Phe
                3045                3050                3055
Ser Arg Ala Phe Glu Leu His Gly Val Phe Leu His Ser Cys Pro Gly
            3060                3065                3070
Thr Glu Ser
        3075
```

<210> SEQ ID NO 6
<211> LENGTH: 1786
<212> TYPE: PRT
<213> ORGANISM: Homo Sapiens
<300> PUBLICATION INFORMATION:
<308> DATABASE ACCESSION NUMBER: Swissprot P07942
<309> DATABASE ENTRY DATE: 1988-08-01

<400> SEQUENCE: 6

```
Met Gly Leu Leu Gln Leu Leu Ala Phe Ser Phe Leu Ala Leu Cys Arg
 1               5                  10                  15
Ala Arg Val Arg Ala Gln Glu Pro Glu Phe Ser Tyr Gly Cys Ala Glu
            20                  25                  30
```

-continued

```
Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
 50                  55                  60

Cys Ile Val Ser His Leu Gln Glu Asp Lys Lys Cys Phe Ile Cys Asn
 65                  70                  75                  80

Ser Gln Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
            115                 120                 125

Ala Glu Phe His Phe Thr His Leu Ile Met Thr Phe Lys Thr Phe Arg
130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
            195                 200                 205

Ala Leu Asp Pro Ala Phe Lys Ile Glu Asp Pro Tyr Ser Pro Arg Ile
            210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
            275                 280                 285

Glu Val Glu Gly Met Val His Gly His Cys Met Cys Arg His Asn Thr
290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
            340                 345                 350

Ala Thr Gly Asn Val Ser Gly Gly Val Cys Asp Asp Cys Gln His Asn
            355                 360                 365

Thr Met Gly Arg Asn Cys Glu Gln Cys Lys Pro Phe Tyr Tyr Gln His
370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
            435                 440                 445

Ser Glu Asp Pro Phe Gly Cys Lys Ser Cys Ala Cys Asn Pro Leu Gly
```

-continued

```
            450                 455                 460
Thr Ile Pro Gly Gly Asn Pro Cys Asp Ser Glu Thr Gly His Cys Tyr
465                 470                 475                 480
Cys Lys Arg Leu Val Thr Gly Gln His Cys Asp Gln Cys Leu Pro Glu
                485                 490                 495
His Trp Gly Leu Ser Asn Asp Leu Asp Gly Cys Arg Pro Cys Asp Cys
                500                 505                 510
Asp Leu Gly Gly Ala Leu Asn Asn Ser Cys Phe Ala Glu Ser Gly Gln
            515                 520                 525
Cys Ser Cys Arg Pro His Met Ile Gly Arg Gln Cys Asn Glu Val Glu
530                 535                 540
Pro Gly Tyr Tyr Phe Ala Thr Leu Asp His Tyr Leu Tyr Glu Ala Glu
545                 550                 555                 560
Glu Ala Asn Leu Gly Pro Gly Val Ser Ile Val Glu Arg Gln Tyr Ile
                565                 570                 575
Gln Asp Arg Ile Pro Ser Trp Thr Gly Ala Gly Phe Val Arg Val Pro
                580                 585                 590
Glu Gly Ala Tyr Leu Glu Phe Phe Ile Asp Asn Ile Pro Tyr Ser Met
            595                 600                 605
Glu Tyr Asp Ile Leu Ile Arg Tyr Glu Pro Gln Leu Pro Asp His Trp
            610                 615                 620
Glu Lys Ala Val Ile Thr Val Gln Arg Pro Gly Arg Ile Pro Thr Ser
625                 630                 635                 640
Ser Arg Cys Gly Asn Thr Ile Pro Asp Asp Asn Gln Val Val Ser
                645                 650                 655
Leu Ser Pro Gly Ser Arg Tyr Val Val Leu Pro Arg Pro Val Cys Phe
                660                 665                 670
Glu Lys Gly Thr Asn Tyr Thr Val Arg Leu Glu Leu Pro Gln Tyr Thr
            675                 680                 685
Ser Ser Asp Ser Asp Val Glu Ser Pro Tyr Thr Leu Ile Asp Ser Leu
            690                 695                 700
Val Leu Met Pro Tyr Cys Lys Ser Leu Asp Ile Phe Thr Val Gly Gly
705                 710                 715                 720
Ser Gly Asp Gly Val Val Thr Asn Ser Ala Trp Glu Thr Phe Gln Arg
                725                 730                 735
Tyr Arg Cys Leu Glu Asn Ser Arg Ser Val Val Lys Thr Pro Met Thr
                740                 745                 750
Asp Val Cys Arg Asn Ile Ile Phe Ser Ile Ser Ala Leu Leu His Gln
                755                 760                 765
Thr Gly Leu Ala Cys Glu Cys Asp Pro Gln Gly Ser Leu Ser Ser Val
770                 775                 780
Cys Asp Pro Asn Gly Gly Gln Cys Gln Cys Arg Pro Asn Val Val Gly
785                 790                 795                 800
Arg Thr Cys Asn Arg Cys Ala Pro Gly Thr Phe Gly Phe Gly Pro Ser
                805                 810                 815
Gly Cys Lys Pro Cys Glu Cys His Leu Gln Gly Ser Val Asn Ala Phe
                820                 825                 830
Cys Asn Pro Val Thr Gly Gln Cys His Cys Phe Gln Gly Val Tyr Ala
                835                 840                 845
Arg Gln Cys Asp Arg Cys Leu Pro Gly His Trp Gly Phe Pro Ser Cys
            850                 855                 860
Gln Pro Cys Gln Cys Asn Gly His Ala Asp Asp Cys Asp Pro Val Thr
865                 870                 875                 880
```

-continued

```
Gly Glu Cys Leu Asn Cys Gln Asp Tyr Thr Met Gly His Asn Cys Glu
            885                 890                 895

Arg Cys Leu Ala Gly Tyr Tyr Gly Asp Pro Ile Ile Gly Ser Gly Asp
        900                 905                 910

His Cys Arg Pro Cys Pro Cys Pro Asp Gly Pro Asp Ser Gly Arg Gln
    915                 920                 925

Phe Ala Arg Ser Cys Tyr Gln Asp Pro Val Thr Leu Gln Leu Ala Cys
930                 935                 940

Val Cys Asp Pro Gly Tyr Ile Gly Ser Arg Cys Asp Cys Ala Ser
945                 950                 955                 960

Gly Tyr Phe Gly Asn Pro Ser Glu Val Gly Ser Cys Gln Pro Cys
                965                 970                 975

Gln Cys His Asn Asn Ile Asp Thr Thr Asp Pro Glu Ala Cys Asp Lys
            980                 985                 990

Glu Thr Gly Arg Cys Leu Lys Cys Leu Tyr His Thr Glu Gly Glu His
        995                 1000                1005

Cys Gln Phe Cys Arg Phe Gly Tyr Tyr Gly Asp Ala Leu Arg Gln Asp
    1010                1015                1020

Cys Arg Lys Cys Val Cys Asn Tyr Leu Gly Thr Val Gln Glu His Cys
1025                1030                1035                1040

Asn Gly Ser Asp Cys Gln Cys Asp Lys Ala Thr Gly Gln Cys Leu Cys
            1045                1050                1055

Leu Pro Asn Val Ile Gly Gln Asn Cys Asp Arg Cys Ala Pro Asn Thr
        1060                1065                1070

Trp Gln Leu Ala Ser Gly Thr Gly Cys Asp Pro Cys Asn Cys Asn Ala
    1075                1080                1085

Ala His Ser Phe Gly Pro Ser Cys Asn Glu Phe Thr Gly Gln Cys Gln
    1090                1095                1100

Cys Met Pro Gly Phe Gly Gly Arg Thr Cys Ser Glu Cys Gln Glu Leu
1105                1110                1115                1120

Phe Trp Gly Asp Pro Asp Val Glu Cys Arg Ala Cys Asp Cys Asp Pro
        1125                1130                1135

Arg Gly Ile Glu Thr Pro Gln Cys Asp Gln Ser Thr Gly Gln Cys Val
            1140                1145                1150

Cys Val Glu Gly Val Glu Gly Pro Arg Cys Asp Lys Cys Thr Arg Gly
        1155                1160                1165

Tyr Ser Gly Val Phe Pro Asp Cys Thr Pro Cys His Gln Cys Phe Ala
    1170                1175                1180

Leu Trp Asp Val Ile Ile Ala Glu Leu Thr Asn Arg Thr His Arg Phe
1185                1190                1195                1200

Leu Glu Lys Ala Lys Ala Leu Lys Ile Ser Gly Val Ile Gly Pro Tyr
            1205                1210                1215

Arg Glu Thr Val Asp Ser Val Glu Arg Lys Val Ser Glu Ile Lys Asp
            1220                1225                1230

Ile Leu Ala Gln Ser Pro Ala Ala Glu Pro Leu Lys Asn Ile Gly Asn
        1235                1240                1245

Leu Phe Glu Glu Ala Glu Lys Leu Ile Lys Asp Val Thr Glu Met Met
    1250                1255                1260

Ala Gln Val Glu Val Lys Leu Ser Asp Thr Thr Ser Gln Ser Asn Ser
1265                1270                1275                1280

Thr Ala Lys Glu Leu Asp Ser Leu Gln Thr Glu Ala Glu Ser Leu Asp
        1285                1290                1295
```

-continued

```
Asn Thr Val Lys Glu Leu Ala Glu Gln Leu Glu Phe Ile Lys Asn Ser
            1300                1305                1310
Asp Ile Arg Gly Ala Leu Asp Ser Ile Thr Lys Tyr Phe Gln Met Ser
        1315                1320                1325
Leu Glu Ala Glu Arg Val Asn Ala Ser Thr Thr Glu Pro Asn Ser
        1330                1335                1340
Thr Val Glu Gln Ser Ala Leu Met Arg Asp Arg Val Glu Asp Val Met
1345                1350                1355                1360
Met Glu Arg Glu Ser Gln Phe Lys Glu Lys Gln Glu Gln Ala Arg
            1365                1370                1375
Leu Leu Asp Glu Leu Ala Gly Lys Leu Gln Ser Leu Asp Leu Ser Ala
            1380                1385                1390
Ala Ala Glu Met Thr Cys Gly Thr Pro Pro Gly Ala Ser Cys Ser Glu
            1395                1400                1405
Thr Glu Cys Gly Gly Pro Asn Cys Arg Thr Asp Glu Gly Glu Arg Lys
        1410                1415                1420
Cys Gly Gly Pro Gly Cys Gly Gly Leu Val Thr Val Ala His Asn Ala
1425                1430                1435                1440
Trp Gln Lys Ala Met Asp Leu Asp Gln Asp Val Leu Ser Ala Leu Ala
            1445                1450                1455
Glu Val Glu Gln Leu Ser Lys Met Val Ser Glu Ala Lys Leu Arg Ala
            1460                1465                1470
Asp Glu Ala Lys Gln Ser Ala Glu Asp Ile Leu Leu Lys Thr Asn Ala
        1475                1480                1485
Thr Lys Glu Lys Met Asp Lys Ser Asn Glu Glu Leu Arg Asn Leu Ile
        1490                1495                1500
Lys Gln Ile Arg Asn Phe Leu Thr Gln Asp Ser Ala Asp Leu Asp Ser
1505                1510                1515                1520
Ile Glu Ala Val Ala Asn Glu Val Leu Lys Met Glu Met Pro Ser Thr
            1525                1530                1535
Pro Gln Gln Leu Gln Asn Leu Thr Glu Asp Ile Arg Glu Arg Val Glu
            1540                1545                1550
Ser Leu Ser Gln Val Glu Val Ile Leu Gln His Ser Ala Ala Asp Ile
        1555                1560                1565
Ala Arg Ala Glu Met Leu Leu Glu Glu Ala Lys Arg Ala Ser Lys Ser
        1570                1575                1580
Ala Thr Asp Val Lys Val Thr Ala Asp Met Val Lys Glu Ala Leu Glu
1585                1590                1595                1600
Glu Ala Glu Lys Ala Gln Val Ala Ala Glu Lys Ala Ile Lys Gln Ala
            1605                1610                1615
Asp Glu Asp Ile Gln Gly Thr Gln Asn Leu Leu Thr Ser Ile Glu Ser
            1620                1625                1630
Glu Thr Ala Ala Ser Glu Glu Thr Leu Phe Asn Ala Ser Gln Arg Ile
            1635                1640                1645
Ser Glu Leu Glu Arg Asn Val Glu Glu Leu Lys Arg Lys Ala Ala Gln
        1650                1655                1660
Asn Ser Gly Glu Ala Glu Tyr Ile Glu Lys Val Val Tyr Thr Val Lys
1665                1670                1675                1680
Gln Ser Ala Glu Asp Val Lys Lys Thr Leu Asp Gly Glu Leu Asp Glu
            1685                1690                1695
Lys Tyr Lys Lys Val Glu Asn Leu Ile Ala Lys Lys Thr Glu Glu Ser
            1700                1705                1710
Ala Asp Ala Arg Arg Lys Ala Glu Met Leu Gln Asn Glu Ala Lys Thr
```

-continued

```
                1715                1720                1725
Leu Leu Ala Gln Ala Asn Ser Lys Leu Gln Leu Leu Lys Asp Leu Glu
        1730                1735                1740

Arg Lys Tyr Glu Asp Asn Gln Arg Tyr Leu Glu Asp Lys Ala Gln Glu
1745                1750                1755                1760

Leu Ala Arg Leu Glu Gly Glu Val Arg Ser Leu Leu Lys Asp Ile Ser
                1765                1770                1775

Gln Lys Val Ala Val Tyr Ser Thr Cys Leu
        1780                1785
```

<210> SEQ ID NO 7
<211> LENGTH: 1786
<212> TYPE: PRT
<213> ORGANISM: Mus Musculus
<300> PUBLICATION INFORMATION:
<308> DATABASE ACCESSION NUMBER: Swissprot P02469
<309> DATABASE ENTRY DATE: 1989-07-01

<400> SEQUENCE: 7

```
Met Gly Leu Leu Gln Val Phe Ala Phe Gly Val Leu Ala Leu Trp Gly
1               5                   10                  15

Thr Arg Val Cys Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
50                  55                  60

Cys Ile Val Ser His Leu Gln Glu Asp Lys Lys Cys Phe Ile Cys Asp
65                  70                  75                  80

Ser Arg Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ser Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Val Asn Glu
        275                 280                 285
```

```
Glu Val Glu Gly Met Val His Gly His Cys Met Cys Arg His Asn Thr
    290                 295                 300
Lys Gly Leu Asn Cys Glu Leu Cys Met Asp Phe Tyr His Asp Leu Pro
305                 310                 315                 320
Trp Arg Pro Ala Glu Gly Arg Asn Ser Asn Ala Cys Lys Lys Cys Asn
                325                 330                 335
Cys Asn Glu His Ser Ser Ser Cys His Phe Asp Met Ala Val Phe Leu
            340                 345                 350
Ala Thr Gly Asn Val Ser Gly Gly Val Cys Asp Asn Cys Gln His Asn
        355                 360                 365
Thr Met Gly Arg Asn Cys Glu Gln Cys Lys Pro Phe Tyr Phe Gln His
    370                 375                 380
Pro Glu Arg Asp Ile Arg Asp Pro Asn Leu Cys Glu Pro Cys Thr Cys
385                 390                 395                 400
Asp Pro Ala Gly Ser Glu Asn Gly Gly Ile Cys Asp Gly Tyr Thr Asp
                405                 410                 415
Phe Ser Val Gly Leu Ile Ala Gly Gln Cys Arg Cys Lys Leu His Val
            420                 425                 430
Glu Gly Glu Arg Cys Asp Val Cys Lys Glu Gly Phe Tyr Asp Leu Ser
        435                 440                 445
Ala Glu Asp Pro Tyr Gly Cys Lys Ser Cys Ala Cys Asn Pro Leu Gly
    450                 455                 460
Thr Ile Pro Gly Gly Asn Pro Cys Asp Ser Glu Thr Gly Tyr Cys Tyr
465                 470                 475                 480
Cys Lys Arg Leu Val Thr Gly Gln Arg Cys Asp Gln Cys Leu Pro Gln
                485                 490                 495
His Trp Gly Leu Ser Asn Asp Leu Asp Gly Cys Arg Pro Cys Asp Cys
            500                 505                 510
Asp Leu Gly Gly Ala Leu Asn Asn Ser Cys Ser Glu Asp Ser Gly Gln
        515                 520                 525
Cys Ser Cys Leu Pro His Met Ile Gly Arg Gln Cys Asn Glu Val Glu
    530                 535                 540
Ser Gly Tyr Tyr Phe Thr Thr Leu Asp His Tyr Ile Tyr Glu Ala Glu
545                 550                 555                 560
Glu Ala Asn Leu Gly Pro Gly Val Val Val Glu Arg Gln Tyr Ile
                565                 570                 575
Gln Asp Arg Ile Pro Ser Trp Thr Gly Pro Gly Phe Val Arg Val Pro
            580                 585                 590
Glu Gly Ala Tyr Leu Glu Phe Phe Ile Asp Asn Ile Pro Tyr Ser Met
        595                 600                 605
Glu Tyr Glu Ile Leu Ile Arg Tyr Glu Pro Gln Leu Pro Asp His Trp
    610                 615                 620
Glu Lys Ala Val Ile Thr Val Gln Arg Pro Gly Lys Ile Pro Ala Ser
625                 630                 635                 640
Ser Arg Cys Gly Asn Thr Val Pro Asp Asp Asn Gln Val Val Ser
                645                 650                 655
Leu Ser Pro Gly Ser Arg Tyr Val Val Leu Pro Arg Pro Val Cys Phe
            660                 665                 670
Glu Lys Gly Met Asn Tyr Thr Val Arg Leu Glu Leu Pro Gln Tyr Thr
        675                 680                 685
Ala Ser Gly Ser Asp Val Glu Ser Pro Tyr Thr Phe Ile Asp Ser Leu
    690                 695                 700
Val Leu Met Pro Tyr Cys Lys Ser Leu Asp Ile Phe Thr Val Gly Gly
```

-continued

```
            705                 710                 715                 720
Ser Gly Asp Gly Glu Val Thr Asn Ser Ala Trp Glu Thr Phe Gln Arg
                725                 730                 735
Tyr Arg Cys Leu Glu Asn Ser Arg Ser Val Val Lys Thr Pro Met Thr
            740                 745                 750
Asp Val Cys Arg Asn Ile Ile Phe Ser Ile Ser Ala Leu Ile His Gln
            755                 760                 765
Thr Gly Leu Ala Cys Glu Cys Asp Pro Gln Gly Ser Leu Ser Ser Val
            770                 775                 780
Cys Asp Pro Asn Gly Gln Cys Gln Cys Arg Pro Asn Val Val Gly
785                 790                 795                 800
Arg Thr Cys Asn Arg Cys Ala Pro Gly Thr Phe Gly Phe Gly Pro Asn
                805                 810                 815
Gly Cys Lys Pro Cys Asp Cys His Leu Gln Gly Ser Ala Ser Ala Phe
                820                 825                 830
Cys Asp Ala Ile Thr Gly Gln Cys His Cys Phe Gln Gly Ile Tyr Ala
                835                 840                 845
Arg Gln Cys Asp Arg Cys Leu Pro Gly Tyr Trp Gly Phe Pro Ser Cys
            850                 855                 860
Gln Pro Cys Gln Cys Asn Gly His Ala Leu Asp Cys Asp Thr Val Thr
865                 870                 875                 880
Gly Glu Cys Leu Ser Cys Gln Asp Tyr Thr Thr Gly His Asn Cys Glu
                885                 890                 895
Arg Cys Leu Ala Gly Tyr Tyr Gly Asp Pro Ile Ile Gly Ser Gly Asp
                900                 905                 910
His Cys Arg Pro Cys Pro Cys Pro Asp Gly Pro Asp Ser Gly Arg Gln
            915                 920                 925
Phe Ala Arg Ser Cys Tyr Gln Asp Pro Val Thr Leu Gln Leu Ala Cys
            930                 935                 940
Val Cys Asp Pro Gly Tyr Ile Gly Ser Arg Cys Asp Asp Cys Ala Ser
945                 950                 955                 960
Gly Phe Phe Gly Asn Pro Ser Asp Phe Gly Gly Ser Cys Gln Pro Cys
                965                 970                 975
Gln Cys His His Asn Ile Asp Thr Thr Asp Pro Glu Ala Cys Asp Lys
                980                 985                 990
Asp Thr Gly Arg Cys Leu Lys Cys Leu Tyr His Thr Glu Gly Asp His
            995                 1000                1005
Cys Gln Leu Cys Gln Tyr Gly Tyr Tyr Gly Asp Ala Leu Arg Gln Asp
            1010                1015                1020
Cys Arg Lys Cys Val Cys Asn Tyr Leu Gly Thr Val Lys Glu His Cys
1025                1030                1035                1040
Asn Gly Ser Asp Cys His Cys Asp Lys Ala Thr Gly Gln Cys Ser Cys
                1045                1050                1055
Leu Pro Asn Val Ile Gly Gln Asn Cys Asp Arg Cys Ala Pro Asn Thr
                1060                1065                1070
Trp Gln Leu Ala Ser Gly Thr Gly Cys Gly Pro Cys Asn Cys Asn Ala
            1075                1080                1085
Ala His Ser Phe Gly Pro Ser Cys Asn Glu Phe Thr Gly Gln Cys Gln
            1090                1095                1100
Cys Met Pro Gly Phe Gly Gly Arg Thr Cys Ser Glu Cys Gln Glu Leu
1105                1110                1115                1120
Phe Trp Gly Asp Pro Asp Val Glu Cys Arg Ala Cys Asp Cys Asp Pro
                1125                1130                1135
```

-continued

Arg Gly Ile Glu Thr Pro Gln Cys Asp Gln Ser Thr Gly Gln Cys Val
                1140                1145                1150

Cys Val Glu Gly Val Glu Gly Pro Arg Cys Asp Lys Cys Thr Arg Gly
            1155                1160                1165

Tyr Ser Gly Val Phe Pro Asp Cys Thr Pro Cys His Gln Cys Phe Ala
            1170                1175                1180

Leu Trp Asp Ala Ile Ile Gly Glu Leu Thr Asn Arg Thr His Lys Phe
1185                1190                1195                1200

Leu Glu Lys Ala Lys Ala Leu Lys Ile Ser Gly Val Ile Gly Pro Tyr
                1205                1210                1215

Arg Glu Thr Val Asp Ser Val Glu Lys Lys Val Asn Glu Ile Lys Asp
                1220                1225                1230

Ile Leu Ala Gln Ser Pro Ala Ala Glu Pro Leu Lys Asn Ile Gly Ile
                1235                1240                1245

Leu Phe Glu Glu Ala Glu Lys Leu Thr Lys Asp Val Thr Glu Lys Met
            1250                1255                1260

Ala Gln Val Glu Val Lys Leu Thr Asp Thr Ala Ser Gln Ser Asn Ser
1265                1270                1275                1280

Thr Ala Gly Glu Leu Gly Ala Leu Gln Ala Glu Ala Glu Ser Leu Asp
                1285                1290                1295

Lys Thr Val Lys Glu Leu Ala Glu Gln Leu Glu Phe Ile Lys Asn Ser
            1300                1305                1310

Asp Ile Gln Gly Ala Leu Asp Ser Ile Thr Lys Tyr Phe Gln Met Ser
            1315                1320                1325

Leu Glu Ala Glu Lys Arg Val Asn Ala Ser Thr Thr Asp Pro Asn Ser
            1330                1335                1340

Thr Val Glu Gln Ser Ala Leu Thr Arg Asp Arg Val Glu Asp Leu Met
1345                1350                1355                1360

Leu Glu Arg Glu Ser Pro Phe Lys Glu Gln Gln Glu Gln Ala Arg
                1365                1370                1375

Leu Leu Asp Glu Leu Ala Gly Lys Leu Gln Ser Leu Asp Leu Ser Ala
            1380                1385                1390

Ala Ala Gln Met Thr Cys Gly Thr Pro Pro Gly Ala Asp Cys Ser Glu
            1395                1400                1405

Ser Glu Cys Gly Gly Pro Asn Cys Arg Thr Asp Glu Gly Glu Lys Lys
            1410                1415                1420

Cys Gly Gly Pro Gly Cys Gly Gly Leu Val Thr Val Ala His Ser Ala
1425                1430                1435                1440

Trp Gln Lys Ala Met Asp Phe Asp Arg Asp Val Leu Ser Ala Leu Ala
                1445                1450                1455

Glu Val Glu Gln Leu Ser Lys Met Val Ser Glu Ala Lys Val Arg Ala
            1460                1465                1470

Asp Glu Ala Lys Gln Asn Ala Gln Asp Val Leu Leu Lys Thr Asn Ala
            1475                1480                1485

Thr Lys Glu Lys Val Asp Lys Ser Asn Glu Asp Leu Arg Asn Leu Ile
            1490                1495                1500

Lys Gln Ile Arg Asn Phe Leu Thr Glu Asp Ser Ala Asp Leu Asp Ser
1505                1510                1515                1520

Ile Glu Ala Val Ala Asn Glu Val Leu Lys Ser Gly Asn Ala Ser Thr
                1525                1530                1535

Pro Gln Gln Leu Gln Asn Leu Thr Glu Asp Ile Arg Glu Arg Val Glu
            1540                1545                1550

```
Thr Leu Ser Gln Val Glu Val Ile Leu Gln Gln Ser Ala Ala Asp Ile
        1555                1560                1565

Ala Arg Ala Glu Leu Leu Glu Glu Ala Lys Arg Ala Ser Lys Ser
    1570                1575                1580

Ala Thr Asp Val Lys Val Thr Ala Asp Met Val Lys Glu Ala Leu Glu
1585                1590                1595                1600

Glu Ala Glu Lys Ala Gln Val Ala Ala Glu Lys Ala Ile Lys Gln Ala
                1605                1610                1615

Asp Glu Asp Ile Gln Gly Thr Gln Asn Leu Leu Thr Ser Ile Glu Ser
                1620                1625                1630

Glu Thr Ala Ala Ser Glu Glu Thr Leu Thr Asn Ala Ser Gln Arg Ile
                1635                1640                1645

Ser Lys Leu Glu Arg Asn Val Glu Glu Leu Lys Arg Lys Ala Ala Gln
    1650                1655                1660

Asn Ser Gly Glu Ala Glu Tyr Ile Glu Lys Val Val Tyr Ser Val Lys
1665                1670                1675                1680

Gln Asn Ala Asp Asp Val Lys Lys Thr Leu Asp Gly Glu Leu Asp Glu
                1685                1690                1695

Lys Tyr Lys Lys Val Glu Ser Leu Ile Ala Gln Lys Thr Glu Glu Ser
                1700                1705                1710

Ala Asp Ala Arg Arg Lys Ala Glu Leu Leu Gln Asn Glu Ala Lys Thr
                1715                1720                1725

Leu Leu Ala Gln Ala Asn Ser Lys Leu Gln Leu Leu Glu Asp Leu Glu
                1730                1735                1740

Arg Lys Tyr Glu Asp Asn Gln Lys Tyr Leu Glu Asp Lys Ala Gln Glu
1745                1750                1755                1760

Leu Val Arg Leu Glu Gly Glu Val Arg Ser Leu Leu Lys Asp Ile Ser
                1765                1770                1775

Glu Lys Val Ala Val Tyr Ser Thr Cys Leu
                1780                1785

<210> SEQ ID NO 8
<211> LENGTH: 1801
<212> TYPE: PRT
<213> ORGANISM: Rattus Norvegicus
<300> PUBLICATION INFORMATION:
<308> DATABASE ACCESSION NUMBER: Swissprot P15800
<309> DATABASE ENTRY DATE: 1990-04-01

<400> SEQUENCE: 8

Met Glu Trp Ala Ser Gly Lys Pro Gly Arg Gly Arg Gln Gly Gln Pro
1               5                   10                  15

Val Pro Trp Glu Leu Arg Leu Gly Leu Leu Ser Val Leu Ala Ala
            20                  25                  30

Thr Leu Ala Gln Val Pro Ser Leu Asp Val Pro Gly Cys Ser Arg Gly
        35                  40                  45

Ser Cys Tyr Pro Ala Thr Gly Asp Leu Leu Val Gly Arg Ala Asp Arg
    50                  55                  60

Leu Thr Ala Ser Ser Thr Cys Gly Leu His Ser Pro Gln Pro Tyr Cys
65                  70                  75                  80

Ile Val Ser His Leu Gln Asp Glu Lys Lys Cys Phe Leu Cys Asp Ser
                85                  90                  95

Arg Arg Pro Phe Ser Ala Arg Asp Asn Pro Asn Ser His Arg Ile Gln
            100                 105                 110

Asn Val Val Thr Ser Phe Ala Pro Gln Arg Arg Thr Ala Trp Trp Gln
        115                 120                 125
```

-continued

```
Ser Glu Asn Gly Val Pro Met Val Thr Ile Gln Leu Asp Leu Glu Ala
    130                 135                 140

Glu Phe His Phe Thr His Leu Ile Met Thr Phe Lys Thr Phe Arg Pro
145                 150                 155                 160

Ala Ala Met Leu Val Glu Arg Ser Ala Asp Phe Gly Arg Thr Trp Arg
                165                 170                 175

Val Tyr Arg Tyr Phe Ser Tyr Asp Cys Gly Ala Asp Phe Pro Gly Ile
            180                 185                 190

Pro Leu Ala Pro Pro Arg Arg Trp Asp Asp Val Val Cys Glu Ser Arg
        195                 200                 205

Tyr Ser Glu Ile Glu Pro Ser Thr Glu Gly Glu Val Ile Tyr Arg Val
    210                 215                 220

Leu Asp Pro Ala Ile Pro Ile Pro Asp Pro Tyr Ser Ser Arg Ile Gln
225                 230                 235                 240

Asn Leu Leu Lys Ile Thr Asn Leu Arg Val Asn Leu Thr Arg Leu His
                245                 250                 255

Thr Leu Gly Asp Asn Leu Leu Asp Pro Arg Arg Glu Ile Arg Glu Lys
            260                 265                 270

Tyr Tyr Tyr Ala Leu Tyr Glu Leu Val Ile Arg Gly Asn Cys Phe Cys
        275                 280                 285

Tyr Gly His Ala Ser Gln Cys Ala Pro Ala Pro Gly Ala Pro Ala His
    290                 295                 300

Ala Glu Gly Met Val His Gly Ala Cys Ile Cys Lys His Asn Thr Arg
305                 310                 315                 320

Gly Leu Asn Cys Glu Gln Cys Gln Asp Phe Tyr Gln Asp Leu Pro Trp
                325                 330                 335

His Pro Ala Glu Asp Gly His Thr His Ala Cys Arg Lys Cys Glu Cys
            340                 345                 350

Asn Gly His Ser His Ser Cys His Phe Asp Met Ala Val Tyr Leu Ala
        355                 360                 365

Ser Gly Asn Val Ser Gly Gly Val Cys Asp Gly Cys Gln His Asn Thr
    370                 375                 380

Ala Gly Arg His Cys Glu Leu Cys Arg Pro Phe Phe Tyr Arg Asp Pro
385                 390                 395                 400

Thr Lys Asp Met Arg Asp Pro Ala Ala Cys Arg Pro Cys Asp Cys Asp
                405                 410                 415

Pro Met Gly Ser Gln Asp Gly Gly Arg Cys Asp Ser His Asp Asp Pro
            420                 425                 430

Val Leu Gly Leu Val Ser Gly Gln Cys Arg Cys Lys Glu His Val Val
        435                 440                 445

Gly Thr Arg Cys Gln Gln Cys Arg Asp Gly Phe Phe Gly Leu Ser Ala
    450                 455                 460

Ser Asn Pro Arg Gly Cys Gln Arg Cys Gln Cys Asn Ser Arg Gly Thr
465                 470                 475                 480

Val Pro Gly Gly Thr Pro Cys Asp Ser Ser Gly Thr Cys Phe Cys
                485                 490                 495

Lys Arg Leu Val Thr Gly Asp Gly Cys Asp Arg Cys Leu Pro Gly His
            500                 505                 510

Trp Gly Leu Ser His Asp Leu Leu Gly Cys Arg Pro Cys Asp Cys Asp
        515                 520                 525

Val Gly Gly Ala Leu Asp Pro Gln Cys Asp Glu Ala Thr Gly Gln Cys
    530                 535                 540
```

```
Pro Cys Arg Pro His Met Ile Gly Arg Arg Cys Glu Gln Val Gln Pro
545                 550                 555                 560

Gly Tyr Phe Arg Pro Phe Leu Asp His Leu Thr Trp Glu Ala Glu Gly
            565                 570                 575

Ala His Gly Gln Val Leu Glu Val Val Glu Arg Leu Val Thr Asn Arg
                580                 585                 590

Glu Thr Pro Ser Trp Thr Gly Val Gly Phe Val Arg Leu Arg Glu Gly
            595                 600                 605

Gln Glu Val Glu Phe Leu Val Thr Ser Leu Pro Arg Ala Met Asp Tyr
        610                 615                 620

Asp Leu Leu Arg Trp Glu Pro Gln Val Pro Glu Gln Trp Ala Glu
625                 630                 635                 640

Leu Glu Leu Val Val Gln Arg Pro Gly Pro Val Ser Ala His Ser Pro
                645                 650                 655

Cys Gly His Val Leu Pro Arg Asp Asp Arg Ile Gln Gly Met Leu His
                660                 665                 670

Pro Asn Thr Arg Val Leu Val Phe Pro Arg Pro Val Cys Leu Glu Pro
        675                 680                 685

Gly Leu Ser Tyr Lys Leu Lys Leu Lys Leu Thr Gly Thr Gly Gly Arg
        690                 695                 700

Ala His Pro Glu Thr Pro Tyr Ser Gly Ser Gly Ile Leu Ile Asp Ser
705                 710                 715                 720

Leu Val Leu Gln Pro His Val Leu Met Leu Glu Met Phe Ser Gly Gly
                725                 730                 735

Asp Ala Ala Ala Leu Glu Arg Arg Thr Thr Phe Glu Arg Tyr Arg Cys
                740                 745                 750

His Glu Glu Gly Leu Met Pro Ser Lys Thr Pro Leu Ser Glu Ala Cys
            755                 760                 765

Val Pro Leu Leu Ile Ser Ala Ser Ser Leu Val Tyr Asn Gly Ala Leu
        770                 775                 780

Pro Cys Gln Cys Asp Pro Gln Gly Ser Leu Ser Ser Glu Cys Asn Pro
785                 790                 795                 800

His Gly Gly Gln Cys Arg Cys Lys Pro Gly Val Val Gly Arg Arg Cys
                805                 810                 815

Asp Ala Cys Ala Thr Gly Tyr Tyr Gly Phe Gly Pro Ala Gly Cys Gln
                820                 825                 830

Ala Cys Gln Cys Ser Pro Asp Gly Ala Leu Ser Ala Leu Cys Glu Gly
            835                 840                 845

Thr Ser Gly Gln Cys Leu Cys Arg Thr Gly Ala Phe Gly Leu Arg Cys
850                 855                 860

Asp His Cys Gln Arg Gly Gln Trp Gly Phe Pro Asn Cys Arg Pro Cys
865                 870                 875                 880

Val Cys Asn Gly Arg Ala Asp Glu Cys Asp Ala His Thr Gly Ala Cys
                885                 890                 895

Leu Gly Cys Arg Asp Tyr Thr Gly Gly Glu His Cys Glu Arg Cys Ile
                900                 905                 910

Ala Gly Phe His Gly Asp Pro Arg Leu Pro Tyr Gly Gly Gln Cys Arg
            915                 920                 925

Pro Cys Pro Cys Pro Glu Gly Pro Gly Ser Gln Arg His Phe Ala Thr
        930                 935                 940

Ser Cys His Arg Asp Gly Tyr Ser Gln Gln Ile Val Cys His Cys Arg
945                 950                 955                 960

Ala Gly Tyr Thr Gly Leu Arg Cys Glu Ala Cys Ala Pro Gly His Phe
```

-continued

```
                  965                 970                 975
Gly Asp Pro Ser Lys Pro Gly Gly Arg Cys Gln Leu Cys Glu Cys Ser
                980                 985                 990
Gly Asn Ile Asp Pro Thr Asp Pro Gly Ala Cys Asp Pro His Thr Gly
                995                1000                1005
Gln Cys Leu Arg Cys Leu His His Thr Glu Gly Pro His Cys Gly His
               1010                1015                1020
Cys Lys Pro Gly Phe His Gly Gln Ala Ala Arg Gln Ser Cys His Arg
1025                1030                1035                1040
Cys Thr Cys Asn Leu Leu Gly Thr Asp Pro Gln Arg Cys Pro Ser Thr
               1045                1050                1055
Asp Leu Cys His Cys Asp Pro Ser Thr Gly Gln Cys Pro Cys Leu Pro
               1060                1065                1070
His Val Gln Gly Leu Ser Cys Asp Arg Cys Ala Pro Asn Phe Trp Asn
               1075                1080                1085
Phe Thr Ser Gly Arg Gly Cys Gln Pro Cys Ala Cys His Pro Ser Arg
               1090                1095                1100
Ala Arg Gly Pro Thr Cys Asn Glu Phe Thr Gly Gln Cys His Cys His
1105                1110                1115                1120
Ala Gly Phe Gly Gly Arg Thr Cys Ser Glu Cys Gln Glu Leu His Trp
               1125                1130                1135
Gly Asp Pro Gly Leu Gln Cys Arg Ala Cys Asp Cys Asp Pro Arg Gly
               1140                1145                1150
Ile Asp Lys Pro Gln Cys His Arg Ser Thr Gly His Cys Ser Cys Arg
               1155                1160                1165
Pro Gly Val Ser Gly Val Arg Cys Asp Gln Cys Ala Arg Gly Phe Ser
               1170                1175                1180
Gly Val Phe Pro Ala Cys His Pro Cys His Ala Cys Phe Gly Asp Trp
1185                1190                1195                1200
Asp Arg Val Val Gln Asp Leu Ala Ala Arg Thr Arg Arg Leu Glu Gln
               1205                1210                1215
Trp Ala Gln Glu Leu Gln Gln Thr Gly Val Leu Gly Ala Phe Glu Ser
               1220                1225                1230
Ser Phe Leu Asn Leu Gln Gly Lys Leu Gly Met Val Gln Ala Ile Val
               1235                1240                1245
Ala Ala Arg Asn Thr Ser Ala Ala Ser Thr Ala Lys Leu Val Glu Ala
               1250                1255                1260
Thr Glu Gly Leu Arg His Glu Ile Gly Lys Thr Thr Glu Arg Leu Thr
1265                1270                1275                1280
Gln Leu Glu Ala Glu Leu Thr Asp Val Gln Asp Glu Asn Phe Asn Ala
               1285                1290                1295
Asn His Ala Leu Ser Gly Leu Glu Arg Asp Gly Leu Ala Leu Asn Leu
               1300                1305                1310
Thr Leu Arg Gln Leu Asp Gln His Leu Asp Ile Leu Lys His Ser Asn
               1315                1320                1325
Phe Leu Gly Ala Tyr Asp Ser Ile Arg His Ala His Ser Gln Ser Thr
               1330                1335                1340
Glu Ala Glu Arg Arg Ala Asn Ala Ser Thr Phe Ala Ile Pro Ser Pro
1345                1350                1355                1360
Val Ser Asn Ser Ala Asp Thr Arg Arg Ala Glu Val Leu Met Gly
               1365                1370                1375
Ala Gln Arg Glu Asn Phe Asn Arg Gln His Leu Ala Asn Gln Gln Ala
               1380                1385                1390
```

-continued

Leu Gly Arg Leu Ser Thr His Thr His Thr Leu Ser Leu Thr Gly Val
        1395                1400                1405

Asn Glu Leu Val Cys Gly Ala Pro Gly Asp Ala Pro Cys Ala Thr Ser
    1410                1415                1420

Pro Cys Gly Gly Ala Gly Cys Arg Asp Glu Asp Gly Gln Pro Arg Cys
1425                1430                1435                1440

Gly Gly Leu Gly Cys Ser Gly Ala Ala Ala Thr Ala Asp Leu Ala Leu
            1445                1450                1455

Gly Arg Ala Arg His Thr Gln Ala Glu Leu Gln Arg Ala Leu Val Glu
        1460                1465                1470

Gly Gly Gly Ile Leu Ser Arg Val Ser Glu Thr Arg Gln Ala Glu
        1475                1480                1485

Glu Ala Gln Gln Arg Ala Gln Ala Ala Leu Asp Lys Ala Asn Ala Ser
    1490                1495                1500

Arg Gly Gln Val Glu Gln Ala Asn Gln Glu Leu Arg Glu Leu Ile Gln
1505                1510                1515                1520

Asn Val Lys Asp Phe Leu Ser Gln Glu Gly Ala Asp Pro Asp Ser Ile
            1525                1530                1535

Glu Met Val Ala Thr Arg Val Leu Asp Ile Ser Ile Pro Ala Ser Pro
        1540                1545                1550

Glu Gln Ile Gln Arg Leu Ala Ser Glu Ile Ala Glu Arg Val Arg Ser
        1555                1560                1565

Leu Ala Asp Val Asp Thr Ile Leu Ala His Thr Met Gly Asp Val Arg
    1570                1575                1580

Arg Ala Glu Gln Leu Leu Gln Asp Ala Gln Arg Ala Arg Ser Arg Ala
1585                1590                1595                1600

Glu Gly Glu Arg Gln Lys Ala Glu Thr Val Gln Ala Ala Leu Glu Glu
            1605                1610                1615

Ala Gln Arg Ala Gln Gly Ala Ala Gln Gly Ala Ile Arg Gly Ala Val
        1620                1625                1630

Val Asp Thr Lys Asn Thr Glu Gln Thr Leu Gln Gln Val Gln Glu Arg
    1635                1640                1645

Met Ala Gly Thr Glu Gln Ser Leu Asn Ser Ala Ser Glu Arg Ala Arg
    1650                1655                1660

Gln Leu His Ala Leu Leu Glu Ala Leu Lys Leu Lys Arg Ala Gly Asn
1665                1670                1675                1680

Ser Leu Ala Ala Ser Thr Ala Glu Glu Thr Ala Gly Ser Ala Gln Ser
            1685                1690                1695

Arg Ala Arg Glu Ala Glu Lys Gln Leu Arg Glu Gln Val Gly Asp Gln
        1700                1705                1710

Tyr Gln Thr Val Arg Ala Leu Ala Glu Arg Lys Ala Glu Gly Val Leu
        1715                1720                1725

Ala Ala Gln Ala Arg Ala Glu Gln Leu Arg Asp Glu Ala Arg Gly Leu
    1730                1735                1740

Leu Gln Ala Ala Gln Asp Lys Leu Gln Arg Leu Gln Glu Leu Glu Gly
1745                1750                1755                1760

Thr Tyr Glu Glu Asn Glu Arg Glu Leu Glu Val Lys Ala Ala Gln Leu
            1765                1770                1775

Asp Gly Leu Glu Ala Arg Met Arg Ser Val Leu Gln Ala Ile Asn Leu
        1780                1785                1790

Gln Val Gln Ile Tyr Asn Thr Cys Gln
        1795                1800

```
<210> SEQ ID NO 9
<211> LENGTH: 1798
<212> TYPE: PRT
<213> ORGANISM: Homo Sapiens
<300> PUBLICATION INFORMATION:
<308> DATABASE ACCESSION NUMBER: Swissprot P55268
<309> DATABASE ENTRY DATE: 1996-10-01

<400> SEQUENCE: 9

Met Glu Leu Thr Ser Arg Glu Arg Gly Arg Gly Gln Pro Leu Pro Trp
 1               5                  10                  15

Glu Leu Arg Leu Gly Leu Leu Leu Ser Val Leu Ala Ala Thr Leu Ala
             20                  25                  30

Gln Ala Pro Ala Pro Asp Val Pro Gly Cys Ser Arg Gly Ser Cys Tyr
         35                  40                  45

Pro Ala Thr Gly Asp Leu Leu Val Gly Arg Ala Asp Arg Leu Thr Ala
     50                  55                  60

Ser Ser Thr Cys Gly Leu Asn Gly Pro Gln Pro Tyr Cys Ile Val Ser
 65                  70                  75                  80

His Leu Gln Asp Glu Lys Lys Cys Phe Leu Cys Asp Ser Arg Arg Pro
                 85                  90                  95

Phe Ser Ala Arg Asp Asn Pro His Ser His Arg Ile Gln Asn Val Val
            100                 105                 110

Thr Ser Phe Ala Pro Gln Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365
```

```
Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
            435                 440                 445

Cys Gln Gln Cys Arg Asp Gly Phe Phe Gly Leu Ser Ile Ser Asp Arg
        450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
            675                 680                 685

Tyr Lys Leu His Leu Lys Leu Val Arg Thr Gly Gly Ser Ala Gln Pro
        690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
            740                 745                 750

Gly Leu Val Pro Ser Lys Thr Ser Pro Ser Glu Ala Cys Ala Pro Leu
            755                 760                 765

Leu Ile Ser Leu Ser Thr Leu Ile Tyr Asn Gly Ala Leu Pro Cys Gln
        770                 775                 780
```

```
Cys Asn Pro Gln Gly Ser Leu Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
            835                 840                 845

Gln Cys Leu Cys Arg Thr Gly Ala Phe Gly Leu Arg Cys Asp Arg Cys
        850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
                900                 905                 910

His Arg Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
            995                 1000                1005

Arg Cys Leu His His Thr Glu Gly Pro His Cys Ala His Cys Lys Pro
    1010                1015                1020

Gly Phe His Gly Gln Ala Ala Arg Gln Ser Cys His Arg Cys Thr Cys
1025                1030                1035                1040

Asn Leu Leu Gly Thr Asn Pro Gln Gln Cys Pro Ser Pro Asp Gln Cys
                1045                1050                1055

His Cys Asp Pro Ser Ser Gly Gln Cys Pro Cys Leu Pro Asn Val Gln
            1060                1065                1070

Gly Pro Ser Cys Asp Arg Cys Ala Pro Asn Phe Trp Asn Leu Thr Ser
        1075                1080                1085

Gly His Gly Cys Gln Pro Cys Ala Cys His Pro Ser Arg Ala Arg Gly
    1090                1095                1100

Pro Thr Cys Asn Glu Phe Thr Gly Gln Cys His Cys Arg Ala Gly Phe
1105                1110                1115                1120

Gly Gly Arg Thr Cys Ser Glu Cys Gln Glu Leu His Trp Gly Asp Pro
                1125                1130                1135

Gly Leu Gln Cys His Ala Cys Asp Cys Asp Ser Arg Gly Ile Asp Thr
            1140                1145                1150

Pro Gln Cys His Arg Phe Thr Gly His Cys Ser Cys Arg Pro Gly Val
        1155                1160                1165

Ser Gly Val Arg Cys Asp Gln Cys Ala Arg Gly Phe Ser Gly Ile Phe
    1170                1175                1180

Pro Ala Cys His Pro Cys His Ala Cys Phe Gly Asp Trp Asp Arg Val
1185                1190                1195                1200

Val Gln Asp Leu Ala Ala Arg Thr Gln Arg Leu Glu Gln Arg Ala Gln
```

-continued

```
                1205                1210                1215
Glu Leu Gln Gln Thr Gly Val Leu Gly Ala Phe Glu Ser Ser Phe Trp
                1220                1225                1230
His Met Gln Glu Lys Leu Gly Ile Val Gln Gly Ile Val Gly Ala Arg
                1235                1240                1245
Asn Thr Ser Ala Ala Ser Thr Ala Gln Leu Val Glu Ala Thr Glu Glu
                1250                1255                1260
Leu Arg Arg Glu Ile Gly Glu Ala Thr Glu His Leu Thr Gln Leu Glu
1265                1270                1275                1280
Ala Asp Leu Thr Asp Val Gln Asp Glu Asn Phe Asn Ala Asn His Ala
                1285                1290                1295
Leu Ser Gly Leu Glu Arg Asp Arg Leu Ala Leu Asn Leu Thr Leu Arg
                1300                1305                1310
Gln Leu Asp Gln His Leu Asp Leu Leu Lys His Ser Asn Phe Leu Gly
                1315                1320                1325
Ala Tyr Asp Ser Ile Arg His Ala His Ser Gln Ser Ala Glu Ala Glu
                1330                1335                1340
Arg Arg Ala Asn Thr Ser Ala Leu Ala Val Pro Ser Pro Val Ser Asn
1345                1350                1355                1360
Ser Ala Ser Ala Arg His Arg Thr Glu Ala Leu Met Asp Ala Gln Lys
                1365                1370                1375
Glu Asp Phe Asn Ser Lys His Met Ala Asn Gln Arg Ala Leu Gly Lys
                1380                1385                1390
Leu Ser Ala His Thr His Thr Leu Ser Leu Thr Asp Ile Asn Glu Leu
                1395                1400                1405
Val Cys Gly Ala Pro Gly Asp Ala Pro Cys Ala Thr Ser Pro Cys Gly
                1410                1415                1420
Gly Ala Gly Cys Arg Asp Glu Asp Gly Gln Pro Arg Cys Gly Gly Leu
1425                1430                1435                1440
Ser Cys Asn Gly Ala Ala Ala Thr Ala Asp Leu Ala Leu Gly Arg Ala
                1445                1450                1455
Arg His Thr Gln Ala Glu Leu Gln Arg Ala Leu Ala Glu Gly Gly Ser
                1460                1465                1470
Ile Leu Ser Arg Val Ala Glu Thr Arg Arg Gln Ala Ser Glu Ala Gln
                1475                1480                1485
Gln Arg Ala Gln Ala Ala Leu Asp Lys Ala Asn Ala Ser Arg Gly Gln
                1490                1495                1500
Val Glu Gln Ala Asn Gln Glu Leu Gln Glu Leu Ile Gln Ser Val Lys
1505                1510                1515                1520
Asp Phe Leu Asn Gln Glu Gly Ala Asp Pro Asp Ser Ile Glu Met Val
                1525                1530                1535
Ala Thr Arg Val Leu Glu Leu Ser Ile Pro Ala Ser Ala Glu Gln Ile
                1540                1545                1550
Gln His Leu Ala Gly Ala Ile Ala Glu Arg Val Arg Ser Leu Ala Asp
                1555                1560                1565
Val Asp Ala Ile Leu Ala Arg Thr Val Gly Asp Val Arg Arg Ala Glu
                1570                1575                1580
Gln Leu Leu Gln Asp Ala Arg Arg Ala Arg Ser Trp Ala Glu Asp Glu
1585                1590                1595                1600
Lys Gln Lys Ala Glu Thr Val Gln Ala Ala Leu Glu Glu Ala Gln Arg
                1605                1610                1615
Ala Gln Gly Ile Ala Gln Gly Ala Ile Arg Gly Ala Val Ala Asp Thr
                1620                1625                1630
```

-continued

```
Arg Asp Thr Glu Gln Thr Leu Tyr Gln Val Gln Glu Arg Met Ala Gly
        1635                1640                1645

Ala Glu Arg Ala Leu Ser Ser Ala Gly Glu Arg Ala Arg Gln Leu Asp
        1650                1655                1660

Ala Leu Leu Glu Ala Leu Lys Leu Lys Arg Ala Gly Asn Ser Leu Ala
1665                1670                1675                1680

Ala Ser Thr Ala Glu Glu Thr Ala Gly Ser Ala Gln Gly Arg Ala Gln
        1685                1690                1695

Glu Ala Glu Gln Leu Leu Arg Gly Pro Leu Gly Asp Gln Tyr Gln Thr
        1700                1705                1710

Val Lys Ala Leu Ala Glu Arg Lys Ala Gln Gly Val Leu Ala Ala Gln
        1715                1720                1725

Ala Arg Ala Glu Gln Leu Arg Asp Glu Ala Arg Asp Leu Leu Gln Ala
        1730                1735                1740

Ala Gln Asp Lys Leu Gln Arg Leu Gln Glu Leu Glu Gly Thr Tyr Glu
1745                1750                1755                1760

Glu Asn Glu Arg Ala Leu Glu Ser Lys Ala Ala Gln Leu Asp Gly Leu
        1765                1770                1775

Glu Ala Arg Met Arg Ser Val Leu Gln Ala Ile Asn Leu Gln Val Gln
        1780                1785                1790

Ile Tyr Asn Thr Cys Gln
        1795

<210> SEQ ID NO 10
<211> LENGTH: 1607
<212> TYPE: PRT
<213> ORGANISM: Mus Musculus
<300> PUBLICATION INFORMATION:
<308> DATABASE ACCESSION NUMBER: Swissprot P02468
<309> DATABASE ENTRY DATE: 1989-07-01

<400> SEQUENCE: 10

Met Thr Gly Gly Gly Arg Ala Ala Leu Ala Leu Gln Pro Arg Gly Arg
1               5                   10                  15

Leu Trp Pro Leu Leu Ala Val Leu Ala Val Ala Gly Cys Val Arg
            20                  25                  30

Ala Ala Met Asp Glu Cys Ala Asp Glu Gly Gly Arg Pro Gln Arg Cys
        35                  40                  45

Met Pro Glu Phe Val Asn Ala Ala Phe Asn Val Thr Val Ala Thr
        50                  55                  60

Asn Thr Cys Gly Thr Pro Pro Glu Glu Tyr Cys Val Gln Thr Gly Val
65                  70                  75                  80

Thr Gly Val Thr Lys Ser Cys His Leu Cys Asp Ala Gly Gln Gln His
            85                  90                  95

Leu Gln His Gly Ala Ala Phe Leu Thr Asp Tyr Asn Asn Gln Ala Asp
            100                 105                 110

Thr Thr Trp Trp Gln Ser Gln Thr Met Leu Ala Gly Val Gln Tyr Pro
        115                 120                 125

Asn Ser Ile Asn Leu Thr Leu His Leu Gly Lys Ala Phe Asp Ile Thr
130                 135                 140

Tyr Val Arg Leu Lys Phe His Thr Ser Arg Pro Glu Ser Phe Ala Ile
145                 150                 155                 160

Tyr Lys Arg Thr Arg Glu Asp Gly Pro Trp Ile Pro Tyr Gln Tyr Tyr
            165                 170                 175

Ser Gly Ser Cys Glu Asn Thr Tyr Ser Lys Ala Asn Arg Gly Phe Ile
```

-continued

```
            180             185                 190
Arg Thr Gly Gly Asp Glu Gln Gln Ala Leu Cys Thr Asp Glu Phe Ser
        195                 200                 205

Asp Ile Ser Pro Leu Thr Gly Gly Asn Val Ala Phe Ser Thr Leu Glu
    210                 215                 220

Gly Arg Pro Ser Ala Tyr Asn Phe Asp Asn Ser Pro Val Leu Gln Glu
225                 230                 235                 240

Trp Val Thr Ala Thr Asp Ile Arg Val Thr Leu Asn Arg Leu Asn Thr
                245                 250                 255

Phe Gly Asp Glu Val Phe Asn Glu Pro Lys Val Leu Lys Ser Tyr Tyr
            260                 265                 270

Tyr Ala Ile Ser Asp Phe Ala Val Gly Gly Arg Cys Lys Cys Asn Gly
            275                 280                 285

His Ala Ser Glu Cys Val Lys Asn Glu Phe Asp Lys Leu Met Cys Asn
    290                 295                 300

Cys Lys His Asn Thr Tyr Gly Val Asp Cys Glu Lys Cys Leu Pro Phe
305                 310                 315                 320

Phe Asn Asp Arg Pro Trp Arg Arg Ala Thr Ala Glu Ser Ala Ser Glu
                325                 330                 335

Ser Leu Pro Cys Asp Cys Asn Gly Arg Ser Gln Glu Cys Tyr Phe Asp
            340                 345                 350

Pro Glu Leu Tyr Arg Ser Thr Gly His Gly Gly His Cys Thr Asn Cys
            355                 360                 365

Arg Asp Asn Thr Asp Gly Ala Lys Cys Glu Arg Cys Arg Glu Asn Phe
    370                 375                 380

Phe Arg Leu Gly Asn Thr Glu Ala Cys Ser Pro Cys His Cys Ser Pro
385                 390                 395                 400

Val Gly Ser Leu Ser Thr Gln Cys Asp Ser Tyr Gly Arg Cys Ser Cys
                405                 410                 415

Lys Pro Gly Val Met Gly Asp Lys Cys Asp Arg Cys Gln Pro Gly Phe
            420                 425                 430

His Ser Leu Thr Glu Ala Gly Cys Arg Pro Cys Ser Cys Asp Leu Arg
        435                 440                 445

Gly Ser Thr Asp Glu Cys Asn Val Glu Thr Gly Arg Cys Val Cys Lys
450                 455                 460

Asp Asn Val Glu Gly Phe Asn Cys Glu Arg Cys Lys Pro Gly Phe Phe
465                 470                 475                 480

Asn Leu Glu Ser Ser Asn Pro Lys Gly Cys Thr Pro Cys Phe Cys Phe
                485                 490                 495

Gly His Ser Ser Val Cys Thr Asn Ala Val Gly Tyr Ser Val Tyr Asp
            500                 505                 510

Ile Ser Ser Thr Phe Gln Ile Asp Glu Asp Gly Trp Arg Val Glu Gln
            515                 520                 525

Arg Asp Gly Ser Glu Ala Ser Leu Glu Trp Ser Ser Asp Arg Gln Asp
    530                 535                 540

Ile Ala Val Ile Ser Asp Ser Tyr Phe Pro Arg Tyr Phe Ile Ala Pro
545                 550                 555                 560

Val Lys Phe Leu Gly Asn Gln Val Leu Ser Tyr Gly Gln Asn Leu Ser
                565                 570                 575

Phe Ser Phe Arg Val Asp Arg Arg Asp Thr Arg Leu Ser Ala Glu Asp
            580                 585                 590

Leu Val Leu Glu Gly Ala Gly Leu Arg Val Ser Val Pro Leu Ile Ala
        595                 600                 605
```

-continued

```
Gln Gly Asn Ser Tyr Pro Ser Glu Thr Thr Val Lys Tyr Ile Phe Arg
    610                 615                 620

Leu His Glu Ala Thr Asp Tyr Pro Trp Arg Pro Ala Leu Ser Pro Phe
625                 630                 635                 640

Glu Phe Gln Lys Leu Leu Asn Asn Leu Thr Ser Ile Lys Ile Arg Gly
            645                 650                 655

Thr Tyr Ser Glu Arg Thr Ala Gly Tyr Leu Asp Asp Val Thr Leu Gln
                660                 665                 670

Ser Ala Arg Pro Gly Pro Gly Val Pro Ala Thr Trp Val Glu Ser Cys
            675                 680                 685

Thr Cys Pro Val Gly Tyr Gly Gly Gln Phe Cys Glu Thr Cys Leu Pro
            690                 695                 700

Gly Tyr Arg Arg Glu Thr Pro Ser Leu Gly Pro Tyr Ser Pro Cys Val
705                 710                 715                 720

Leu Cys Thr Cys Asn Gly His Ser Glu Thr Cys Asp Pro Glu Thr Gly
                725                 730                 735

Val Cys Asp Cys Arg Asp Asn Thr Ala Gly Pro His Cys Glu Lys Cys
            740                 745                 750

Ser Asp Gly Tyr Tyr Gly Asp Ser Thr Leu Gly Thr Ser Ser Asp Cys
            755                 760                 765

Gln Pro Cys Pro Cys Pro Gly Gly Ser Ser Cys Ala Ile Val Pro Lys
770                 775                 780

Thr Lys Glu Val Val Cys Thr His Cys Pro Thr Gly Thr Ala Gly Lys
785                 790                 795                 800

Arg Cys Glu Leu Cys Asp Asp Gly Tyr Phe Gly Asp Pro Leu Gly Ser
                805                 810                 815

Asn Gly Pro Val Arg Leu Cys Arg Pro Cys Gln Cys Asn Asp Asn Ile
            820                 825                 830

Asp Pro Asn Ala Val Gly Asn Cys Asn Arg Leu Thr Gly Glu Cys Leu
            835                 840                 845

Lys Cys Ile Tyr Asn Thr Ala Gly Phe Tyr Cys Asp Arg Cys Lys Glu
850                 855                 860

Gly Phe Phe Gly Asn Pro Leu Ala Pro Asn Pro Ala Asp Lys Cys Lys
865                 870                 875                 880

Ala Cys Ala Cys Asn Pro Tyr Gly Thr Val Gln Gln Gln Ser Ser Cys
                885                 890                 895

Asn Pro Val Thr Gly Gln Cys Gln Cys Leu Pro His Val Ser Gly Arg
            900                 905                 910

Asp Cys Gly Thr Cys Asp Pro Gly Tyr Tyr Asn Leu Gln Ser Gly Gln
            915                 920                 925

Gly Cys Glu Arg Cys Asp Cys His Ala Leu Gly Ser Thr Asn Gly Gln
            930                 935                 940

Cys Asp Ile Arg Thr Gly Gln Cys Glu Cys Gln Pro Gly Ile Thr Gly
945                 950                 955                 960

Gln His Cys Glu Arg Cys Glu Thr Asn His Phe Gly Phe Gly Pro Glu
                965                 970                 975

Gly Cys Lys Pro Cys Asp Cys His His Glu Gly Ser Leu Ser Leu Gln
            980                 985                 990

Cys Lys Asp Asp Gly Arg Cys Glu Cys Arg Glu Gly Phe Val Gly Asn
            995                 1000                1005

Arg Cys Asp Gln Cys Glu Glu Asn Tyr Phe Tyr Asn Arg Ser Trp Pro
1010                1015                1020
```

-continued

```
Gly Cys Gln Glu Cys Pro Ala Cys Tyr Arg Leu Val Lys Asp Lys Ala
1025                1030                1035                1040

Ala Glu His Arg Val Lys Leu Gln Glu Leu Glu Ser Leu Ile Ala Asn
            1045                1050                1055

Leu Gly Thr Gly Asp Asp Met Val Thr Asp Gln Ala Phe Glu Asp Arg
        1060                1065                1070

Leu Lys Glu Ala Glu Arg Glu Val Thr Asp Leu Leu Arg Glu Ala Gln
    1075                1080                1085

Glu Val Lys Asp Val Asp Gln Asn Leu Met Asp Arg Leu Gln Arg Val
1090                1095                1100

Asn Ser Ser Leu His Ser Gln Ile Ser Arg Leu Gln Asn Ile Arg Asn
1105                1110                1115                1120

Thr Ile Glu Glu Thr Gly Ile Leu Ala Glu Arg Ala Arg Ser Arg Val
            1125                1130                1135

Glu Ser Thr Glu Gln Leu Ile Glu Ile Ala Ser Arg Glu Leu Glu Lys
        1140                1145                1150

Ala Lys Met Ala Ala Ala Asn Val Ser Ile Thr Gln Pro Glu Ser Thr
    1155                1160                1165

Gly Glu Pro Asn Asn Met Thr Leu Leu Ala Glu Ala Arg Arg Leu
1170                1175                1180

Ala Glu Arg His Lys Gln Glu Ala Asp Asp Ile Val Arg Val Ala Lys
1185                1190                1195                1200

Thr Ala Asn Glu Thr Ser Ala Glu Ala Tyr Asn Leu Leu Leu Arg Thr
            1205                1210                1215

Leu Ala Gly Glu Asn Gln Thr Ala Leu Glu Ile Glu Glu Leu Asn Arg
        1220                1225                1230

Lys Tyr Glu Gln Ala Lys Asn Ile Ser Gln Asp Leu Glu Lys Gln Ala
    1235                1240                1245

Ala Arg Val His Glu Glu Ala Lys Arg Ala Gly Asp Lys Ala Val Glu
1250                1255                1260

Ile Tyr Ala Ser Val Ala Gln Leu Thr Pro Val Asp Ser Glu Ala Leu
1265                1270                1275                1280

Glu Asn Glu Ala Asn Lys Ile Lys Lys Glu Ala Ala Asp Leu Asp Arg
            1285                1290                1295

Leu Ile Asp Gln Lys Leu Lys Asp Tyr Glu Asp Leu Arg Glu Asp Met
        1300                1305                1310

Arg Gly Lys Glu His Glu Val Lys Asn Leu Leu Glu Lys Gly Lys Ala
    1315                1320                1325

Glu Gln Gln Thr Ala Asp Gln Leu Leu Ala Arg Ala Asp Ala Ala Lys
1330                1335                1340

Ala Leu Ala Glu Glu Ala Ala Lys Lys Gly Arg Ser Thr Leu Gln Glu
1345                1350                1355                1360

Ala Asn Asp Ile Leu Asn Asn Leu Lys Asp Phe Asp Arg Arg Val Asn
            1365                1370                1375

Asp Asn Lys Thr Ala Ala Glu Glu Ala Leu Arg Arg Ile Pro Ala Ile
        1380                1385                1390

Asn Arg Thr Ile Ala Glu Ala Asn Glu Lys Thr Arg Glu Ala Gln Leu
    1395                1400                1405

Ala Leu Gly Asn Ala Ala Ala Asp Ala Thr Glu Ala Lys Asn Lys Ala
    1410                1415                1420

His Glu Ala Glu Arg Ile Ala Ser Ala Val Gln Lys Asn Ala Thr Ser
1425                1430                1435                1440

Thr Lys Ala Asp Ala Glu Arg Thr Phe Gly Glu Val Thr Asp Leu Asp
```

-continued

```
                1445                1450                1455
Asn Glu Val Asn Gly Met Leu Arg Gln Leu Glu Glu Ala Glu Asn Glu
            1460                1465                1470

Leu Lys Arg Lys Gln Asp Asp Ala Asp Gln Asp Met Met Met Ala Gly
        1475                1480                1485

Met Ala Ser Gln Ala Ala Gln Glu Ala Glu Leu Asn Ala Arg Lys Ala
        1490                1495                1500

Lys Asn Ser Val Ser Ser Leu Leu Ser Gln Leu Asn Asn Leu Leu Asp
1505                1510                1515                1520

Gln Leu Gly Gln Leu Asp Thr Val Asp Leu Asn Lys Leu Asn Glu Ile
            1525                1530                1535

Glu Gly Ser Leu Asn Lys Ala Lys Asp Glu Met Lys Ala Ser Asp Leu
            1540                1545                1550

Asp Arg Lys Val Ser Asp Leu Glu Ser Glu Ala Arg Lys Gln Glu Ala
        1555                1560                1565

Ala Ile Met Asp Tyr Asn Arg Asp Ile Ala Glu Ile Ile Lys Asp Ile
    1570                1575                1580

His Asn Leu Glu Asp Ile Lys Lys Thr Leu Pro Thr Gly Cys Phe Asn
1585                1590                1595                1600

Thr Pro Ser Ile Glu Lys Pro
            1605

<210> SEQ ID NO 11
<211> LENGTH: 1609
<212> TYPE: PRT
<213> ORGANISM: Homo Sapiens
<300> PUBLICATION INFORMATION:
<308> DATABASE ACCESSION NUMBER: Swissprot P11047
<309> DATABASE ENTRY DATE: 1991-11-01

<400> SEQUENCE: 11

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
            85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
            165                 170                 175

Tyr Tyr Ser Gly Ser Cys Glu Asn Thr Tyr Ser Lys Ala Asn Arg Gly
            180                 185                 190
```

-continued

```
Phe Ile Arg Thr Gly Gly Asp Glu Gln Gln Ala Leu Cys Thr Asp Glu
        195                 200                 205
Phe Ser Asp Phe Ser Pro Leu Thr Gly Gly Asn Val Ala Phe Ser Thr
        210                 215                 220
Leu Glu Gly Arg Pro Ser Ala Tyr Asn Phe Asp Asn Ser Pro Val Leu
225                 230                 235                 240
Gln Glu Trp Val Thr Ala Thr Asp Ile Arg Val Thr Leu Asn Arg Leu
                    245                 250                 255
Asn Thr Phe Gly Asp Glu Val Phe Asn Asp Pro Lys Val Leu Lys Ser
                260                 265                 270
Tyr Tyr Tyr Ala Ile Ser Asp Phe Ala Val Gly Arg Cys Lys Cys
            275                 280                 285
Asn Gly His Ala Ser Glu Cys Met Lys Asn Glu Phe Asp Lys Leu Val
        290                 295                 300
Cys Asn Cys Lys His Asn Thr Tyr Gly Val Asp Cys Glu Lys Cys Leu
305                 310                 315                 320
Pro Phe Phe Asn Asp Arg Pro Trp Arg Arg Ala Thr Ala Glu Ser Ala
                325                 330                 335
Ser Glu Cys Leu Pro Cys Asp Cys Asn Gly Arg Ser Gln Glu Cys Tyr
                340                 345                 350
Phe Asp Pro Glu Leu Tyr Arg Ser Thr Gly His Gly Gly His Cys Thr
                355                 360                 365
Asn Cys Gln Asp Asn Thr Asp Gly Ala His Cys Glu Arg Cys Arg Glu
        370                 375                 380
Asn Phe Phe Arg Leu Gly Asn Asn Glu Ala Cys Ser Ser Cys His Cys
385                 390                 395                 400
Ser Pro Val Gly Ser Leu Ser Thr Gln Cys Asp Ser Tyr Gly Arg Cys
                405                 410                 415
Ser Cys Lys Pro Gly Val Met Gly Asp Lys Cys Asp Arg Cys Gln Pro
                420                 425                 430
Gly Phe His Ser Leu Thr Glu Ala Gly Cys Arg Pro Cys Ser Cys Asp
        435                 440                 445
Pro Ser Gly Ser Ile Asp Glu Cys Asn Val Glu Thr Gly Arg Cys Val
450                 455                 460
Cys Lys Asp Asn Val Glu Gly Phe Asn Cys Glu Arg Cys Lys Pro Gly
465                 470                 475                 480
Phe Phe Asn Leu Glu Ser Ser Asn Pro Arg Gly Cys Thr Pro Cys Phe
                485                 490                 495
Cys Phe Gly His Ser Ser Val Cys Thr Asn Ala Val Gly Tyr Ser Val
                500                 505                 510
Tyr Ser Ile Ser Ser Thr Phe Gln Ile Asp Glu Asp Gly Trp Arg Ala
                515                 520                 525
Glu Gln Arg Asp Gly Ser Glu Ala Ser Leu Glu Trp Ser Ser Glu Arg
                530                 535                 540
Gln Asp Ile Ala Val Ile Ser Asp Ser Tyr Phe Pro Arg Tyr Phe Ile
545                 550                 555                 560
Ala Pro Ala Lys Phe Leu Gly Lys Gln Val Leu Ser Tyr Gly Gln Asn
                565                 570                 575
Leu Ser Phe Ser Phe Arg Val Asp Arg Arg Asp Thr Arg Leu Ser Ala
                580                 585                 590
Glu Asp Leu Val Leu Glu Gly Ala Gly Leu Arg Val Ser Val Pro Leu
                595                 600                 605
Ile Ala Gln Gly Asn Ser Tyr Pro Ser Glu Thr Thr Val Lys Tyr Val
```

-continued

```
            610                 615                 620
Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
                660                 665                 670

Leu Ala Ser Ala Arg Pro Gly Pro Val Pro Ala Thr Trp Val Glu
            675                 680                 685

Ser Cys Thr Cys Pro Val Gly Tyr Gly Gly Gln Phe Cys Glu Met Cys
            690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
                740                 745                 750

Lys Cys Ser Asp Gly Tyr Tyr Gly Asp Ser Thr Ala Gly Thr Ser Ser
            755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
                820                 825                 830

Asn Ile Asp Pro Asn Ala Val Gly Asn Cys Asn Arg Leu Thr Gly Glu
            835                 840                 845

Cys Leu Lys Cys Ile Tyr Asn Thr Ala Gly Phe Tyr Cys Asp Arg Cys
    850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Pro Tyr Gly Thr Met Lys Gln Gln Ser
                885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
            915                 920                 925

Gly Gln Gly Cys Glu Arg Cys Asp Cys His Ala Leu Gly Ser Thr Asn
            930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
                980                 985                 990

Leu Gln Cys Lys Asp Asp Gly Arg Cys Glu Cys Arg Glu Gly Phe Val
            995                 1000                1005

Gly Asn Arg Cys Asp Gln Cys Glu Glu Asn Tyr Phe Tyr Asn Arg Ser
        1010                1015                1020

Trp Pro Gly Cys Gln Glu Cys Pro Ala Cys Tyr Arg Leu Val Lys Asp
1025                1030                1035                1040
```

-continued

```
Lys Val Ala Asp His Arg Val Lys Leu Gln Glu Leu Glu Ser Leu Ile
            1045                1050                1055

Ala Asn Leu Gly Thr Gly Asp Glu Met Val Thr Asp Gln Ala Phe Glu
            1060                1065                1070

Asp Arg Leu Lys Glu Ala Glu Arg Glu Val Met Asp Leu Leu Arg Glu
            1075                1080                1085

Ala Gln Asp Val Lys Asp Val Asp Gln Asn Leu Met Asp Arg Leu Gln
            1090                1095                1100

Arg Val Asn Asn Thr Leu Ser Ser Gln Ile Ser Arg Leu Gln Asn Ile
1105                1110                1115                1120

Arg Asn Thr Ile Glu Glu Thr Gly Asn Leu Ala Glu Gln Ala Arg Ala
            1125                1130                1135

His Val Glu Asn Thr Glu Arg Leu Ile Glu Ile Ala Ser Arg Glu Leu
            1140                1145                1150

Glu Lys Ala Lys Val Ala Ala Ala Asn Val Ser Val Thr Gln Pro Glu
            1155                1160                1165

Ser Thr Gly Asp Pro Asn Asn Met Thr Leu Leu Ala Glu Glu Ala Arg
            1170                1175                1180

Lys Leu Ala Glu Arg His Lys Gln Glu Ala Asp Asp Ile Val Arg Val
1185                1190                1195                1200

Ala Lys Thr Ala Asn Asp Thr Ser Thr Glu Ala Tyr Asn Leu Leu
            1205                1210                1215

Arg Thr Leu Ala Gly Glu Asn Gln Thr Ala Phe Glu Ile Glu Glu Leu
            1220                1225                1230

Asn Arg Lys Tyr Glu Gln Ala Lys Asn Ile Ser Gln Asp Leu Glu Lys
            1235                1240                1245

Gln Ala Ala Arg Val His Glu Glu Ala Lys Arg Ala Gly Asp Lys Ala
            1250                1255                1260

Val Glu Ile Tyr Ala Ser Val Ala Gln Leu Ser Pro Leu Asp Ser Glu
1265                1270                1275                1280

Thr Leu Glu Asn Glu Ala Asn Asn Ile Lys Met Glu Ala Glu Asn Leu
            1285                1290                1295

Glu Gln Leu Ile Asp Gln Lys Leu Lys Asp Tyr Glu Asp Leu Arg Glu
            1300                1305                1310

Asp Met Arg Gly Lys Glu Leu Glu Val Lys Asn Leu Leu Glu Lys Gly
            1315                1320                1325

Lys Thr Glu Gln Gln Thr Ala Asp Gln Leu Leu Ala Arg Ala Asp Ala
            1330                1335                1340

Ala Lys Ala Leu Ala Glu Glu Ala Ala Lys Lys Gly Arg Asp Thr Leu
1345                1350                1355                1360

Gln Glu Ala Asn Asp Ile Leu Asn Asn Leu Lys Asp Phe Asp Arg Arg
            1365                1370                1375

Val Asn Asp Asn Lys Thr Ala Ala Glu Glu Ala Leu Arg Lys Ile Pro
            1380                1385                1390

Ala Ile Asn Gln Thr Ile Thr Glu Ala Asn Glu Lys Thr Arg Glu Ala
            1395                1400                1405

Gln Gln Ala Leu Gly Ser Ala Ala Ala Asp Ala Thr Glu Ala Lys Asn
            1410                1415                1420

Lys Ala His Glu Ala Glu Arg Ile Ala Ser Ala Val Gln Lys Asn Ala
1425                1430                1435                1440

Thr Ser Thr Lys Ala Glu Ala Glu Arg Thr Phe Ala Glu Val Thr Asp
            1445                1450                1455
```

-continued

```
Leu Asp Asn Glu Val Asn Asn Met Leu Lys Gln Leu Gln Glu Ala Glu
            1460                1465                1470

Lys Glu Leu Lys Arg Lys Gln Asp Asp Ala Asp Gln Asp Met Met Met
        1475                1480                1485

Ala Gly Met Ala Ser Gln Ala Ala Gln Glu Ala Glu Ile Asn Ala Arg
    1490                1495                1500

Lys Ala Lys Asn Ser Val Thr Ser Leu Leu Ser Ile Ile Asn Asp Leu
1505                1510                1515                1520

Leu Glu Gln Leu Gly Gln Leu Asp Thr Val Asp Leu Asn Lys Leu Asn
                1525                1530                1535

Glu Ile Glu Gly Thr Leu Asn Lys Ala Lys Asp Glu Met Lys Val Ser
            1540                1545                1550

Asp Leu Asp Arg Lys Val Ser Asp Leu Glu Asn Glu Ala Lys Lys Gln
        1555                1560                1565

Glu Ala Ala Ile Met Asp Tyr Asn Arg Asp Ile Glu Glu Ile Met Lys
    1570                1575                1580

Asp Ile Arg Asn Leu Glu Asp Ile Arg Lys Thr Leu Pro Ser Gly Cys
1585                1590                1595                1600

Phe Asn Thr Pro Ser Ile Glu Lys Pro
                1605
```